Figure 1:
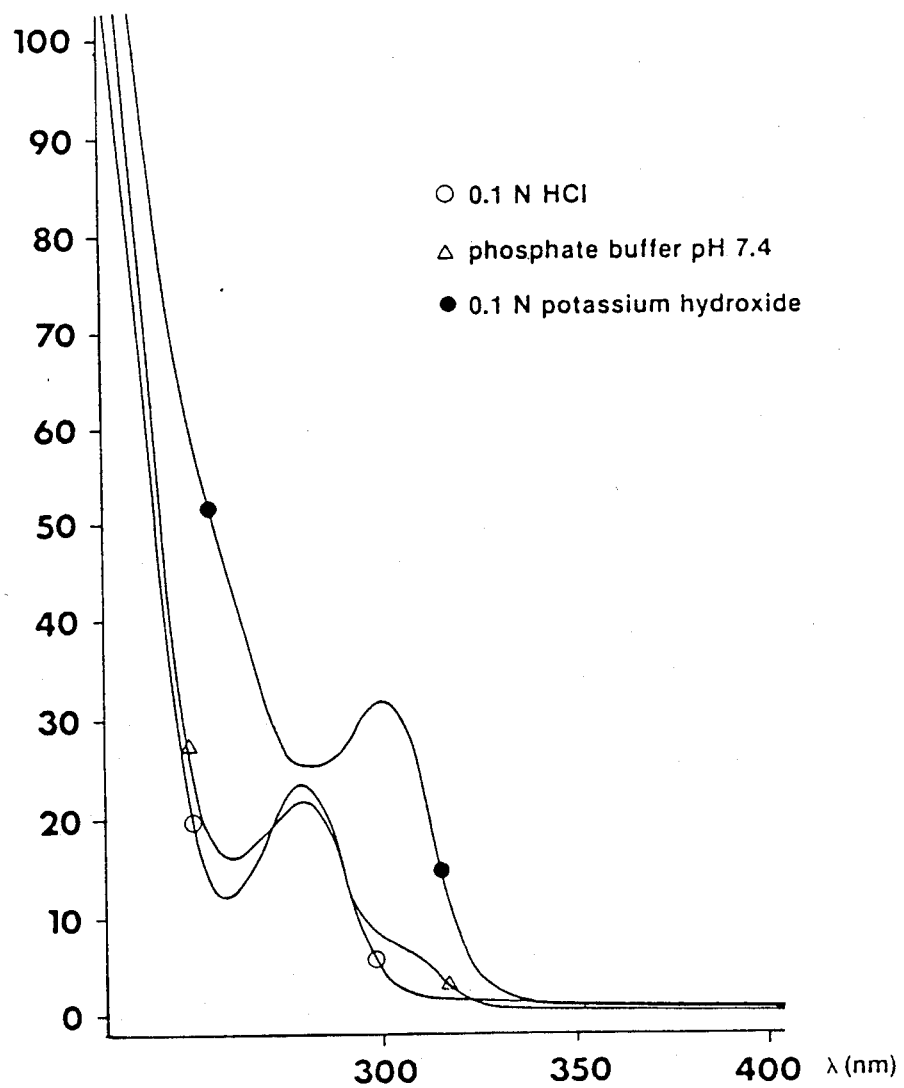

United States Patent [19]

Selva et al.

[11] Patent Number: 4,868,171
[45] Date of Patent: Sep. 19, 1989

[54] ANTIBIOTIC A 40926 N-ACYLAMINOGLUCURONYL AGLYCONS AND ANTIOBIOTIC A 40926 AGLYCON

[75] Inventors: Enrico Selva, Gropello Cairoli; Ernesto Riva, Milan; Giovanni Cassani, Pavia; Francesco Parenti, Lainate, all of Italy

[73] Assignee: Gruppo Lepetit S.p.A., Gerenzano, Italy

[21] Appl. No.: 945,639

[22] Filed: Dec. 23, 1986

[30] Foreign Application Priority Data

Apr. 11, 1986 [GB] United Kingdom ............... 8608809

[51] Int. Cl.$^4$ ............... C07D 498/18; A61K 31/395
[52] U.S. Cl. ............................. 514/183; 540/456; 424/118; 424/119
[58] Field of Search ................ 514/183; 540/456; 424/118, 119

[56] References Cited

U.S. PATENT DOCUMENTS

| | | | |
|---|---|---|---|
| 4,629,781 | 12/1986 | Strazzolini et al. | 530/317 |
| 4,645,827 | 2/1987 | Malabarba et al. | 530/322 |
| 4,650,855 | 3/1987 | Malabarba et al. | 530/322 |

FOREIGN PATENT DOCUMENTS

| | | | |
|---|---|---|---|
| 0132116 | 7/1983 | European Pat. Off. | 530/322 |
| 177882 | 4/1986 | European Pat. Off. | 540/456 |

OTHER PUBLICATIONS

Grant and Hackh's, "Chemical Dictionary", (5th Ed.), (McGraw Hill), (1987), p. 14.
J. Williams, J. Amer. Chem. Soc., 106, 4895–4908 (1984).

*Primary Examiner*—Robert T. Bond
*Attorney, Agent, or Firm*—J. Michael Dixon

[57] ABSTRACT

The present invention concerns new antibiotic substances denominated antibiotic A 40926 N-acylaminoglucuronyl aglycon complex AB, antibiotic A 40926 N-acylaminoglucuronyl aglycon factor A, antibiotic A 40926 N-acylaminoglucuronyl aglycon factor B, antibiotic A 40926 N-acylaminoglucuronyl aglycon factor $B_0$, antibiotic A 40926 N-acylaminoglucuronyl aglycon factor $B_1$, antibiotic A 40926 aglycon and the addition salts thereof, a process for their preparation starting from antibiotic A 40926 complex or a factor thereof, and their use in the treatment of infectious diseases involving microorganisms susceptible to them.

11 Claims, 26 Drawing Sheets

ANTIBIOTIC A 40926 N-ACYLAMINOGLUCURONYL AGLYCONS AND ANTIOBIOTIC A 40926 AGLYCON

The present invention concerns new antibiotic substances denominated antibiotic A 40926 N-acylaminoglucuronyl aglycon complex AB. antibiotic A 40926 N-acylaminogluycuronyl aglycon factor A, antibiotic A 40926 N-acylaminoglucuronyl aglycon factor B, antibiotic A 40926 N-acylaminoglucuronyl aglycon factor $B_0$, antibiotic A 40926 N-acylaminoglucuronyl aglycon factor $B_1$, antibiotic A 40926 aglycon and the addition salts thereof, a process for their preparation starting from antibiotic A 40926 complex or a factor thereof, and their use in the treatment of infectious diseases involving microorganisms susceptible to them.

Antibiotic A 40926 complex and its factors are antibiotic substances active against gram positive bacteria and Neisseriae strains, which are produced by strains of Actinomadura.

An A 40926 producing strain of Actinomadura genus has been deposited on June 8, 1984 with American Type Culture Collection (ATCC)–12301 Parklawn Drive, Rockville, Md. 20852, U.S.A. under the provisions of the Budapest Treaty.

Antibiotic A 40926 and its factors, as well as the producing microorganism and the process for their preparation, have been disclosed in European Patent Application Publication No. 177882. On the basis of the physico-chemical data and by reference to the structure of known antibiotic substances, the following formula can be attributed to the A 40926 factors (the numbering is analogous to that proposed by J. Williams in J.A.C.S., 106, 4895–4908 (1984)):

dodecanoylaminoglucuronyl and B represents mannosyl.

Antibiotic A 40926 factor PA and factor PB differ from the corresponding factors A and B in that the mannose unit is replaced by an acetyl-mannose unit.

Antibiotic A 40926 is a complex antimicrobial substance; five of its components have been isolated and identified as factor PA, PB, A, B and $B_0$.

Antibiotic A 40926 factors PA and PB, at least under certain fermentation conditions, are the main antibiotic products of the A 40926 producing microorganism.

Antibiotic A 40926 factors A and B are mainly transformation products of antibiotic A 40926 factor PA and factor PB respectively, and are often already present in the fermentation broth.

It has been found that antibiotic A 40926 factor PA can be transformed into antibiotic A 40926 factor A and antibiotic A 40926 factor PB can be transformed into antibiotic A 40926 factor B under basic conditions.

As a consequence, when the fermentation broth, on an antibiotic A 40926 containing extract or concentrate thereof, is allowed to stand for a certain time under basic conditions (e.g. aqueous solution of a nucleophilic base, at a pH<9 overnight,) an antibiotic A 40926 complex will be obtained which is enriched in antibiotic A 40926 factor A and factor B.

In the present description and claims "antibiotic A 40926 N-acylaminoglucuronyl aglycons" refers to antibiotic A 40926 N-acylaminoglucuronyl aglycon complex AB and/or single factor thereof, i.e. antibiotic A 40926 N-acylaminoglucuronyl aglycon factor A, antibiotic A 40926 N-acylaminoglucurnonyl aglycon factor B, antibiotic A 40926 N-acylaminoglucuronyl aglycon factor $B_0$ and antibiotic A 40926 N-acylaminoglucuronyl aglycon factor $B_1$.

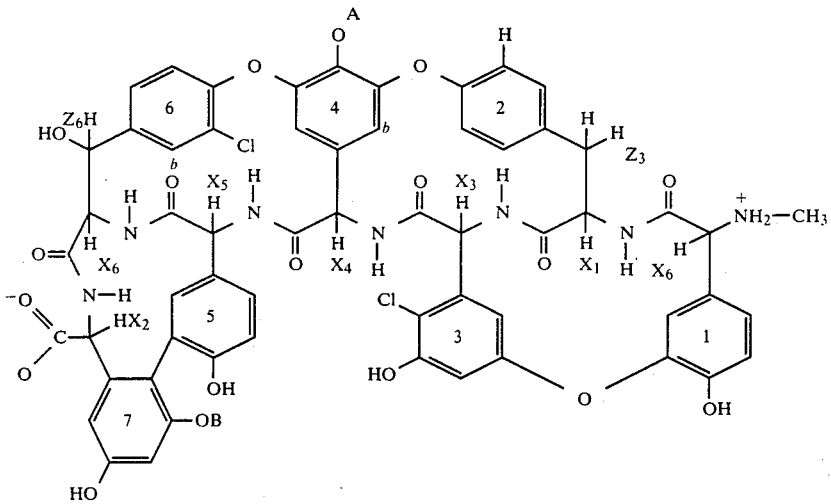

wherein

A represents a N-($C_{11}$–$C_{12}$)acylaminoglucuronyl group and

B represents a mannosyl or acetylmannosyl group.

More particularly, antibiotic A 40926 factor A is the compound of the above formula wherein A represents undecanoylaminoglucuronyl and B represents mannosyl, antibiotic A 40926 factor $B_0$ is the compound of the above formula wherein A represents isododecanoylaminoglucuronyl and B represents mannosyl and antibiotic A 40926 factor $B_1$ is the compound of the above formula I wherein A represents Antibiotic A 40926 N-acylaminoglucuronyl aglycon complex AB (in the non-addition salt form) has the following characteristics:

(A) ultraviolet absorption spectrum, which is shown in FIG. 1 of the accompanying drawings, and exhibits the following absorption maxima:

| | λ max (nm) |
|---|---|
| (a) 0.1 N HCl | 282 |

| | λ max (nm) |
|---|---|
| (b) phosphate buffer pH 7.4 | 282 |
| | 310 (shoulder) |
| (c) 0.1 N KOH | 302 |

Figure 2:
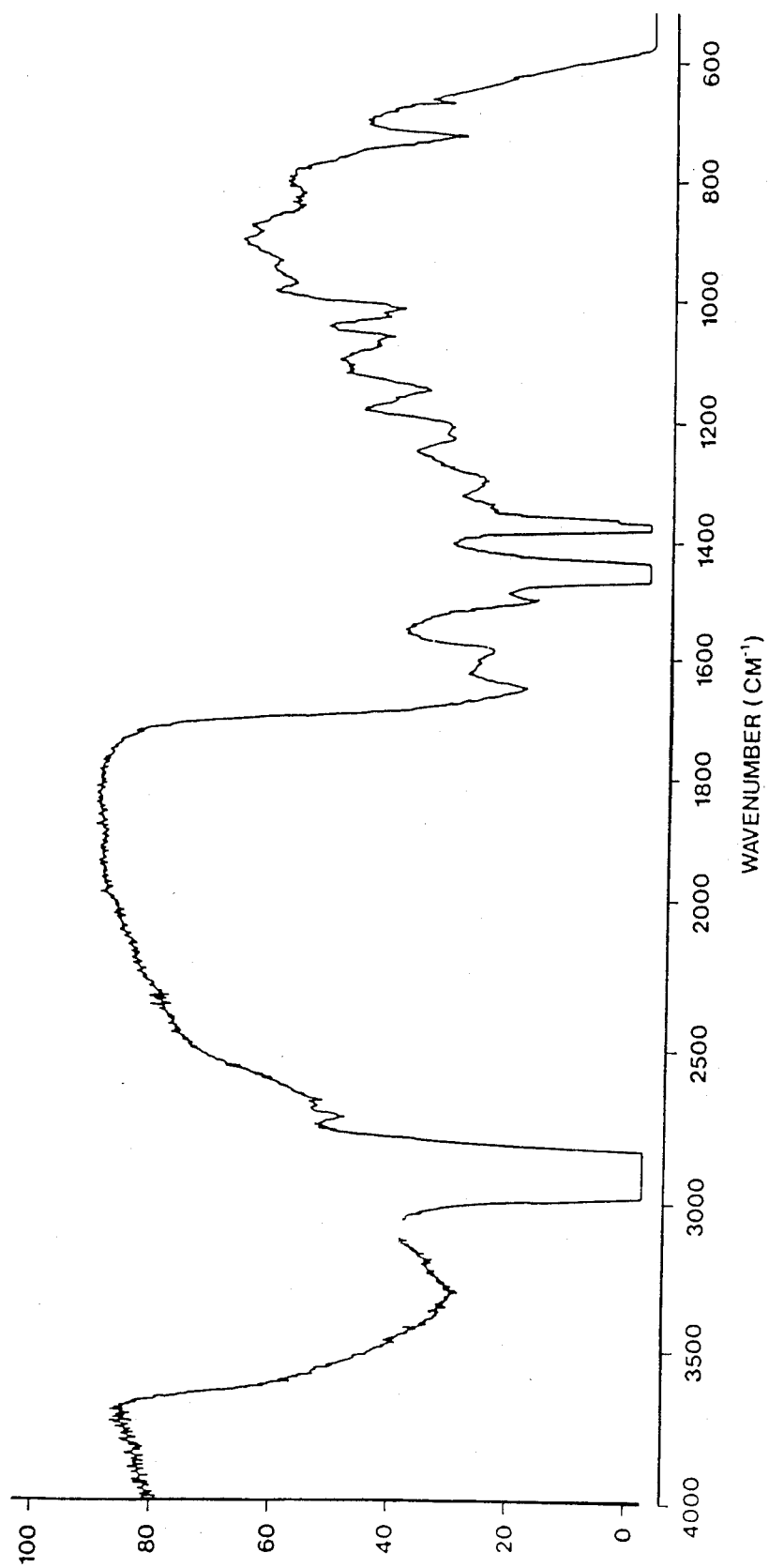

(B) infrared absorption spectrum which is shown in FIG. 2 of the accompanying drawings and exhibits the following absorption maxima (cm$^{-1}$): 3700–3100; 3000–2800 (nujol); 1650; 1620–1550; 1500; 1460 (nujol); 1375 (nujol); 1300; 1250–1180; 1150; 1060; 1010; 970; 930; 840, 820

Figure 3:
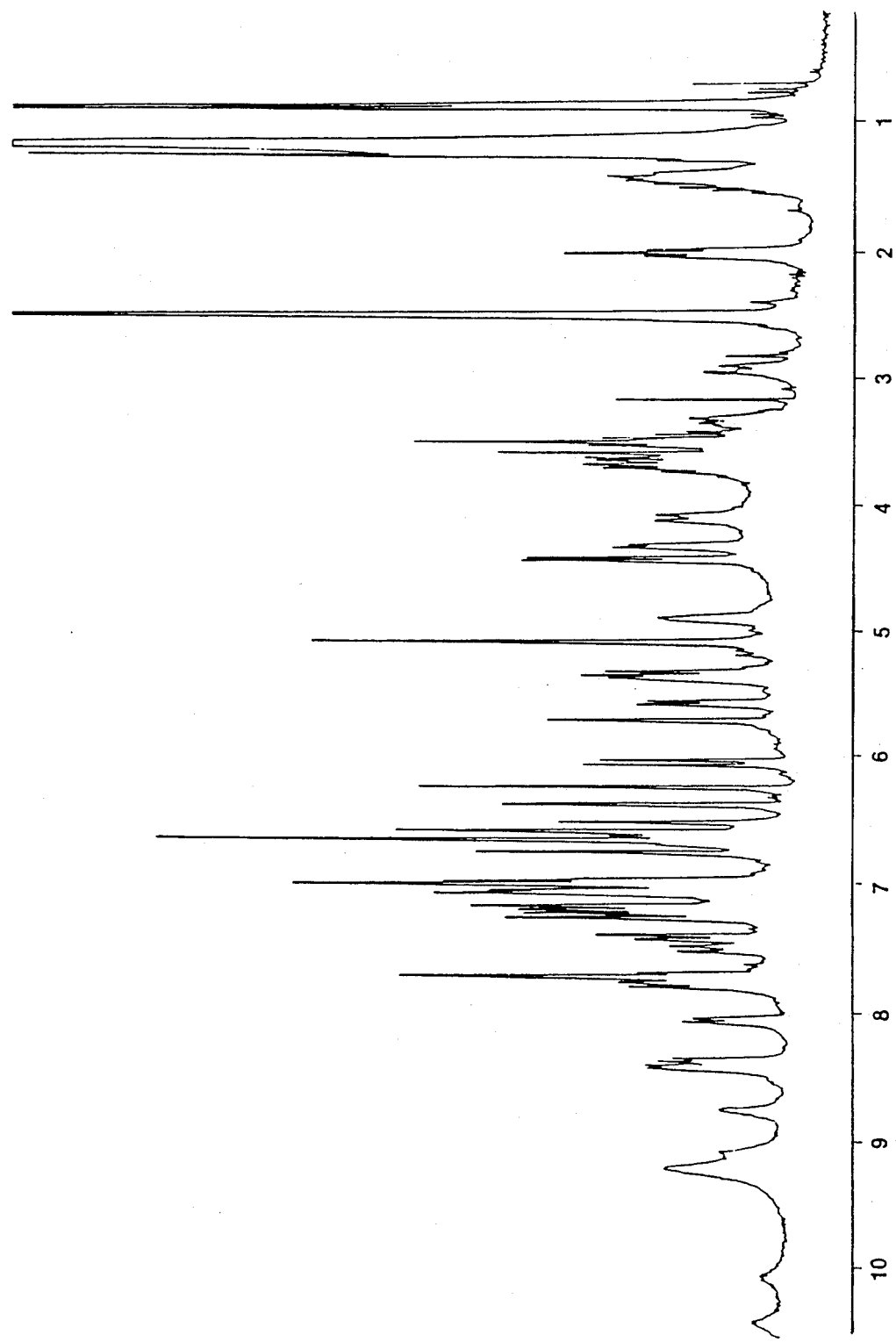

(C) $^1$H-NMR spectrum which is shown in FIG. 3 of the accompanying drawings and exhibits the following groups of signals (in ppm) at 270 MHz recorded in DMSO d$_6$ (hexadeuterodimethylsulfoxide) plus CF$_3$COOH using TMS as the internal standard (0.00 ppm), (δ=ppm):

0.84, d and t [isopropylic CH$_3$'s and terminal CH$_3$]; 1.14, m [(CH$_2$)$_n$]; 1.44, m [—CH$_2$—C-CO and isopropylic CH]; 2.00, t [—CH$_2$—(CO)]; 2.5 s (DMSOd$_5$); 2.5 s (N-CH$_3$); 2.93, m [CH, (Z2)]; 3.33, m [CH, (Z'2)]; 3.20–3.80, m [sugar CH's]; 5.34, d [anomeric proton of acylaminoglucuronic acid]; 4.10 m (X6); 4.33 d, (X5); 4.43 d (X7); 4.9 m (X2); 5.1 (4F and Z6); 5.4 s (X1); 5.58 d (X4); 5.7 s (4B); 6.06 d (X3); 7.73 s (6B); 6.26–8.42 s and m [aromatic CH's and peptidic NH's]; 8.70–10.5, br s [phenolic OH's and NH$_2$+]

br=broad
d=doublet
m=multiplet
s=singlet
t=triplet (D) Retention times (R$_t$) of 1.20 and 1.30 relative to Teicoplanin A$_2$component 2 (R$_t$=20.3 min) when analyzed by reverse phase HPLC under the following conditions:

column: Ultrasphere ODS (5 μm) Altex (Beckman) 4.6 mm (i.d.)×250 mm
pre-column: Brownless Labs RP 18 (5 μm)

| eluent A: | CH$_3$CN | 10% | adjusted at |
|---|---|---|---|
| | (2.5 g/l) NaH$_2$PO$_4$.H$_2$O | 90% | pH 6.0 |
| eluent B: | CH$_3$CN | 70% | adjusted at |
| | (2.5 g/l) NaH$_2$PO$_4$.H$_2$O | 30% | pH 6.0 | elution: linear gradient from 5% to 60% of eluent B in eluent A, in 40 min
flow rate: 1.8 ml/min
U.V. detector: 254 nm
internal standard: Teicoplanin A$_2$ component 2 (Gruppo Lepetit S.p.A.)
(E) acid functions capable of forming salts
(F) amino function capable of forming salts
(G) no mannose unit linked to the core moiety.

Antibiotic A 40926 N-acylaminoglucuronyl aglycon factor A (in the non-addition salt form) has the following characteristics:

(A) ultraviolet absorption spectrum, which exhibits the following absorption maxima:

| | λ max (nm) |
|---|---|
| (a) 0.1 N HCl | 282 |
| (b) phosphate buffer pH 7.4 | 282 |
| | 310 (shoulder) |
| (c) 0.1 N KOH | 302 |

Figure 4:
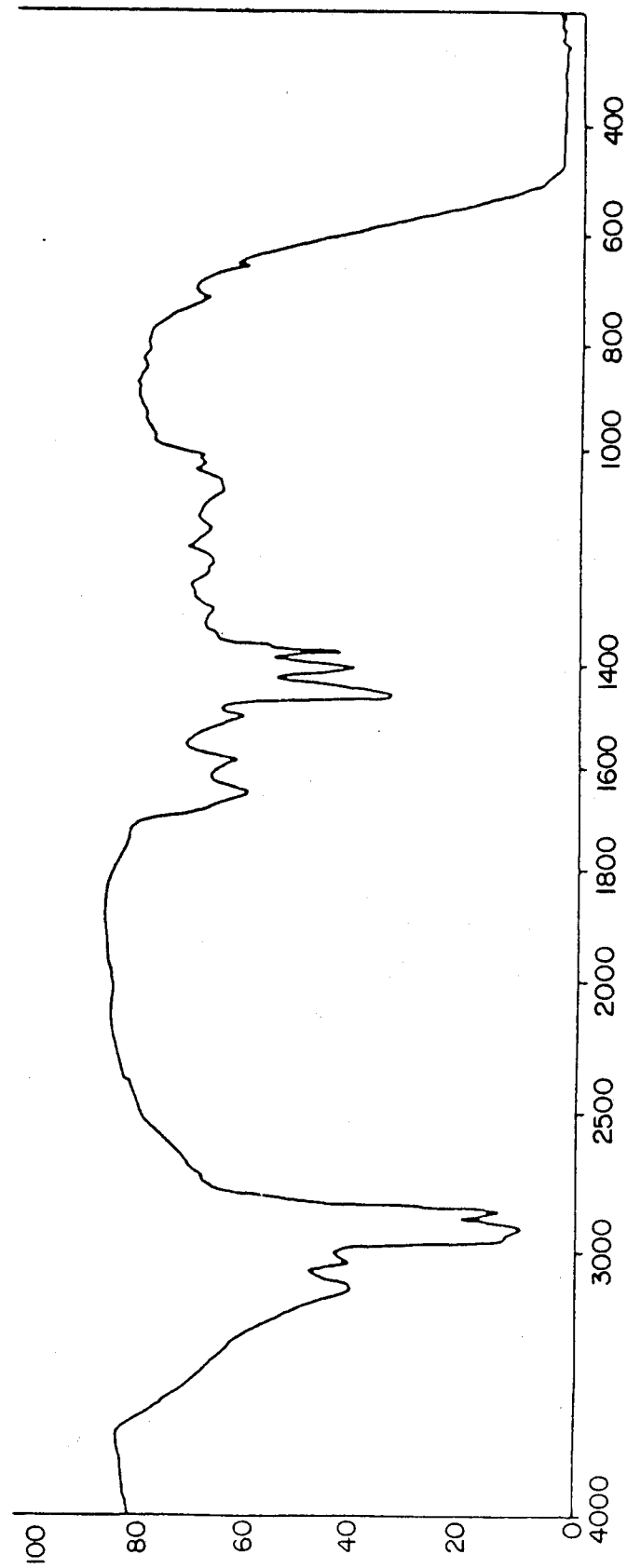

(B) infrared absorption spectrum which is shown in FIG. 4 of the accompanying drawings and exhibits the following absorption maxima (cm$^{-1}$): 3700–3000; 3000–2800; 1650; 1585; 1505; 1460 (nujol); 1375 (nujol); 1295; 1230; 1210; 1150; 1070; 1060; 1010; 845; 820; 720 (nujol)

Figure 5:
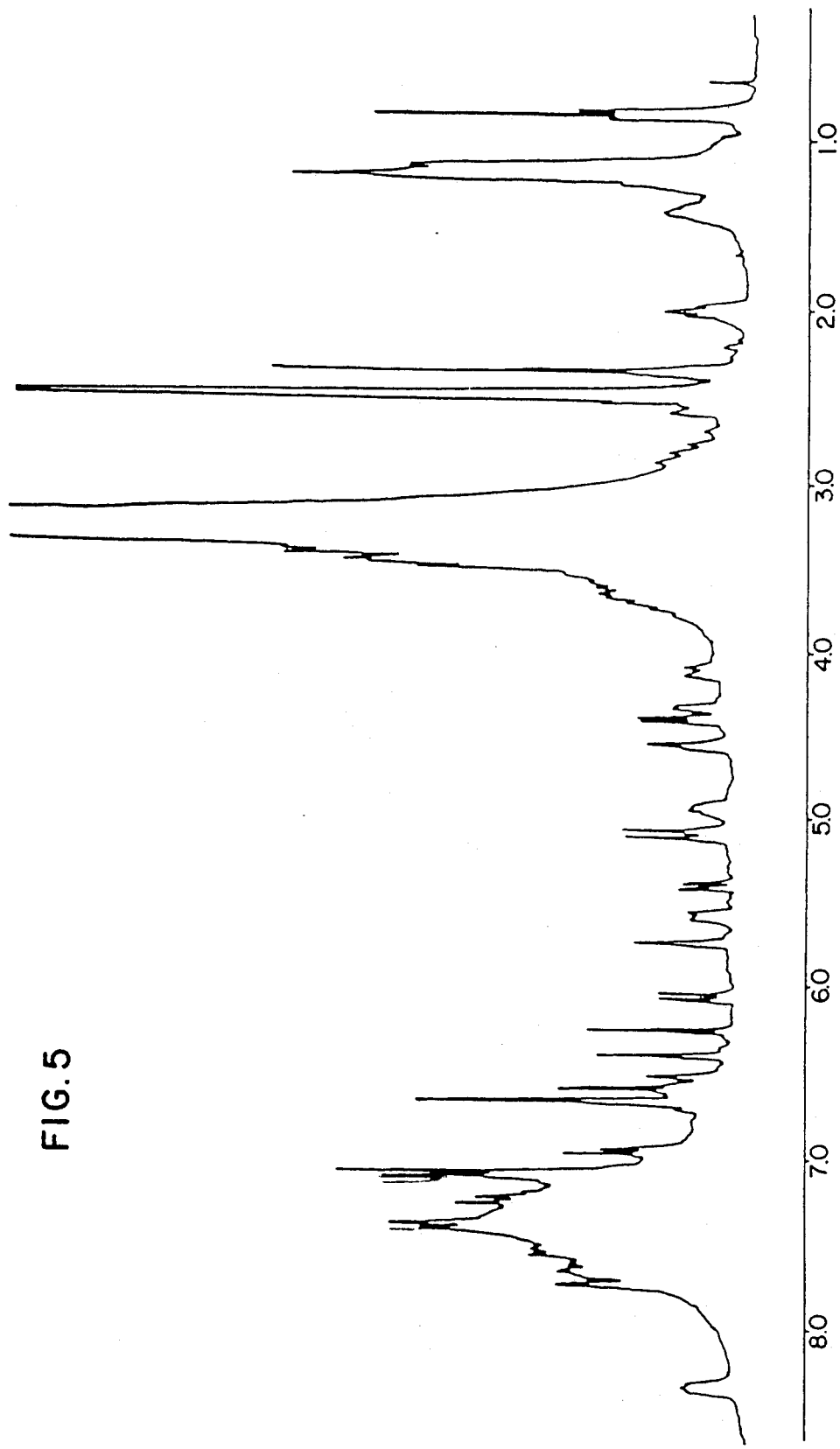

(C) $^1$H-NMR spectrum which is shown in FIG. 5 of the accompanying drawings and exhibits the following groups of signals (in ppm) at 270 MHz recorded in DMSO d$_6$ (hexadeuterodimethylsulfoxide) using TMS as the internal standard (0.00 ppm), (δ=ppm): 0.85 t (terminal CH$_3$); 1.0÷1.3 (aliphatic CH$_2$'s); 1.42 m ((OC-C)CH$_2$); 2.00 t ((CO)CH$_2$); 2.35 s (NCH$_3$); 2.49 s (DMSOd$_5$); 2.82 m (Z2); 2.8÷3.8 (sugar protons and Z'2); 4.12 m (X6); 4.56 s (X1); 4.34 d (X5); 4.41 d (X7); 4.96 m (X2); 5.08–5.12 (4F and Z6); 5.40 d (anomeric proton of acylaminoglucuronic acid); 5.58 d (X4); 5.74 s (4B); 6.05 d (X3); 7.75 s (6B); 6.25–8.40 s, d and m (aromatic CH's and peptidic NH's)

(D) Retention time (R$_t$) of 1.20 relative to Teicoplanin A$_2$ component 2 (R$_t$=20.3 min) when analyzed by reverse phase HPLC under the following conditions:

column: Ultrasphere ODS (5 μm) Altex (Beckman) 4.6 mm (i.d.)×250 mm
pre-column: Brownlee Labs RP 18 (5 μm)

| eluent A: | CH$_3$CN | 10% | adjusted at |
|---|---|---|---|
| | (2.5 g/l) NaH$_2$PO$_4$.H$_2$O | 90% | pH 6.0 |
| eluent B: | CH$_3$CN | 70% | adjusted at |
| | (2.5 g/l) NaH$_2$PO$_4$.H$_2$O | 30% | pH 6.0 | elution: linear gradient from 5% to 60% of eluent B in eluent A, in 40 min
flow rate: 1.8 ml/min
U.V. detector: 254 nm
internal standard: Teicoplanin A$_2$ component 2 (Gruppo Lepetit S.p.A.)
(E) Molecular weight of about 1554 as determined by FAB-MS
(F) acid functions capable of forming salts
(G) amino function capable of forming salts
(H) no mannose unit linked to the core moiety.

Antibiotic A 40926 N-acylaminoglucuronyl aglycon factor B$_0$ (in the non-addition salt form) has the following characteristics:

(A) ultraviolet absorption spectrum, which exhibits the following absorption maxima;

| | λ max (nm) |
|---|---|
| (a) 0.1 N HCl | 282 |
| (b) phosphate buffer pH 7.4 | 282 |
| | 310 (shoulder) |
| (c) 0.1 N KOH | 302 |

Figure 6:
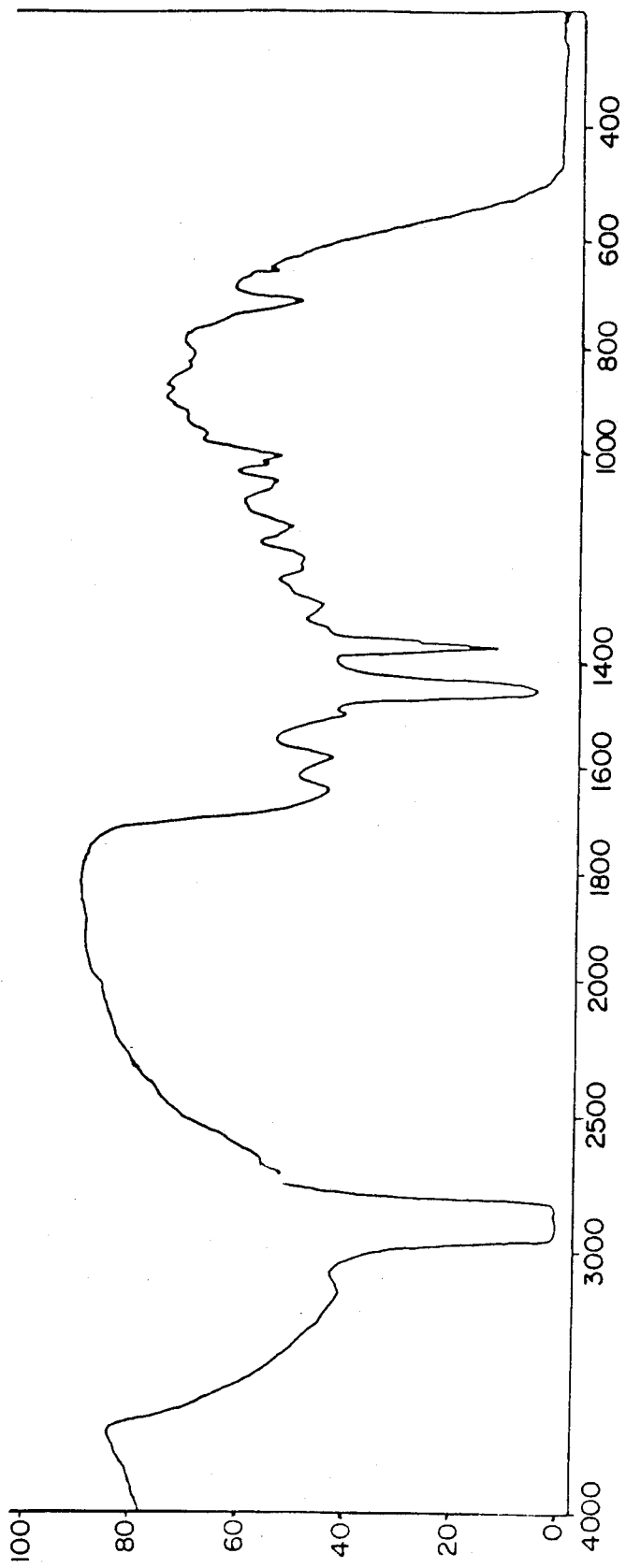

(B) infrared absorption spectrum which is shown in FIG. 6 of the accompanying drawings and exhibits the following absorption maxima (cm$^{-1}$): 3700–3100;

3000–2800 (nujol); 1650; 1585; 1505; 1460 (nujol); 1375 (nujol); 1295; 1230; 1210; 1150; 1060; 1010; 980; 840; 820; 720 (nujol)

Figure 7:
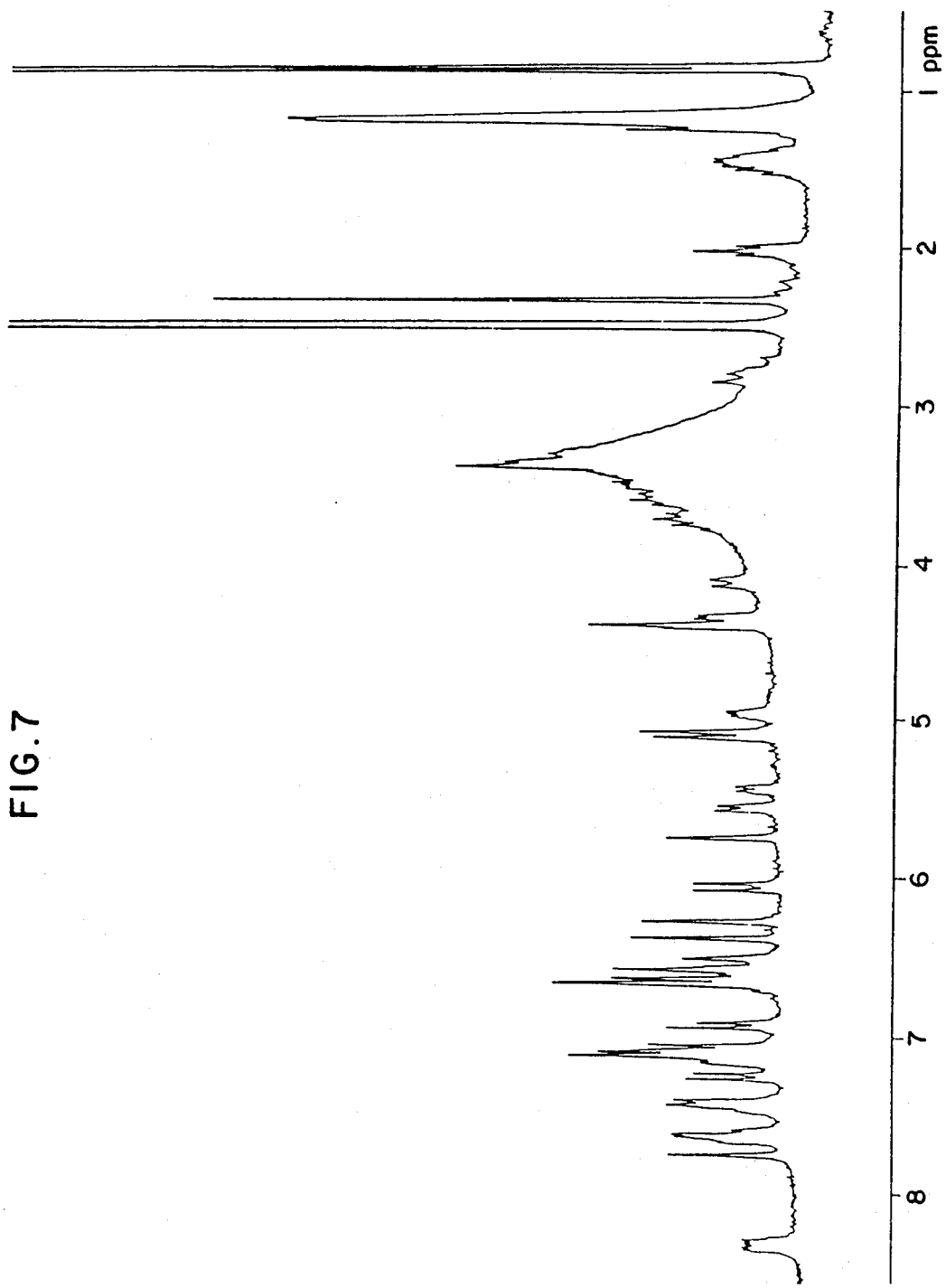

(C) $^1$H-NMR spectrum which is shown in FIG. 7 of the accompanying drawings and exhibits the following groups of signals (in ppm) at 270 MHz recorded in DMSO d$_6$ (hexadeuterodimethylsulfoxide) using TMS as the internal standard (0.00 ppm), (δ=ppm): 0.84, d (isopropylic CH$_3$'s); 1.0÷1.3 (aliphatic CH$_2$'s); 1.3÷1.6 ((OC-C)-CH$_2$ and isopropylic —CH); 2.00 t ((OC)CH$_2$); 2.32 s (NCH$_3$); 2.49 s (DMSOd$_5$); 2.82 m (Z2); 2.9÷3.8 (sugar protons); 4.12 m (X6); 4.44 s (X1); 4.33 d (X5); 4.37 d (X7); 4.95 m (X2); 5.06÷5.10 (4F and Z6); 5.38 d (anomeric proton of acylaminoglucuronic acid); 5.59 d (X4); 5.72 s (4B); 6.05 d (X3); 7.74 s (6B); 6.27÷8.5 (aromatic and peptidic NH's)

(D) Retention time (R$_t$) of 1.30 relative to Teicoplanin A$_2$ component 2 (R$_t$=20.3 min) when analyzed by reverse phase HPLC under the following conditions:

column: Ultrasphere ODS (5 μm) Altex (Beckman) 4.6 mm (i.d.)×250 mm
pre-column: Brownlee Labs RP 18 (5 μm)

| eluent A: | CH$_3$CN | 10% | adjusted at |
| --- | --- | --- | --- |
|  | (2.5 g/l) NaH$_2$PO$_4$.H$_2$O | 90% | pH 6.0 |
| eluent B: | CH$_3$CN | 70% | adjusted at |
|  | (2.5 g/l) NaH$_2$PO$_4$.H$_2$O | 30% | pH 6.0 | elution: linear gradient from 5% to 60% of eluent B in eluent A, in 40 min
flow rate: 1.8 ml/min
U.V. detector: 254 nm
internal standard: Teicoplanin A$_2$ component 2 (Gruppo Lepetit S.p.A.)

(E) Molecular weight of about 1568 as determined by FAB-MS (F) acid functions capable of forming salts
(G) amino function capable of forming salts
(H) no mannose unit linked to the core moiety.

Antibiotic A 40926 N-acylaminoglucuronyl aglycon factor B$_1$ has molecular weight of about 1568 as determined by FAB-MS and substantially the same physico-chemical characteristics reported above for antibiotic A 40926 N-acylaminoglucuronyl aglycon factor B$_0$ except that it has a triplet at 0.84 δ ppm attributable to the methyl group of an n-propyl function in the NMR system reported above and a retention time relative to Teicoplanin A$_2$ component 2 of 1.32 in the system reported above.

Figure 8:
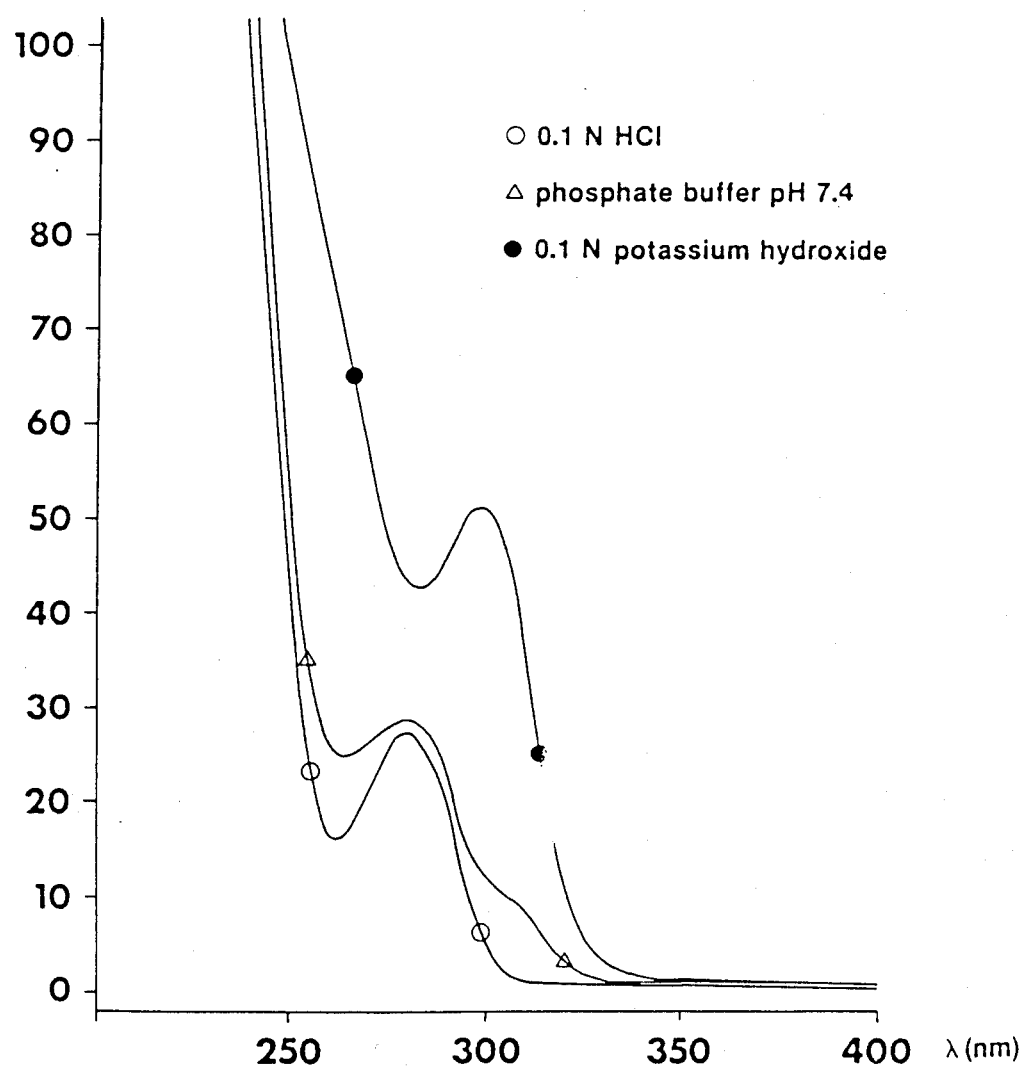

Antibiotic A 40926 aglycon has the following characteristics:

(A) ultraviolet absorption spectrum, which is shown in FIG. 8 of the accompanying drawings and exhibits the following absorption maxima:

|  | λ max (nm) |
| --- | --- |
| (a) 0.1 N HCl | 280 |
| (b) phosphate buffer pH 7.4 | 280 |
|  | 310 (shoulder) |
| (c) 0.1 N KOH | 299 |

Figure 9:
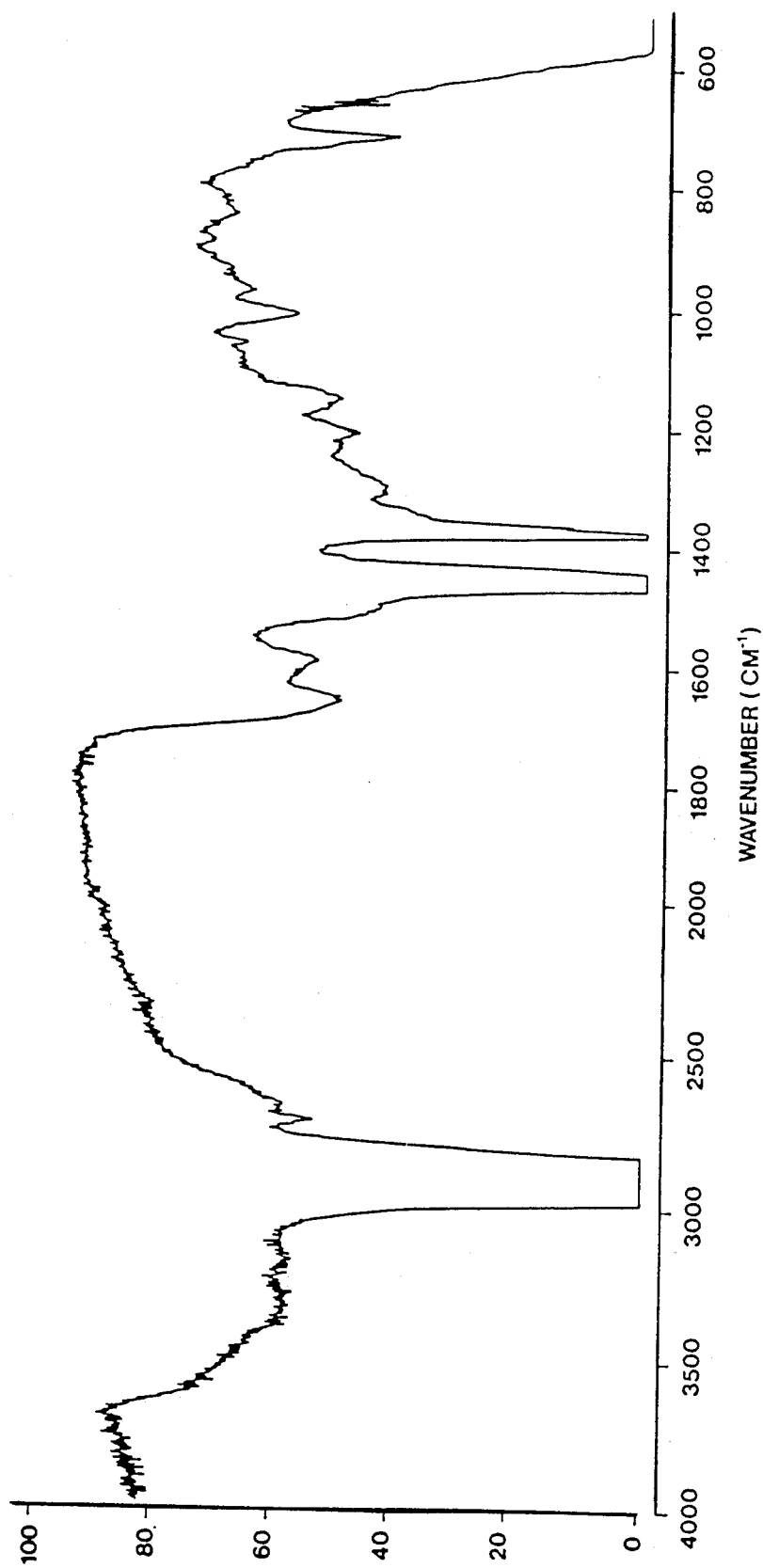

(B) infrared absorption spectrum which is shown in FIG. 9 of the accompanying drawings and exhibits the following absorption maxima (cm$^{-1}$): 3700–3100; 3000–2800 (nujol); 1655; 1620–1550; 1500; 1460 (nujol); 1375 (nujol); 1300; 1205; 1145; 1010; 970; 930; 840

Figure 10:
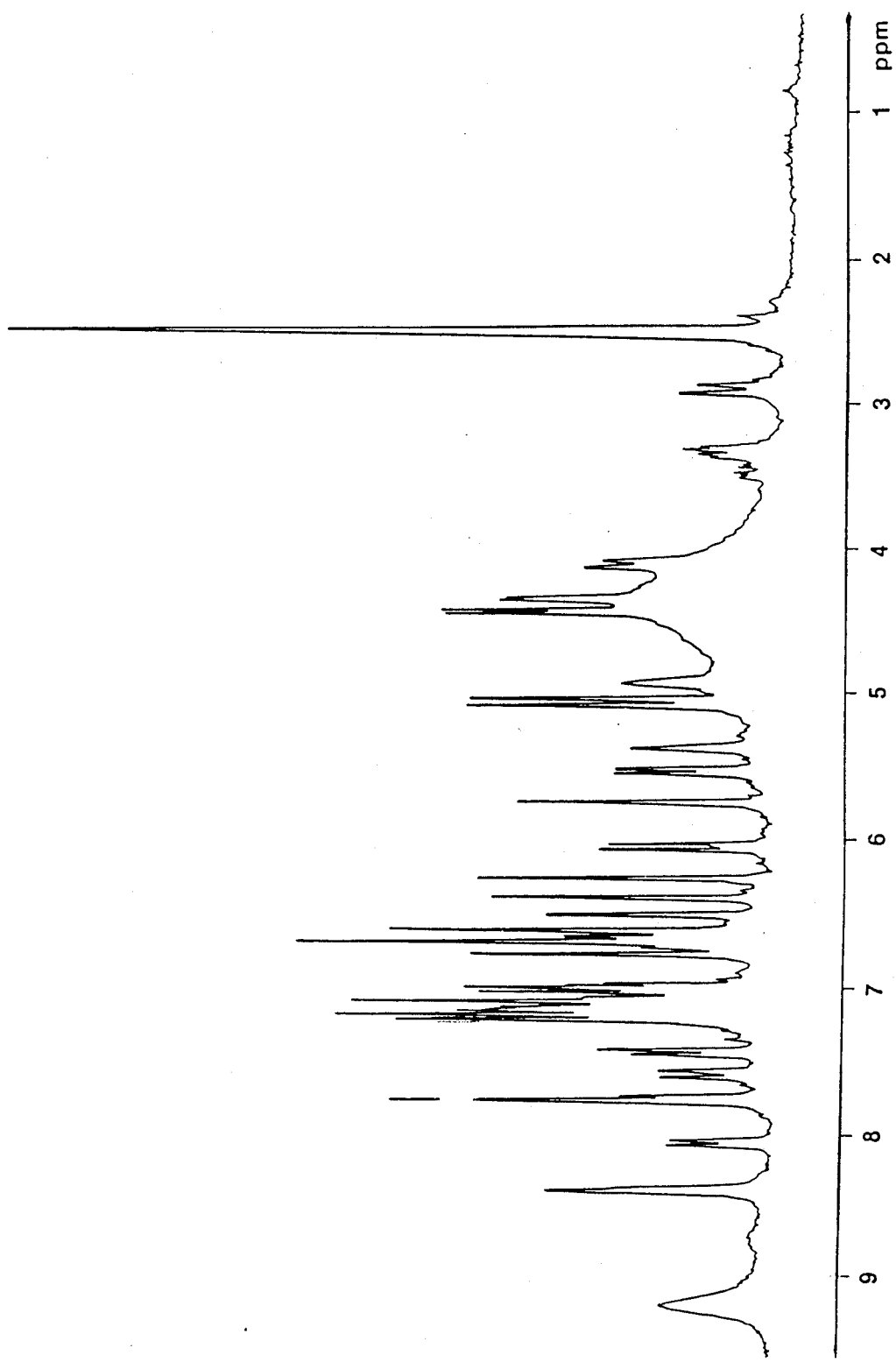

(C) $^1$H-NMR spectrum which is shown in FIG. 10 of the accompanying drawings and has the following groups of signals (in ppm) at 270 MHz recorded in DMSO d$_6$ (hexadeuterodimethylsulfoxide) plus CF$_3$COOH using TMS as the internal standard (0.00 ppm), (δ=ppm): 2.51 s (DMSOd$_5$); 2.50 s (NCH$_3$); 2.88 m (Z2); 3.33 m (Z'2); 4.10 m (X6); 4.34 d (X5); 4.43 d (X7); 4.93 m (X2); 5.04 s (4F); 5.09 s (Z6); 5.54 d (X4); 5.75 s (4B); 6.05 d (X3); 7.76 s (6B); 6.3–8.4 (aromatic and peptidic (NH's)

(D) Retention time (R$_t$) of 0.59 relative to Teicoplanin A$_2$ component 2 (R$_t$=20.3 min) when analyzed by reverse phase HPLC under the following conditions:

column: Ultrasphere ODS (5 μm) Altex (Beckman) 4.6 mm (i.d.)×250 mm
pre-column: Brownlee Labs RP 18 (5 μm)

| eluent A: | CH$_3$CN | 10% | adjusted at |
| --- | --- | --- | --- |
|  | (2.5 g/l) NaH$_2$PO$_4$.H$_2$O | 90% | pH 6.0 |
| eluent B: | CH$_3$CN | 70% | adjusted at |
|  | (2.5 g/l) NaH$_2$PO$_4$.H$_2$O | 30% | pH 6.0 | elution: linear gradient from 5% to 60% of eluent B in eluent A, in 40 min
flow rate: 1.8 ml/min
U.V. detector: 254 nm
internal standard: Teicoplanin A$_2$ component 2 (Gruppo Lepetit S.p.A.)

Under the same conditions the retention time relative to antibiotic L 17054 (Gruppo Lepetit, EP-A- No. 119575) is 1.42

(E) Molecular weight of about 1211 as determined by FAB-MS (F) acid functions capable of forming salts
(G) amino function capable of forming salts
(H) no mannose unit linked to the core moiety.

On the basis of the physico-chemical characteristics and by reference to the structure of known antibiotic substances of the same class, the above formula I wherein A represents N-(C$_{11}$–C$_{12}$)acylaminoglucuronyl and B represents hydrogen can be attributed to antibiotic A 40926 N-acylaminoglucuronyl aglycons.

More particularly, the above formula I wherein A represents n-undecanoylaminoglucuronyl and B represents hydrogen can be attributed to antibiotic A 40926 N-acylaminoglucuronyl aglycon factor A, the above formula I wherein A represents isododecanoylaminoglucuronyl and B represents hydrogen can be attributed to antibiotic A 40926 N-acylaminoglucuronyl aglycon factor B$_0$, the above formula I wherein A represents n-dodecanoylaminoglucuronyl and B represents hydrogen can be attributed to antibiotic A 40926 N-acylaminoglucuronyl aglycon factor B$_1$. This latter is obtained according to the process of the invention from antibiotic A 40926 factor B$_1$ which is the component of antibiotic A 40926 factor B having R$_t$ equal to 1.27 relative to Teicoplanin A$_2$ component 2 in the reverse phase system described in EP-A No. 177882 and reported below. It is obtained from antibiotic A 40926 factor B after separation of factor B$_0$ (the major factor).

The above formula I, wherein A and B represent hydrogen, can be attributed to antibiotic A 40926 aglycon.

In the present description and claims, when dealing with antibiotic A 40926 N-acylaminoglucuronyl aglycon complex or factors thereof or antibiotic A 40926 aglycon, it is intended to encompass the "internal salt" form as well as the possible acid and basic addition salts. (inoculated with a multipoint inoculator) for agar dilution MICs (*C. difficile, P. acnes, B. fragilis*).

The minimal inhibitory concentrations (MIC, µg/ml) for some microorganisms are reported below in Table I.

TABLE I

| Strain | M.I.C. (µg/ml) | |
|---|---|---|
| | Antibiotic A 40926 N—acylaminoglucuronyl aglycon complex AB | Antibiotic A 40926 aglycon |
| *Staph. aureus* L165 | 0.13 | 0.13 |
| *Staph. aureus* L165 ($10^6$ cfu/ml) | 0.13 | 0.25 |
| *Staph. epidermidis* L147 ATCC 12228 (coagulase negative) | 0.13 | 0.13 |
| *Strep. pyogenes* L49 C203 | 0.06 | 0.5 |
| *Strep. pneumoniae* L44 UC41 | 0.13 | 1 |
| *Strep. faecalis* L149 ATCC 7080 | 0.13 | 0.5 |
| *Strep. mitis* L796 (clinical isolate) | 0.06 | 0.5 |
| *Clostridium perfringens* L290 ISS 30543 | | 0.25 |
| *Clostridium difficile* L1363 ATCC 9689 | 0.25 | 1 |
| *Propionibacterium acnes* L1014 ATCC 6919 | 0.06 | 1 |
| *Bacteroides fragilis* L1010 ATCC 23745 | 16 | 32 |
| *Neisseria gonorrhoeae* L997 ISM68/126 | 4 | 16 |
| *Haemophilus influenzae* L 970 type b ATCC 19418 | | 32 |
| *Escherichia coli* L47 SKF 12140 | >128 | 128 |
| *Mycoplasma gallisepticum* L431 S6 Weybridge | 64 | >128 |

| Strain | M.I.C. (µg/ml) | |
|---|---|---|
| | Antibiotic A 40926 N—acylaminoglucuronyl aglycon factor A | Antibiotic A 40926 N—acylaminoglucuronyl aglycon factor B, $B_0$ and $B_1$ |
| *Staph. aureus* L165 | 0.06 | 0.06 |
| *Staph. aureus* L165 ($10^6$ cfu/ml) | 0.13 | 0.13 |
| *Staph. haemolyticus* L602 (coagulase negative) | 0.25 | 0.25 |
| *Staph. epidermidis* L147 ATCC 12228 (coagulase negative) | 0.06 | 0.06 |
| *Strep. pyogenes* L49 C203 | 0.06 | 0.06 |
| *Strep. pneumoniae* L44 UC41 | 0.06 | 0.06 |
| *Strep. faecalis* L149 ATCC 7080 | 0.13 | 0.13 |
| *Strep. mitis* L796 clin. isolate | 0.06 | 0.06 |
| *Clostridium perfringens* L290 ISS 30543 | 0.03 | 0.03 |
| *Neisseria gonorrhoeae* L997 ISM68/126 | 8 | 8 |
| *Haemophilus influenzae* L 970 type b ATCC 19418 | 32 | 32 |
| *Escherichia coli* L47 SKF 12140 | >128 | >128 |
| *Ureaplasma urealyticum* L 1479 clin. isolate | >128 | >128 |

The antibacterial activity of the compounds of the invention can be demonstrated in vitro by means of standard dilution tests on different microorganism cultures.

Culture media and growth conditions for MIC (minimal inhibitory concentration) determinations were as follows: Isosensitest broth (Oxoid), 24 h, for staphylococci, *Strep. faecalis* and Gram-negative bacteria (*Escherichia coli*); Todd-Hewitt broth (Difco), 24 h for other streptococcal species; GC base broth (Difco) +1% Isovitalex (BBL), 48 h, $CO_2$-enriched atmosphere for *Neisseria gonorrhoeae;* Brain Heart broth (Difco) +1% Supplement C (Difco), 48 h for *Haemophilus influenzae;* AC broth (Difco), 24 h, anaerobic atmosphere for *Clostridium perfringens;* Wilkins-Chalgren agar (ref: T. D. Wilkins & S. Chalgren, 1976, Antimicrob. Ag. Chemother. 10, 926), 48 h, anaerobic atmosphere for the other anaerobics (*C. difficile, Propionibacterium acnes, Bacteroides fragilis*); PPLO broth (Difco)+10% horse serum +1% glucose, 48 h for *Mycoplasma gallisepticum;* PPLO broth with supplements as in R. T. Evans and D. Taylor-Robinson (J. Antimicrob. Chemother. 4, 57), 24 h for *U. urealyticum*. Incubation was at 37° C. Inocula were as follows: 1% (v/v) of a 48 h broth culture for *M. gallisepticum;* about $10^4$ color-changing units/ml for *U. urealyticum;* about $10^4$–$10^5$ colony-forming units/ml for other broth dilution MICs; about $10^4$–$10^5$ bacteria/spot Antibiotic A 40926 N-acylaminoglucuronyl aglycon complex AB and the factors thereof have been found particularly active against coagulase negative staphylococci. The M.I.C. (µg/ml) relative to a series of clinical isolates of *S. epidermidis* and *S. haemolyticus* are reported below:

TABLE II

| Strain | Antibiotic A 40926 N—acylaminoglucuronyl aglycon complex AB M.I.C. (µg/ml) |
|---|---|
| *S. epidermidis* L 393 | 0.06 |
| *S. epidermidis* L 408 | 0.13 |
| *S. epidermidis* L 410 | 0.06 |
| *S. haemolyticus* L 381 | 0.25 |
| *S. haemolyticus* L 382 | 0.13 |
| *S. haemolyticus* L 383 | 0.5 |
| *S. haemolyticus* L 403 | 0.25 |

Moreover, the $M.I.C._{90}$ (µg/ml) of antibiotic A 40926 N-acylaminoglucuronyl aglycon complex AB, i.e. the concentration inhibiting at least 90% of 36 treated clinical isolates of coagulase negative staphylococci, has been found to be 0.5 µg/ml.

The antimicrobial activity of the compounds of the invention is confirmed also in experimental septicemia in the mouse.

Control and treatment groups contained ten CD-1 mice (Charles River) weighing 18–22 g. They were infected intraperitoneally with 0.5 ml of bacterial suspension prepared by diluting an overnight culture of *S. pyogenes* C 203 (L 49) with sterile peptonized saline. Inocula were adjusted so that untreated animals died of septicemia within 48 h. The compounds to be tested were administered subcutaneously immediately after infection. On the 7th day, the $ED_{50}$ in mg/kg was calculated by the method of Spearman and Kärber (D. J. Finney "Statistical Methods in Biological Assay", Griffin, page 524, 1952) from the percentage of surviving animals at each dose.

Under these conditions the $ED_{50}$ values of antibiotic A 40926 N-acylaminoglucuronyl aglycon complex AB and antibiotic A 40926 aglycon were respectively 0.54 and 6.2 mg/kg.

Antibiotic A 40926 N-acylaminoglucuronyl aglycon complex AB, the factors thereof and antibiotic A 40926 aglycon possess acid and basic functions and can form salts with organic and inorganic counter ions according to conventional procedures.

Representative and suitable acid addition salts of the compounds of the invention include those salts formed by standard reaction with both organic and inorganic acids such as, for example, hydrochloric, hydrobromic, sulfuric, phosphoric, acetic trifluoroacetic, trichloroacetic, succinic, citric, ascorbic, lactic, maleic, fumaric, palmitic, cholic, pamoic, mucic, glutamic, camphoric, glutaric, glycolic, phthalic, tartaric, lauric, stearic, salicylic, methanesulfonic, benzenesulfonic, sorbic, picric, benzoic, cinnamic and the like acids.

Representative examples of these bases are: alkali metal or alkaline-earth metal hydroxide such sodium, potassium, calcium, magnesium, barium hydroxide; ammonia and aliphatic, alicyclic or aromatic organic amines such as methylamine, dimethylamine, trimethylamine, and picoline.

The transformation of the "non-salt"compounds of the invention into the corresponding addition salts, and the reverse, i.e. the transformation of an addition salt of a compound of the invention into the non-salt form, are within the ordinary technical skill and are encompassed by the present invention.

For instance antibiotic A 40926 N-acylaminoglucuronyl aglycon complex AB and/or factors thereof and antibiotic A 40926 aglycon can be transformed into the corresponding acid or base addition-salt by dissolving the non-salt form in an aqueous solvent and adding a slight molar excess of the selected acid or base. The resulting solution or suspension is then lyophilized to recover the desired salt.

In case the final salt is unsoluble in a solvent where the non-salt form is soluble it is recovered by filtration from the organic solution of the non-salt form after addition of the stoichometric amount or a slight molar excess of the selected acid or base.

Examples of these unsoluble salts are calcium, magnesium and barium salts.

The non-salt form can be prepared from a corresponding acid or base salt dissolved in an aqueous solvent which is then neutralized to free the non-salt form.

When following the neutralization the elimination of the excess of acid or base is necessary, a common desalting procedure may be employed.

For example, column chromatography on silanized silica gel, non-functionalized polystyrene, acrylic and controlled pore polydextrane resins (such as Sephadex LH 20) or activated carbon may be conveniently used. After eluting the undesired salts with an aqueous solution, the desired product is eluted by means of a linear gradient or a step-gradient of a mixture of water and a polar or apolar organic solvent, such as acetonitrile/water from 50:50 to about 100% acetonitrile.

As it is known in the art, the salt formation either with pharmaceutically acceptable acids (or bases) or non-pharmaceutically acceptable acids (or bases) may be used as a convenient purification technique. After formation and isolation, the salt form of an A 40926 antibiotic can be transformed into the corresponding non-salt form or into a pharmaceutically acceptable salt form.

In some instances, a base addition salt of antibiotic A 40926 N-acylaminoglucuronyl aglycon complex AB, of a factor thereof and of antibiotic A 40926 aglycon is more soluble in water and hydrophilic solvents.

Preparation of antibiotic A 40926 N-acylaminoglucuronyl aglycons and antibiotic A 40926 aglycon Antibiotic A 40926 N-acylaminoglucuronyl aglycon complex AB, N-acylaminoglucuronyl aglycon factor A, N-acylaminoglucuronyl aglycon factor B, antibiotic A 40926 N-acylaminoglucuronyl aglycon factor $B_0$, antibiotic A 40926 N-acylaminoglucuronyl aglycon factor $B_1$ and antibiotic A 40926 aglycon are prepared from antibiotic A 40926 complex or a single factor or mixture of said factors in any proportion, i.e. A 40926 factor A, A 40926 factor B, A 40926 factor PA, A 40926 factor PB, A 40926 factor $B_0$ and A 40926 factor $B_1$, by controlled acid hydrolysis.

Generally, this hydrolysis is conducted in the presence of a strong acid in a suitable organic solvent. The reaction temperature may vary considerably; preferably it is between 4° C. and 100° C. and most preferably between 25° C. and 80° C.

The reaction time varies depending on the specific reaction conditions.

Generally, the reaction time is between 30 min and 120 h.

However, since the reaction course may be monitored by TLC or HPLC, the skilled man is capable of deciding when the hydrolysis of the starting materials is to be considered as completed and the recovery procedure may be started.

Representative examples of strong acids are mineral or organic strong acids such as hydrogen halides, e.g. hydrogen chloride, bromide and iodide, phosphoric acids, sulfuric acid, haloacetic acids, e.g. trichloroacetic acid, trifluoroacetic acid, chlorodifluoroacetic acid and the like.

Suitable organic solvents are such that:

(a) they may at least partially solubilize the starting materials;

(b) the products, once obtained, either separate or may be separated from them according to usual techniques, and (c) in any case, they do not unfavorably interfere with the reaction course.

Examples of said organic solvents are protic or aprotic solvents such as ($C_1$–$C_4$)alkyl sulfoxides, e.g. dimethylsulfoxide and diethylsulfoxide, ($C_1$–$C_4$)alkyl formamides, e.g. dimethylformamide, diethylformamide, dioxane, tetrahydrofuran and similar solvents, which are of course compatible with the selected acid.

In general, the hydrolysis is conducted in the presence of a limited amount of water, e.g. from 0.1 to 10% (w/w) of the reaction mixture. This amount of water can obviously be already present either in the starting materials, solvents and/or reagents, or may be added ad hoc, if necessary.

A preferred embodiment of the process of the invention, is represented by the use of a mixture dimethylsulfoxide/concentrated hydrochloric acid at a temperature between 40° C. and 80° C. Typically, the ratio of the mixture dimethylsulfoxide/concentrated hydrochloric acid is from 8.2 to 9.5:0.5. Preferred concentrated hydrochloric acid is 37% (w/w) hydrochloric acid.

Generally, the reaction product is a mixture of the N-acylaminoglucuronyl aglycons and the aglycon. By controlling the temperature, and in some instances also the concentration and strength of the acid, it is possible to direct the process, at least to a certain extent, to the production of one of the two main products, i.e. antibiotic A 40926 N-acylaminoglucuronyl aglycons or antibiotic A 40926 aglycon. More particularly, by keeping a comparatively low temperature, possibly reducing the strength of the acid mixture and properly controlling the reaction time, the yields in the N-acylaminoglucuronyl aglycons are increased, while at comparatively higher temperatures and longer times the aglycon alone is obtained.

Also in this case, the reaction course is monitored by TLC or preferably HPLC and the reaction may be stopped when the optimal production of the desired substance is obtained in order to maximize the yields of the subsequent recovery process.

When a product is obtained which is a mixtue of antibiotic A 40926 N-acylaminoglucuronyl aglycons and antibiotic A 40926 aglycon it can be separated by chromatography such as liquid/liquid chromatography, flash chromatography, high pressure liquid chromatography and affinity chromatography.

When affinity chromatography is used, a preferred adsorbent is an immobilized D-Alanyl-D-Alanine as described in EP-A 122969. Particularly preferred is agarose-$\epsilon$-aminocaproyl-D-Alanyl-D-Alanine. The elution mixture is a mixture of an aqueous buffer and a saline solution. By adjusting the pH and the salt concentration antibiotic A 40926 N-acylaminoglucuronyl aglycons are separated from antibiotic A 40926 aglycon.

A further object and preferred embodiment of the present invention is a process for prevalently preparing antibiotic A 40926 N-acylaminoglucuronyl aglycon complex AB or a factor thereof which comprises subjecting antibiotic A 40926 complex or a single factor thereof, antibiotic A 40926 complex AB, antibiotic A 40926 factor A, antibiotic A 40926 factor B, antibiotic A 40926 factor $B_0$, antibiotic A 40926 factor $B_1$, antibiotic A 40926 factor PA and antibiotic A 40926 factor PB to controlled acid hydrolysis with a mixture of a polar aprotic solvent and a strong mineral or organic acid in the presence of a limited (0.1-10%, w/w) amount of water at a temperature between room temperature and 100° C. and preferably between 40° C. and 65° C. for a time of from 3 h to 120 h.

Most preferably the hydrolyzing mixture is a mixture of dimethylsulfoxide and 37% hydrochloric acid from 9:1 to 9.5:0.5, the temperature is 65° C. and the reaction time is 5 h.

When the starting material for the preparation of the N-acylaminoglucuronyl aglycon is antibiotic A 40926 complex, a final product is obtained which is still a mixture of factors substantially corresponding to those of the original complex, while when a single factor is used, such as antibiotic A 40926 factor A or factor B, a single N-acylaminoglucuronyl aglycon factor is obtained which is respectively antibiotic A 40926 N-acylaminoglucuronyl aglycon factor A and antibiotic A 40926 N-acylaminoglucuronyl aglycon factor B, $B_0$ or $B_1$.

When an antibiotic A 40926 N-acylaminoglucuronyl aglycon complex AB is obtained, it can be separated into its single factors by known per se techniques such as liquid/liquid chromatography and preferably preparative HPLC.

A preferred procedure includes reverse-phase liquid chromatography, preferably in stainless steel columns under moderate pressure (5-50 bar) or at high pressure (100-200 bar). The solid phase may be a silanized silica gel with a hydrocarbon phase at (2-18) carbon atoms (most preferably C 18) or phenyl group and the eluent is a mixture of a polar water-miscible solvent as defined above and an aqueous buffer at a pH compatible with the resin (preferably pH 4-8).

Most preferred is a linear gradient elution mixture of a polar water soluble aprotic solvent selected from acetonitrile and an aqueous buffer solution at pH between 4 and 8 and preferably about 6, such as a linear gradient from 5% to 45% of a mixture acetonitrile/phosphate buffer, pH 6, 70:30 and a mixture acetonitrile/phosphate buffer, pH 6, 10:90.

Another object and preferred embodiment of the present invention is a process for selectively preparing antibiotic A 40926 aglycon which comprises subjecting antibiotic A 40926 complex, or a single factor thereof, antibiotic A 40926 complex AB, antibiotic A 40926 factor A, antibiotic A 40926 factor B, antibiotic A 40926 factor PA, antibiotic A 40926 factor PB, antibiotic A 40926 factor $B_0$, antibiotic A 40926 factor $B_1$, antibiotic A 40926 mannosyl aglycon and antibiotic A 40926 N-acylaminoglucuronyl aglycon (complex AB/or a single factor thereof) to controlled acid hydrolysis in the presence of: (a) an organic protic solvent selected from aliphatic acids and alpha-halogenated aliphatic acids which at the reaction temperature are liquids, aliphatic and cycloaliphatic alkanols which at the reaction temperature are liquids slightly mixable with water, phenyl substituted lower alkanols wherein the phenyl moiety may optionally carry ($C_1$-$C_4$)alkyl, ($C_1$-$C_4$)alkoxy or halo rests which at the reaction temperature are liquids slightly mixable with water, and beta-polyhalogenated lower alkanols, which at the reaction temperature are liquids, (b) a strong acid compatible with the solvent selected from strong mineral acids, strong organic acids and strong acid cation exchanger resins in the hydrogen form, and (c) at a reaction temperature between about 20° C. and about 100° C.

When the protic solvent is selected from aliphatic acids and alpha-halogenated aliphatic acids, aliphatic acids of 1 to 5 carbon atoms, and alpha-halogenated aliphatic acids of 2 to 5 carbon atoms are respectively preferred, although any aliphatic acid and any alpha-halogenated aliphatic acid which, at the reaction temperature, is capable of dissolving the starting material in a sufficient amount, may be usefully employed.

Examples of the above acids are: formic acid, acetic acid, propionic acid, butyric acid, isobutyric acid, valeric acid, isovaleric acid, trimethylacetic acid, fluoroacetic acid, chloroacetic acid, difluoroacetic acid, dichloroacetic acid, trifluoroacetic acid, trichloroacetic acid, pentafluoropropionic acid, 2,2,3,4,4,4-hexafluorobutyric acid, heptafluorobutyric acid and the like.

Lower aliphatic acids such as acetic acid and propionic acid or lower alpha-halogenated aliphatic acid such as chloroacetic acid, dichloroacetic acid, trichloroacetic acid, difluoroacetic acid, chlorodifluoroacetic acid, trifluoroacetic acid and pentafluoropropionic acid are preferred reaction solvents according to one embodiment of this invention. Among these acid solvents, those possessing high acid strength may simultaneously act both as solvents and as strong acid promoting the hydrolysis reaction and thus there is no need of a further addition of a strong acid to promote the hydrolysis reaction. For this purpose, trifluoroacetic acid proved to be particularly useful when employed at a concentration between 75% and 95% at a temperature between 60° C. and 90° C. for a reaction time varying from 0.5 hour to 8 hours.

According to a most preferred embodiment primary and secondary alkanols and secondary cycloalkanols of 5 to 10 carbon atoms are usefully employed as the reaction solvent of this controlled acid hydrolysis. Examples of said alkanols are: 1-pentanol, 2-pentanol, 3-pentanol, 1-hexanol, 2-hexanol, 3-hexanol, 3,3-dimethyl-1-butanol, 4-methyl-1-pentanol; 3-methyl-1-pentanol, 2,2-dimethyl-3-pentanol, 2,4-dimethyl-3-pentanol, 4,4-dimethyl-2-pentanol, 5-methyl-2-hexanol, 1-heptanol, 2-heptanol, 5-methyl-1-hexanol, 2-ethyl-1-hexanol, 2-methyl-3-hexanol, 1-octanol, 2-octanol, cyclopentanol, 2-cyclopentylethanol, 3-cyclopentyl-1-propanol, cyclohexanol, cycloheptanol, cyclooctanol, 2,3-dimethylcyclohexanol, 4-ethylcyclohexanol, cyclooctylmethanol, 6-methyl-5-hepten-2-ol, 1-nonanol, 2-nonanol, 1-decanol, 2-decanol and 3-decanol.

Examples of phenyl substituted lower alkanols are the following: benzyl alcohol, m-chlorobenzyl alcohol, o-fluorobenzyl alcohol, m-fluorobenzyl alcohol, p-fluorobenzyl alcohol, m-methylbenzyl alcohol, m-methoxybenzyl alcohol, o-ethoxybenzyl alcohol, m-butoxybenzyl alcohol, p-tert.butoxybenzyl alcohol, p-tert.butylbenzyl alcohol, phenethyl alcohol, o-chlorophenethyl alcohol, m-chlorophenethyl alcohol, o-methoxyphenethyl alcohol, m-methoxyphenethyl alcohol, o-propylphenethyl alcohol, o-ethoxyphenethyl alcohol, p-fluorophenethyl alcohol, p-bromophenethyl alcohol, o-propoxyphenethyl alcohol, o-butoxyphenethyl alcohol, 1-(p-isopropylphenyl)ethanol, 3-phenyl-1-propanol, 2-phenyl-1-propanol, 4-phenyl-1-butanol and 3-phenyl-1-butanol.

When the organic protic solvent is selected from beta-polyhalogenated lower alkanols which at the reaction temperature are liquids, beta-chloro- and/or fluoro-substituted alkanols of 1 to 4 carbon atoms are preferred. Examples of said beta-polyhalogenated lower alkanols are: dichloroethanol, trichloroethanol, dichlorofluoroethanol, difluorochloroethanol, difluoroethanol, trifluoroethanol, 1,1,1,3,3,3-hexa-fluoro-2-propanol, 2,2,3,4,4,4-hexafluorobutanol, and 2,2,3,3,4,4,4-heptafluorobutanol.

Preferred hydrolysis conditions for the preparation of antibiotic A 40926 aglycon is a controlled hydrolysis with a mixture of a polar aprotic solvent and a strong mineral or organic acid in the presence of a limited (0.1–10%, w/w) amount of water at a temperature between 40° C. and 100° C. and preferably between 65° C. and 90° C. for a time of from 1 h to 4 h.

Most preferably, the hydrolyzing mixture is a mixture of dimethylsulfoxide and 37% hydrochloric acid from 8:2 to 9.5:0.5, the temperature is about 80° C., the reaction time is about 3 h.

As noted above, under these conditions also antibiotic A 40926 mannosyl aglycon and antibiotic A 40926 N-acylaminoglucuronyl aglycon (complex AB or a single factor thereof), which are the products of a partial hydrolysis of the sugar-moieties of antibiotic A 40926 complex (or a single factor thereof or a mixture of said factors) are transformed into antibiotic A 40926 aglycon.

Antibiotic A 40926 N-acylaminoglucuronyl aglycon complex AB and single factors A, B, $B_0$ and $B_1$ and antibiotic A 40926 aglycon are active against gram-positive bacteria which are responsible for many widely diffused infections. Because of the increasing resistance of these pathogens to the usual therapeutic treatments, the need for new antibiotic substances is still great.

In general, for antibacterial treatment antibiotic A 40926 N-acylaminoglucuronyl aglycon complex AB, a factor thereof and/or antibiotic A 40926 aglycon as well as the non-toxic pharmaceutically acceptable salts thereof or mixture thereof, can be administered by different routes such as topically or parenterally. The parenteral administration is, in general, the preferred route of administration.

Compositions for injection may take such forms as suspensions, solutions, or emulsions in oily or aqueous vehicles, and may contain adjuvants such as suspending, stabilizing and/or dispersing agents.

Alternatively, the active ingredient may be in powder form for reconstitution at the time of delivery when a suitable vehicle, such as sterile water, is added thereto.

Depending on the route of administration, these compounds can be formulated into various dosage forms.

In some instances, it may be possible to formulate the compounds of the invention in enteric-coated dosage forms for oral administration which may be prepared as known in the art (see for instance "Remington's Pharmaceutical Sciences", fifteenth edition, Mack Publishing Company, Easton, Pa., USA, page 1614).

This could be especially the case when the absorption of the antimicrobial substance in the enteric tract is particularly desired while passing unaltered through the gastric tract.

The amount of active principle to be administered depends on various factors such as the size and condition of the subject to be treated, the route and frequency of administration, and the causative agent involved.

The antibiotic substances of the present invention, namely antibiotic A 40926 N-acylaminoglucuronyl aglycon and antibiotic A 40926 aglycon and the physiologically acceptable salts thereof, are generally effective at a daily dosage of between about 0.5 and 50 mg of active ingredient per kilogram of patient body weight, optionally divided into 1 to 4 administrations per day.

Particularly desirable compositions are those prepared in dosage units containing from about 100 to about 5,000 mg per unit.

Sustained-action formulations can be prepared based on different mechanisms and methods, as known in the art.

A preferred method for preparing a sustained-action formulation containing antibiotic A 40926 N-acylaminoglucuronyl aglycon or antibiotic A 40926 aglycon, involves the use of a water insoluble form of this antibiotic suspended in an aqueous or oily medium.

Preparation of pharmaceutical compositions:

A unit dosage form for intramuscular injection is prepared with 5 ml of sterile suspension USP containing 8% propylene glycol and 500 mg of a physiologically acceptable base addition salt of antibiotic A 40926 N-acylaminoglucuronyl aglycon complex AB.

A unit dosage form for intramuscular injection is prepared with 5 ml of sterile suspension USP containing 8% propylene glycol and 500 mg of a physiologically acceptable base addition salt of antibiotic A 40926 N-acylaminoglucuronyl aglycon factor A.

A unit dosage form for intramuscular injection is prepared with 5 ml of sterile suspension USP containing 8% propylene glycol and 500 mg of a physiologically acceptable base addition salt of antibiotic A 40926 N-acylaminoglucuronyl aglycon factor B.

A unit dosage form for intramuscular injection is prepared with 1,000 mg of antibiotic A 40926 N-acylaminoglucuronyl aglycons in the water-insoluble acid form suspended in 5 ml of sterile water for injection.

Furthermore, the antibiotic substances of the invention are useful for suppressing the growth of *Clostridium difficile* which causes pseudomembranous colitis in the intestine. These antibiotics could be used in the treatment of pseudomembranous colitis by the oral administration of an effective dose of the antibiotics or a pharmaceutically-acceptable salt thereof, prepared in a pharmaceutically-acceptable dosage form. For such use, the antibiotics can be administered in gelatin capsules or in liquid suspension.

Besides their activity as medicaments, antibiotic A 40926 N-acylaminoglucuronyl aglycons and antibiotic A 40926 aglycon and the pharmaceutically acceptable salts thereof, can be used as animal growth promoters.

For this purpose, a compound of the invention is administered orally in a suitable feed. The exact concentration employed is that which is required to provide for the active agent in a growth promotant effective amount when normal amounts of feed are consumed.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed.

The way in which such feed premixes and complete rations can be prepared and administered are described in reference books (such as "Applied Animal Nutrition", W.H. Freedman and CO., S. Francisco, USA, 1969 or "Livestock Feeds and Feeding" O and B books, Corvallis, Or., USA, 1977) and are incorporated herein by reference.

Description and preparation of the A 40926 starting materials

The production of antibiotic A 40926 complex, antibiotic A 40926 factor A, factor B, factor B$_0$, factor PA, or factor PB, is achieved by cultivating an Actinomadura sp. capable of producing it, i.e. Actinomadura sp. ATCC 39727 or an antibiotic A 40926-producing variant or mutant thereof, under aerobic conditions in an aqueous nutrient medium containing assimilable sources of carbon, nitrogen, and inorganic salts. Many of the nutrient media usually employed in the fermentation art can be used, however certain media are preferred. Preferred carbon sources are glucose, mannose, galactose, starch, corn meal and the like. Preferred nitrogen sources are ammonia, nitrates, soybean meal, peptone, meat extract, yeast extract, tryptone, aminoacids, and the like. Among the inorganic salts which can be incorporated in the culture media there are the customary soluble salts capable of yielding sodium, potassium, iron, zinc, cobalt, magnesium, calcium, ammonium, chloride, carbonate sulfate, phosphate, nitrate and the like ions.

Ordinarily, the antibiotic-producing strain is pre-cultured in a shake flask, then the culture is used to inoculate jar fermentors for production of substantial quantities of the antibiotic substances. The medium used for the pre-culture can be the same as that employed for larger fermentations, but other media can also be employed. The antibiotic A 40926 producing-strain can be grown at temperatures between 20 and 40° C., preferably between 24° and 35° C.

During fermentation, the antibiotic production can be monitored by testing broth or mycelial extract samples for antibiotic activity for instance by bioassays or TLC or HPLC procedures.

Sensitive organisms to antibiotics A 40926 such as *Bacillus subtilis* and *S. aureus* can be used as test organisms. The bioassay is conveniently performed by the agar diffusion method on agar plates. Maximum production of antibiotic activity generally occurs between the second and the fifth day of fermentation.

Antibiotic A 40926 is produced by cultivating the strain *Actinomadura sp.* ATCC 39727, or an antibiotic A 40926 producing mutant or variant thereof, and is mainly found in the culture broths.

The characteristics of Actinomadura sp. A 40926 ATCC 39727 are given in the following paragraphs Macroscopic and microscopic examination The vegetable mycelium is composed of flexuous and branched hyphae (about 0.8 μm of diameter) which on some media, identified by an asterisk in Table III, slightly tends to fragment into rod-like elements after several days of growth, while on glucose-asparagine medium it fragments into coccoid elements.

Characteristic of this strain is the Burgundy color of the vegetative mycelium on some media.

The aerial mycelium is present only in few media; in particular, among those listed in Table III, it is present only in oatmeal agar and soil agar. On these media the aerial mycelium is white-grey and forms sphorophores arranged in hooks and short spirals of about 10 to 20 spores.

The spores are cylindrical and have an average size of 0.8×1.2 μm.

Determination of growth characteristics

For the examination of the cultural characteristics, Actinomadura sp. ATCC 39727 was cultivated on various standard media suggested by Shirling and Gottlieb (Shirling E.B. and Gottlieb D., 1966—Method for characterization of Streptomyces species—Int. J. Syst. Bacteriol, 16, 313–340) with the addition of several media recommended by Waksman (Waksman, S.A. 1961—The Actinomycetes—The Williams and Wilkins Co. Baltimore; Vol. 2, 328–334).

Color determination was made whenever necessary by the method of Maerz and Paul (Maerz A. and M. Rea Paul, 1950 - A Dictionary of Color—2nd Edition McGraw-Hill Book Company Inc. N.Y.).

The ability of the organism to utilize different carbon sources was investigated by the method described by Shirling and Gottlieb.

The cultural and physiological characteristics and the carbon sources utilization are reported in Tables III, IV, and V.

The readings in Table III have been taken after two weeks incubation at 28° C.

TABLE III

CULTURAL CHARACTERISTICS OF STRAIN
Actinomadura sp. ATCC 39727

| Culture media | Characteristics |
| --- | --- |
| Medium No. 2 (yeast extract - malt agar) | Abundant growth, with crusty surface, 8/L/8, traces of amber-pink soluble pigment |
| Medium No. 3 (oatmeal agar) | Abundant growth, with smooth surface, violet, 55/E/4, aerial mycelium very scant grey, soluble pigment violet 55/H/4 |
| Medium No. 4 (inorganic salts-starch agar) | Moderate growth, with smooth and thin surface, cream 10/D/2 |
| Medium No. 5 (glycerol-asparagine agar) | Moderate growth, with smooth and thin surface, apricot 10/B/2 |
| Medium No. 6* (peptone-yeast extract iron agar) | Moderate growth, with slightly crusty surface, amber 12/D/9 |
| Medium No. 7 (tyrosine agar) | Abundant growth, with smooth and thin surface, amber-brown 13/K/12 |
| Oatmeal agar* | Abundant growth, with smooth surface, Burgundy 8/L/7, aerial mycelium, moderate light yellow-grey 44/B/2 |
| Hickey and* Tresner's agar | Abundant growth, with wrinkled surface, amber-brown 13/K/12. |
| Czapeck glucose agar | Moderate growth, with smooth surface, light-yellow 9/I/3 |
| Glucose asparagine* agar | Scant growth, with creamy surface, straw-yellow 9/E/1 |
| Nutrient agar | Abundant growth, with wrinkled surface, light-orange 11/C/7 |
| Potato agar* | Abundant growth, with wrinkled surface, Burgundy 8/L/9 |
| Bennett's agar* | Abundant growth, with crusty surface, Burgundy 8/L/8, soluble pigment deep amber rose 5/J/10 |
| Calcium malate agar | Moderate growth, with smooth surface, apricot 10/B/3 |
| Skim milk agar | Abundant growth, with slightly wrinkled surface, orange 9/B/9 |
| Czapeck sucrose agar | Abundant growth, with smooth surface, apricot 10/B/6 |
| Egg albumin agar* | Abundant growth, with smooth surface, rose 52/B/3, traces of a soluble pigment, rose 52/B/3 |
| Sabouraud agar | No growth |
| Soil agar | Scant growth, colorless, white-grey aerial mycelium |
| Dextrose triptone agar* | Moderate growth, with smooth and thin surface, light-yellow 10/G/2 |
| Potato plug | Abundant growth, orange-brown, traces of white-grey aerial mycelium |

Physiological characteristics

TABLE IV

Physiological characteristics

| Tests | Results |
| --- | --- |
| Starch hydrolysis | negative |
| H$_2$S formation | negative on Medium No. 6 positive with lead acetate strips |
| Tyrosine reaction | positive |
| Casein hydrolysis | positive |
| Calcium malate hydrolysis | negative |
| Gelatin liquefaction | positive |
| Litmus milk — coagulation | negative |
| Litmus milk — peptonization | positive |
| Cellulose decomposition | negative |
| Nitrate reduction | positive |

Utilization of carbon sources

TABLE V

| Carbon Utilization | |
| --- | --- |
| Carbon Source | Growth |
| Arabinose | + |
| Xylose | + |
| Mannose | + |
| Fructose | + |
| Raffinose | + |
| Rhamnose | + |
| Glucose | + |
| Lactose | + |
| Galactose | + |
| Inositol | − |
| Sucrose | + |
| Cellulose | − |
| Salicin | + |
| Mannitol | + |
| Ribose | − |

+ = growth
− = no growth

Chemotaxonomical characteristics

Cell wall analysis:

The analysis of aminoacids present in the cell wall was carried out by the methods described in the work of Becker et al., "Rapid differentiation between Nocardia and Streptomyces by paper chromatography of whole cell hydrolysates", Appl. Microbiol. 12, 421–423 (1964).

The analysis of the whole cell hydrolyzed revealed the presence of meso-diaminopimelic acid.

The analysis of pure cell wall, obtained with the method of Kawamoto et al. (I. Kawamoto, T. Oka, and T. Nara, "Cell-wall composition of Micromonospora olivoasterospora, Micromonospora sagamiensis, and related organism", J. of Bacteriology 146, 527–534, 1981) showed absence of glycine.

Sugar analysis:

The analysis of sugar content was carried out by the method of M.P. Lechevalier, "Identification of aerobic actinomycetes of clinical importance", J. Lab. Clin. Med. 71, 934–944 (1968) using thin layer chromoatography cellulose sheets as described by J.L. Staneck and G.D. Roberts, "Simplified approach to identification of aerobic actinomicetes by thin-layer chromatography", 28, 226–231 (1974) with the following solvent system: Ethylacetate-Pyridine-Water (100:35:25 by volume).

The obtained results showed the presence of mainly glucose and ribose while lower quantities of galactose, mannose and madurose (3-O-methyl-D-galactose) were also detected.

Mycolic acids:

An assay for detecting the presence of mycolic acids was carried out by the following method of Minnikin et al. (D. E. Minnikin, L. Alshamaony and M. Goodfellow, "Differentiation of Mycobacterium, Nocardia and related taxa by thin layer chromatography analysis of whole organism methanolysates", Journal of General Microbiology 88, 200–204, 1975).

The results of the assay were negative: mycolic acids were not found.

Identity of the strain:

The strain is assigned to the Actinomycetes genus Actinomadura because of the presence of meso-diaminopimelic acid and madurose, the lack of glycine in the peptodoglycan, the lack of mycolic acids and the formation of aerial mycelium with moderately long spore chains.

As with other microorganisms, the characteristics of the A 40926 producing strain are subject to variation. For example, artificial variants and mutants of the strain can be obtained by treatment with various known mutagens, such as U.V. rays, X-rays, high frequency waves, radioactive rays, and chemicals such as nitrous acid, N-methyl-N'-nitro-N-nitrosoguanidine, and many others. All natural and artificial variants and mutants which belong to the species of the genus Actinomadura and produce A 40926 antibiotics, are deemed equivalent to strain Actinomadura sp. ATCC 39727 and are contemplated to be within the scope of this invention.

The recovery of A 40926 antibiotics from the fermentation broths of the producing microorganism is conducted according to known per se techniques which include extraction with solvents, precipitation by adding non-solvents or by changing the pH of the solution, partition chromatography, reverse-phase partition chromatography, ion-exchange chromatography, affinity chromatography and the like.

A preferred procedure includes an affinity chromatography on immobilized D-Alanyl-D-Alanine followed by reverse-phase column chromatography.

Immobilized D-Alanyl-D-Alanine matrices suitable for the present recovery process are disclosed in European Patent Application No. 83112555. The preferred matrix in the present process is D-Alanyl-D-alanine coupled with a controlled pore cross-linked polydextrane.

The fermentation broth can be subjected to the affinity chromatography directly after filtration or after a preliminary purification procedure. This latter procedure includes making the whole fermentation mass basic, preferably between pH 8.5 and 10.5, in order to solubilize the antibiotic substance adsorbed on the mycelium and then filtering. The clear filtrate is brought to pH 2.5-4.5 and filtered again in the presence of a filter aid. This filtrate is discarded while the recovered filtration cake is suspended in water, made basic, preferably at a pH between 8 and 9, and filtered. The filtration cake is re-subjected to the same procedure while the filtrates, which contain antibiotic A 40926, are pooled.

These filtrates or the filtered fermentation broths are then subjected to an affinity chromatography on immobilized D-Alanyl-D-Alanine, either in column or batchwise.

The binding of the A 40926 antibiotic substance to the affinity matrix is preferably made at a pH of about 7.0-8.0 and its elution is performed at more basic pH values (preferably between 9.0 and 10.5) by means of an aqueous base. This aqueous base may be ammonia, a volatile amine, an alkali or alkali metal hydroxide or a basic buffered solution optionally in the presence of a polar organic solvent such as a polar water-miscible solvent as defined below.

After removing the impurities by rinsing the column with aqueous buffer pH 4-9, optionally containing salts, urea and/or water miscible solvents, the antibiotic A 40926 is eluted with the above eluting mixture. The crude antibiotic substance is then recovered preferably by removing water from the pooled antibiotic-containing fractions by azeotropical distillation with an organic solvent capable of forming minimum azeotropic mixtures with water, followed by addition of a non-solvent to precipitate the desired product.

Representative examples of organic solvents capable of forming minimum azeotropic mixtures with water are n-butanol, benzene, toluene, butyl ether, carbon tetrachloride, chloroform, cyclohexane, 2,5-dimethylfurane, hexane and m-zilene; the preferred solvent being n-butanol.

Examples of non-solvents are: petroleum ether, lower alkyl ethers, such as ethyl ether, propyl ether and butyl ether, and lower alkyl ketones such as acetone.

Alternatively, the pooled antibiotic-containing fractions are concentrated to a small volume, preferably by azeotropical distillation with an organic solvent defined as above, and the resulting aqueous solution is lyophilized.

If the aqueous base employed in the elution is unvolatile, it may be necessary to neutralize and desalt the concentrate before precipitation or freeze-drying.

A convenient desalting procedure includes applying the antibiotic containing aqueous solution to a silanized silica gel column, washing with distilled water and eluting with a mixture of a polar water-miscible solvent and water.

Representative examples of polar water-miscible solvents are: water-soluble alcohols, (such as methanol, ethanol, iso-propanol, n-butanol), acetone, acetonitrile, lower alkyl alkanoates (such as ethyl acetate), tetrahydrofuran, dioxane and dimethylformamide and mixtures thereof; the preferred polar water-miscible solvent being acetonitrile.

Alternatively, desalting may be carried out by applying the antibiotic containing solution to the above described affinity column, washing with distilled water and eluting with a volatile aqueous base as described above for the elution of the affinity chromatography.

The product so obtained is antibiotic A 40926 complex. If necessary, it may be further purified or subjected as such to the separation of its factors A, B, $B_0$, $P_A$ and $P_B$.

A convenient procedure to obtain a pure antibiotic A 40926 complex is represented by a further purification of the complex as obtained above on an affinity chromatography column. The same stationary phase as above (immobilized D-Alanyl-D-Alanine) is generally used and the desired antibiotic substance is eluted by following the affinity chromatography procedure on immobilized D-Alanyl-D-Alanine described above.

A preferred immobilized D-Alanyl-D-Alanine is Sepharose-ε-aminocaproyl-D-Alanyl-d-Alanine, a preferred equilibrating mixture is 0.16% (w/v) ammonia containing 2M NaCl adjusted to pH 7-8, a preferred rinsing solution is 0.16% (w/v) ammonia containing 2M NaCl adjusted to pH 8-9.5, a preferred eluting mixture is 0.16% (w/v) ammonia containing 2M NaCl adjusted to pH 10.5–12 and a most preferred eluting mixture is the above mixture adjusted to pH 11.5.

The antibiotic A 40926 factors, namely antibiotic A 40926 factor A, antibiotic A 40926 factor B, antibiotic A 40926 factor $B_0$, antibiotic A 40926 factor PA and antibiotic A 40926 factor PB are isolated from an aqueous solution of antibiotic A 40926 complex by column chromatography and preferably by reverse-phase column chromatography. The preferred stationary phase in the case of reverse-phase column chromatography is silanized silica gel. Good results may be obtained however also with column chromatography on non-funtionalized polystyrene and acrylic resins such as those sold under the trade names Amberlite XAD-2, XAD-4, XAD-7 and XAD-8 (Rohm and Haas) or Diaion HP 20 (Mitsubishi).

In case the reverse-phase purification step is accomplished by means of a silanized silica gel as the stationary phase, the column is preferably pre-equilibrated with a buffered aqueous solution at pH between 4 and 9 and preferably between 5.5–6.5 and then eluted with a linear gradient of a polar water-miscible solvent in the same buffered solution. Representative examples of polar water-miscible solvents are: water-soluble alcohols, (such as methanol, ethanol, iso-propanol, n-butanol), acetone, acetonitrile, tetrahydrofuran, dioxane and dimethylformamide and mixtures thereof; the preferred polar water-miscible solvent being acetonitrile.

The eluted fractions are assayed for their antibiotic content by means of the usual bioassays, such as paper-disc or agar-diffusion assays, on susceptible microorganisms. Examples of susceptible organisms are *Bacillus subtilis* and *S. aureus*.

The chromatography is also conveniently monitored by TLC or HPLC techniques.

A preferred HPLC technique is represented by a reverse-phase HPLC using a column of porous and spheric particles of silanized silica gel according to the method described above when dealing with the HPLC procedure for the analysis of antibiotic A 40926 antibiotics.

Fractions with a similar antibiotic content are pooled and desalted as described above to give essentially pure antibiotic A 40926 factor A, factor B, factor $B_0$, factor PA, and factor PB.

Essentially pure antibiotic A 40926 factor A and antibiotic A 40926 factor B, antibiotic A 40926 factor $B_0$, antibiotic A 40926 factor PA and antibiotic A 40926 factor PB are obtained from those fractions containing them by a variety of known techniques such as lyophilization, precipitation by non-solvents or precipitation by changing the pH of the aqueous solution.

A convenient procedure includes adding a solvent capable of forming azeotropic mixtures with water, removing water by azeotropic distillation and then collecting by filtration the precipitate obtained after addition of a non-solvent like those described above.

Antibiotic A 40926 factors PA and PB, at least under certain fermentation conditions, are the main antibiotic products of the A 40926 producing microorganism.

Antibiotic A 40926 factors A and B are mainly transformation products of antibiotic A 40926 factor PA and factor PB respectively, and are often already present in the fermentation broth.

It has been found that antibiotic A 40926 factor PA can be transformed into antiobiotic A 40926 factor A and antibiotic A 40926 factor PB can be transformed into antibiotic A 40926 factor B under basic conditions.

For instance, antibiotic A 40926 factor PA and antibiotic A 40926 factor PB are transformed into antibiotic A 40926 factor A and factor B respectively, by treatment with 0.5–10% aqueous ammonia or other nucleophilic base such as an organic amine at room temperature for 8–24 hours.

As a consequence, when the fermentation broth, or an antibiotic A 40926 containing extract or concentrate thereof, is allowed to stand for a certain time under basic conditions (e.g. aqueous solution of a nucleophilic base, at a pH>9 overnight,) an antibiotic A 40926 complex will be obtained which is enriched in antibiotic A 40926 factor A and factor B. If the period of exposure of the fermentation broth, extract or concentrate thereof, to a basic environment is short, an antibiotic A 40926 complex is obtained which is enriched in antibiotic A 40926 factor PA and factor PB.

A preferred procedure to obtain an antibiotic A 40926 complex enriched in factor A and factor B includes therefore leaving a solution of antibiotic A 40926 complex (which contains mainly antibiotic A 40926 factors PA and PB) at room temperature for 8–12 h in an aqueous nucleophilic base, such as aqueous ammonia, and then isolating the desired antibiotic complex as described above.

Examples of A 40926 containing solutions are fermentation broths, extracts and affinity chromatography eluted fractions.

Pure antibiotic A 40926 may be obtained by further purifying the crude complex by affinity chromatography as described above.

The product so obtained which possesses biological and physico-chemical properties derivable from the pure factors thereof, will be referred to in the examples as antibiotic A 40926 complex AB.

A preferred procedure to enrich in factors PA and PB an antibiotic A 40926 complex preparation, includes rapidly neutralizing the affinity chromatography eluted fractions with an acid, preferably a mineral acid such as sulfuric or hydrochloric acid.

The isolation of pure antibiotic A 40926 factors PA and PB from this complex can be achieved according to one of the above reported procedures.

A preferred procedure includes reverse-phase liquid chromatography, preferably in stainless steel columns under moderate pressure (5–50 bar) or at high pressure (100–200 bar). The solid phase may be a silanized silica gel with a hydrocarbon phase at (2–18) carbon atoms (most preferably C 18) or phenyl group, and the eluent is a mixture of a polar water-miscible solvent as defined above and an aqueous buffer at a pH compatible with the resin (preferably pH 4–8).

The elution is monitored as usual, the fractions having homogeneous antibiotic content are pooled and treated as described above to isolate the pure compounds having the characteristics reported below.

Sophisticated HPLC analysis has shown that antibiotic A 40926 factor B actually is a mixture of two factors denominated factor $B_0$ and factor $B_1$.

Antibiotic A 40926 factor $B_0$, which accounts for approximately 90% of antibiotic A 40926 factor B, is the factor that has $R_f$ of 1.22 relative to Teicoplanin $A_2$ component 2 in the system described below under point D of the physico-chemical characteristics of factor B, while factor $B_1$, which accounts for approximately 10% of antibiotic A 40926 factor B, is that with relative $R_f$ of 1.27 in the same system.

Pure antibiotic A 40926 factor $B_0$ is obtained by further purification of antibiotic A 40926 factor B for instance by repeating the reverse-phase chromatography procedure used for its isolation.

The physico-chemical and biological properties of antibiotic A 40926 factor $B_0$ are substantially identical to those of antibiotic A 40926 factor B except that at the HPLC analysis in a system like the above cited one, it has only one peak ($R_t$ 1.22 relative to Teicoplanin $A_2$ component 2 in the described HPLC system).

Because of the above outlined similarities between antibiotic A 40926 factor B and antibiotic A 40926 factor $B_0$ in the present disclosure the reference to the biological properties of antibiotic A 40926 factor B is to be understood as referring also to antibiotic A 40926 factor $B_0$ which is the main component (about 90%) of antibiotic A 40926 factor B and mainly contributes to its biological properties.

Alternatively, the antibiotic substances of the invention may be isolated from the fermentation broth or further purified by means of strong or weak anion resins including functionalized polystyrene, acrylic or polydextrane matrices. Examples of weak anion exchange resins are those sold under the following trade-names: Dowex MWA-1 or WGR (Dow Chemical), Amberlite IRA-73 (Rohm and Haas), DEAE-Sephadex (Pharmacia). Examples of strong anion exchange resins which may be used according to invention include those sold under the following trade names: Dowex MSA-1, SBR, SBR-P (Dow Chemical), Amberlite IR-904 (Rohm and Haas) and QAE-Sephadex (Pharmacia).

The elution of the A 40926 antibiotic substances from these resins is conducted by means of linear gradient mixtures of aqueous solution of electrolytes, such as sodium or potassium hydrochlorides, in water or mixtures of water and an organic water-miscible solvent such as a lower alcohol (e. g. ($C_1$–$C_4$) alkanol) or lower alkyl ketones (e.g. acetone).

Antibiotic A 40926 mannosyl aglycon is prepared by hydrolizing antibiotic A 40926 complex enriched in factor A and factor B, antibiotic A 40926 factor A, factor B, factor $B_0$ or mixtures thereof under controlled acidic conditions.

These controlled acid conditions are represented by a concentrated aqueous solution of a mineral or organic strong acid optionally in the presence of an aprotic organic solvent. Preferred examples of strong mineral acids are sulfuric and phosphoric acid.

A preferred strong organic acid is trifluoroacetic acid.

Preferred aprotic organic solvents are alicyclic or cyclic alkyl ethers such as dioxane and tetrahydrofuran, lower alkyl sulfoxides such as dimethylsulfoxide and lower alkyl amides such as dimethylformamide.

The reaction temperature is generally kept between 0° C. and the reflux temperature of the reaction mixture. In many instances it is between 15° C. and 75° C., while a preferred temperature is between 20° C. and 55° C. and most preferably it is room temperature.

The reaction time varies depending on the specific reaction parameters and since the reaction course may be followed by TLC or HPLC techniques, the man skilled in the art is capable of monitoring the reaction course and deciding when the reaction may be considered complete.

A preferred embodiment of this process is represented by the controlled hydrolysis of antibiotic A 40926 complex or a pure factor thereof to give antibiotic A 40926 mannosyl aglycon in the presence of aqueous 80-95% trifluoroacetic acid at room temperature.

Another preferred embodiment of this process is represented by the controlled hydrolysis of antibiotic A 40926 mannosyl aglycon in the presence of a mixture 2:1 to 1:2 of aqueous 1-2 N sulfuric acid and dioxane.

The purification of crude antibiotic A 40926 mannosyl aglycon as recovered at the end of the hydrolysis step may be accomplished according to known per se techniques, such as precipitation by addition of non-solvents, extraction with solvents and chromatography.

Preferred chromatographic procedures includes column chromatography and the most preferred chromatographic procedure is reverse-phase column chromatography.

A suitable reverse-phase liquid chromatography procedure, preferably employs stainless steel colums under moderate pressure (5–50 bar) or at high pressure (100-200 bar). The solid phase may be a silanized silica gel with a hydrocarbon phase at (2–18) carbon atoms (most preferably C 18) or phenyl group, and the eluent is a mixture of a polar water-miscible solvent and an aqueous buffer at a pH compatible with the resin (preferably pH 3–8).

Representative examples of polar water-miscible solvents are: water-soluble alcohols, (such as methanol), ethanol, iso-propanol, n-butanol), acetone, acetonitrile, lower alkyl alkanoates (such as ethyl acetate), tetrahydrofuran, dioxane and dimethylformamide and mixtures thereof; the preferred polar water-miscible solvent being acetonitrile.

The eluted fractions are assayed for their antibiotic content by means of the usual bioassays, such as paper-disc or agar-diffusion assays, on susceptible microorganisms. Examples of susceptible organisms are *Bacillus subtilis* and *S. aureus*.

The purification as well as the reaction are also conveniently monitored by TLC or HPLC techniques.

A preferred HPLC technique is represented by a reverse-phase HPLC using a column of porous and spheric particles of silanized silica gel functionalized with C-18 alkyl groups having a diameter preferably of 5 micrometers (such as 5 $\mu$m Ultrasphere® ODS Altex; Beckman Co.), a pre-column which is a silica gel functionalized with C-18 alkyl groups (such as RP 18 Brownlee Labs) and an eluent which is a linear gradient mixture of a polar water miscible solvent, such as one of those described above, in an aqueous buffered solution.

Preferably this solution is adjusted to pH 5-7. A most preferred eluent is represented by a linear gradient from 5 to 60% of eluent B in eluent A wherein eluent A is a mixture of acetonitrile/aqueous buffer, pH 5-7, 10:90 and eluent B is a mixture of acetonitrile/aqueous buffer, pH 5-7, 70:30. As known in the art, many substances can be used as internal standards. A very convenient one is, in this case, antibiotic L 17054 which has a retention time close to the compounds of the invention in this HPLC system. This standard substance is known and has been described in European Patent Application Publication No. 0119575.

The antibacterial activity of the compound of the invention can be demonstrated in vitro by means of standard dilution tests on different microorganism cultures.

Figure 11:
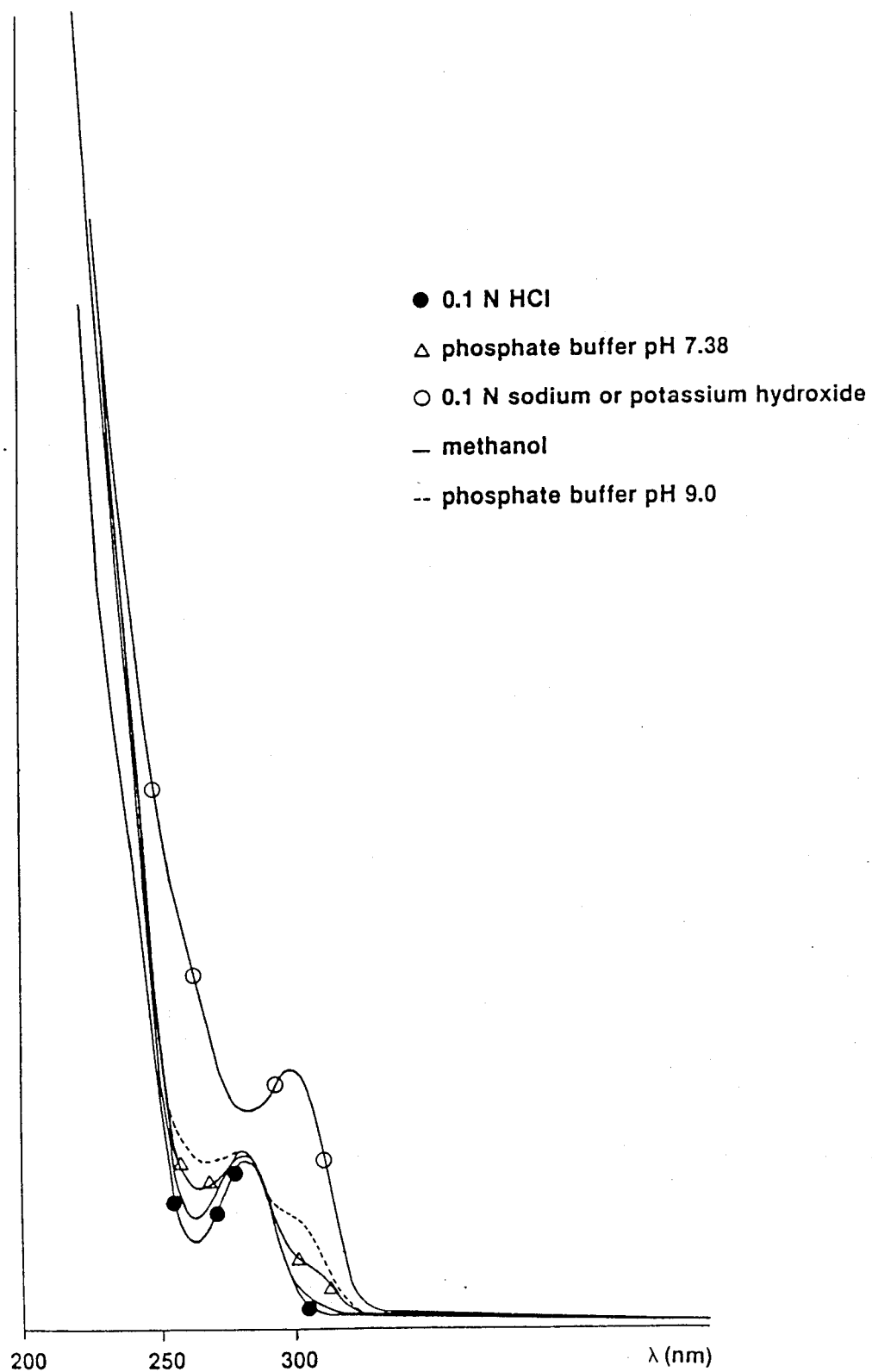

Physico-chemical characteristics of antibiotic A 40926 factor A (A) ultraviolet absorption spectrum, which is shown in FIG. 11 of the accompanying drawings, and exhibits the following absorption maxima:

|     |                              | λ max (nm)       |
|-----|------------------------------|------------------|
| (a) | 0.1 N HCl                    | 281              |
| (b) | phosphate buffer pH 7.38     | 281              |
|     |                              | 300 (shoulder)   |
| (c) | 0.1 N sodium or potassium hydroxide | 300       |
| (d) | methanol                     | 282              |
| (e) | phosphate buffer pH 9.0      | 282              |
|     |                              | 300 (shoulder)   |

Figure 12:
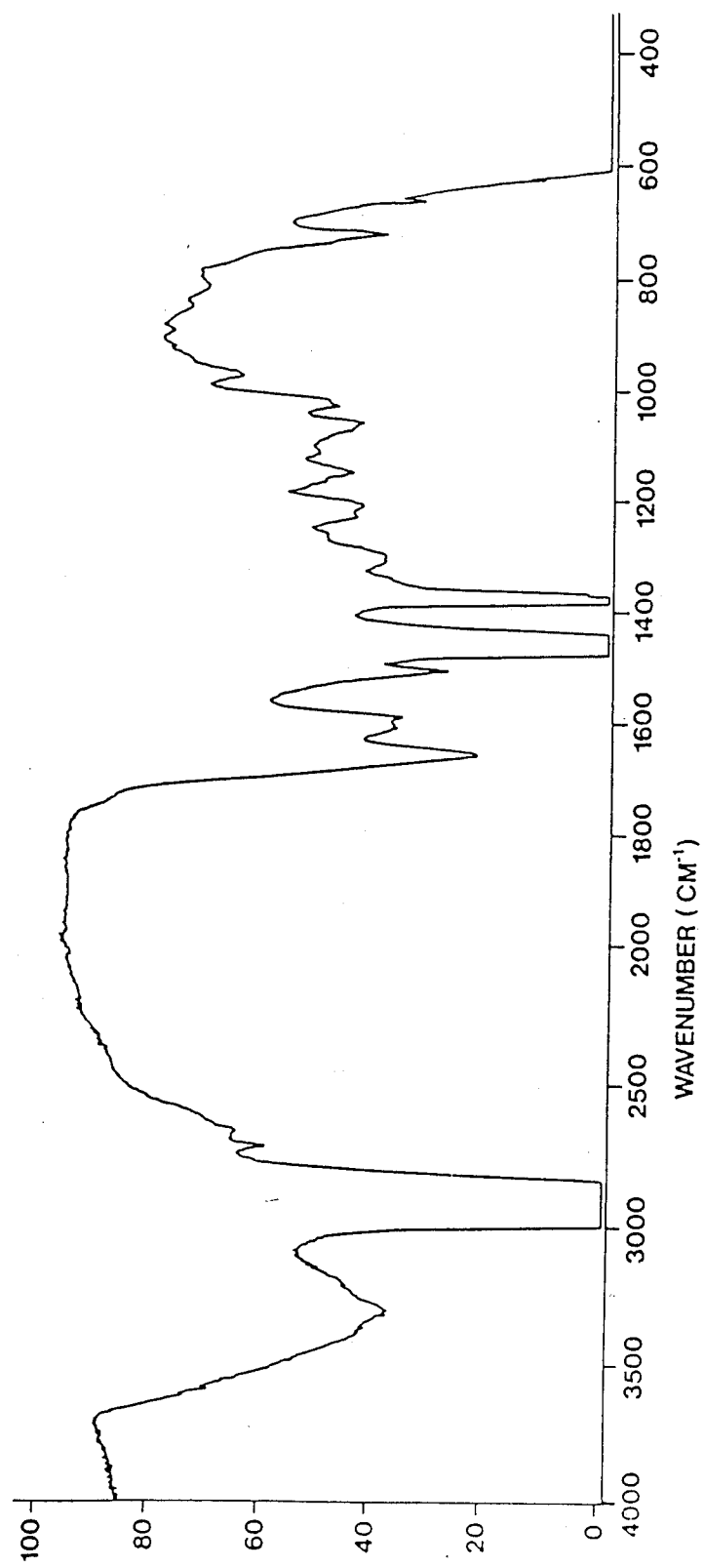

(B) infrared absorption spectrum which is shown in FIG. 12 of the accompanying drawings and exhibits the following absorption maxima ($cm^{-1}$): 3700–3100; 3100–2800 (nujol); 1655; 1620–1560; 1510; 1480–1410 (nujol); 1375 (nujol); 1320–1250; 1250–1190; 1100–950; 845; 810; 720 (nujol).

Figure 13:
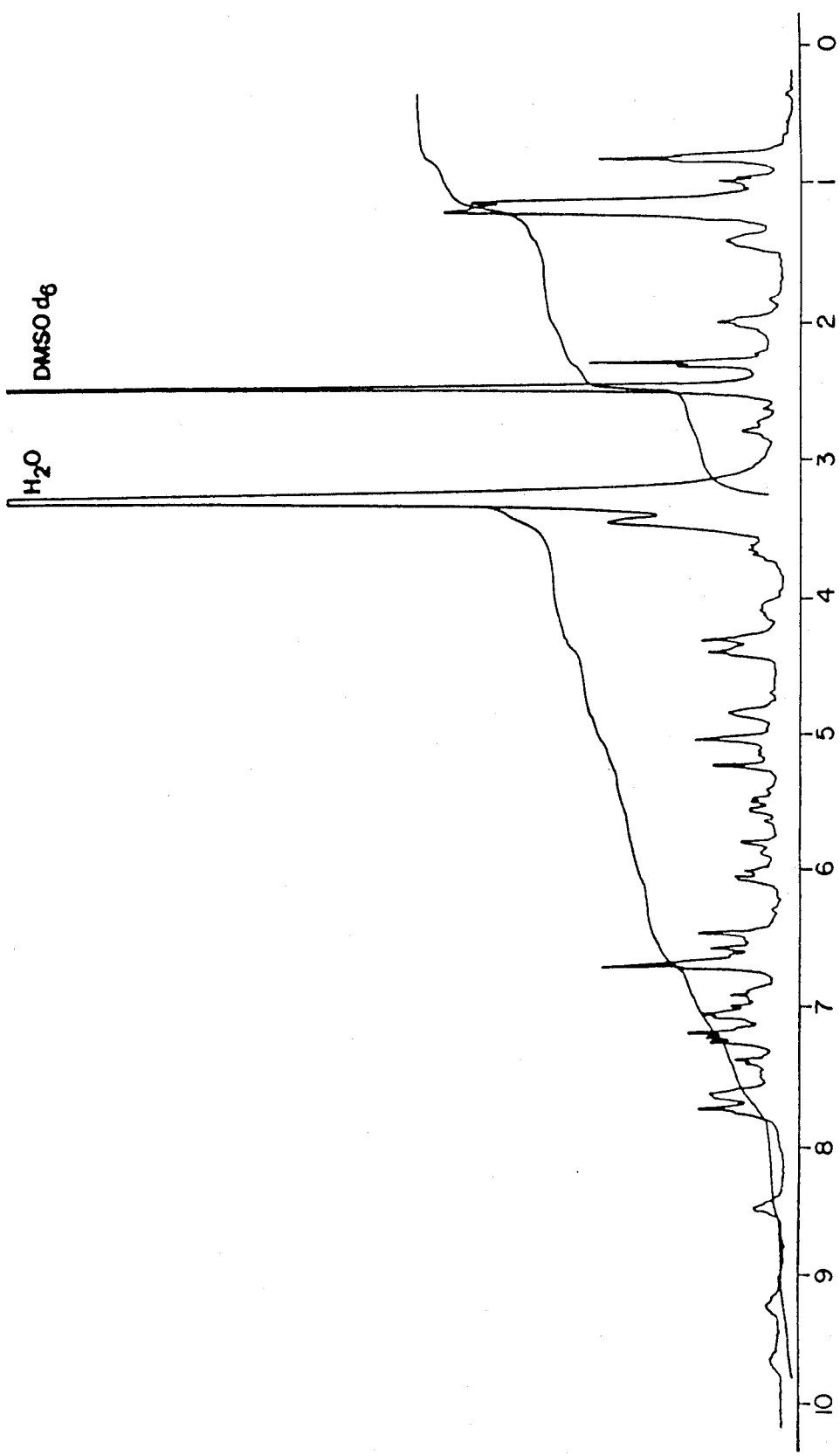

(C) $^1$H-NMR spectrum which is shown in FIG. 13 and exhibits the following groups of signals (in ppm) at 270 MHz recorded in DMSO $d_6$ (hexadeuterodimethylsulfoxide) using TMS as the internal standard (0.00 ppm), (δ=ppm): δ0.86 (t's, 6H); 1.21 (~11H); 1.43 (2H); 2.01 (2H); 2.32–2.34 (3H); 4–6.2 (~16H); 6.2–8 (~23H); 8.44, 9.22, 9.66 (broad bands; mobile protons) 2.5–4: interference from $H_2O$ peaks.

(D) retention-time ($R_t$) of 1.12 relative to Teicoplanin $A_2$ component 2 ($R_t$=20.3 min), when analyzed by reverse phase HPLC under the following conditions:
column: Ultrasphere ODS (5 μm) Altex (Beckman) 4.6 mm (i.d.)×250 mm
pre-column: Brownlee Labs RP 18 (5 μm)

| eluent A: | $CH_3CN$             | 10% | adjusted at pH 6.0 |
|-----------|----------------------|-----|--------------------|
|           | (2.5 g/l) $NaH_2PO_4.H_2O$ | 90% |              |
| eluent B: | $CH_3CN$             | 70% | adjusted at pH 6.0 |
|           | (2.5 g/l) $NaH_2PO_4.H_2O$ | 30% |              | elution: linear gradient from 5% to 60% of eluent B in eluent A, in 40 min
flow rate: 1.8 ml/min
U.V. detector: 254 nm
internal standard: Teicoplanin $A_2$ component 2 (Gruppo Lepetit S.p.A.)

Under the same conditions the retention time relative to Testosterone (Roussel Uclaf) is 0.60.

(E) elemental analysis, after the sample has been previously dried at about 140° C. under inert atmosphere (Δw 4.6%) which indicates the following approximate percentage composition (average): carbon 55.82%; hydrogen 5.17%; nitrogen 6.31%; chlorine (total) 4.24%; chlorine (ionic) 0.37%. Inorganic residue at 900° C. in the air: 1.2%.

(F) acid-base titration profile in 2-methoxyethanol (MCS):water, 4:1 upon titration with KOH after addition of an excess of HCl which indicates four ionizable functions having the following $pk_{MCS}$: 4.6, 5.6, 7.2, 9.2.

(G) $R_f$ value of 0.24 and a $R_f$ value relative to Teicoplanin $A_2$ component 2 of 0.70 in the following chromatographic system:

| 5% (w/v) aqueous $Na_2SO_4$ | 70 |
|------------------------------|-----|
| acetonitrile                | 30 | using silanized silica gel 60 $F_{254}$ Merck plates (layer thickness 0.25 mm) Visualization:
U.V. light
Yellow color with Pauly Reagent, i.e. diazotized sulfanilic acid (J. Chromatog. 20, 171 (1965), Z. Physiol. Chem. 292, 99, (1953))
Bioautography using B. subtilis ATCC 6633 on minimal Davis medium.

(H) MW of about 1716 desumed from a FAB-MS spectrum showing the $M+H^\oplus$ peak at 1717.

Figure 14:
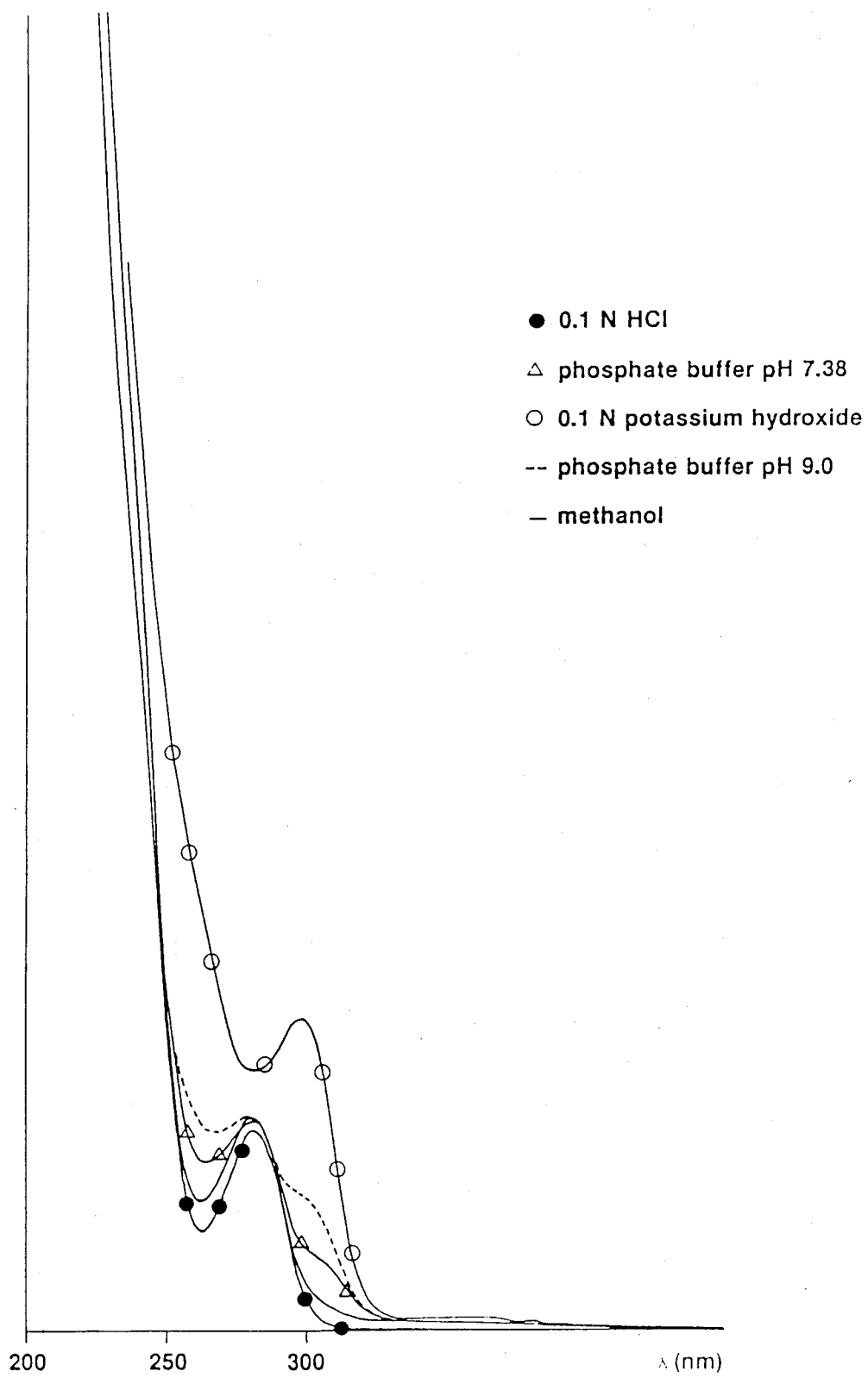

Physico-chemical characteristics of antibiotic A 40926 factor B (A) ultraviolet absorption spectrum, which is shown in FIG. 14 of the accompanying drawings, and exhibits the following absorption maxima:

|     |                              | λ max (nm)       |
|-----|------------------------------|------------------|
| (a) | 0.1 N HCl                    | 282              |
| (b) | phosphate buffer pH 7.38     | 281              |
|     |                              | 300 (shoulder)   |
| (c) | 0.1 N sodium or potassium hydroxide | 300       |
| (d) | phosphate buffer pH 9.0      | 283              |
|     |                              | 300 (shoulder)   |
| (e) | methanol                     | 282              |

Figure 15:
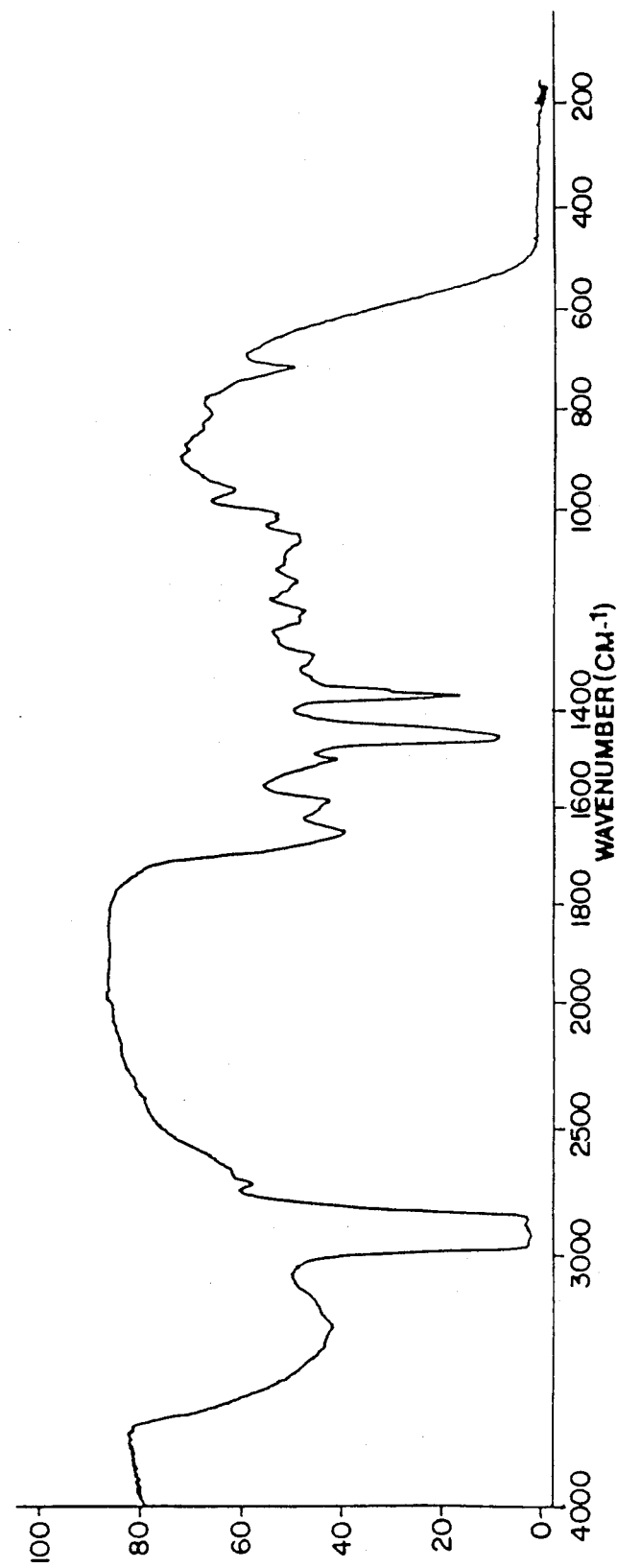

(B) infrared absorption spectrum which is shown in FIG. 15 of the accompanying drawings and exhibits the following absorption maxima ($cm^{-1}$): 3700–3080; 3080–2700 (nujol); 1720–1625; 1625–1560; 1505; 1460 (nujol); 1375 (nujol); 1295; 1230; 1210; 1150; 1100–1040; 1030; 1015; 970; 890; 840; 810; 720 (nujol).

Figure 16:
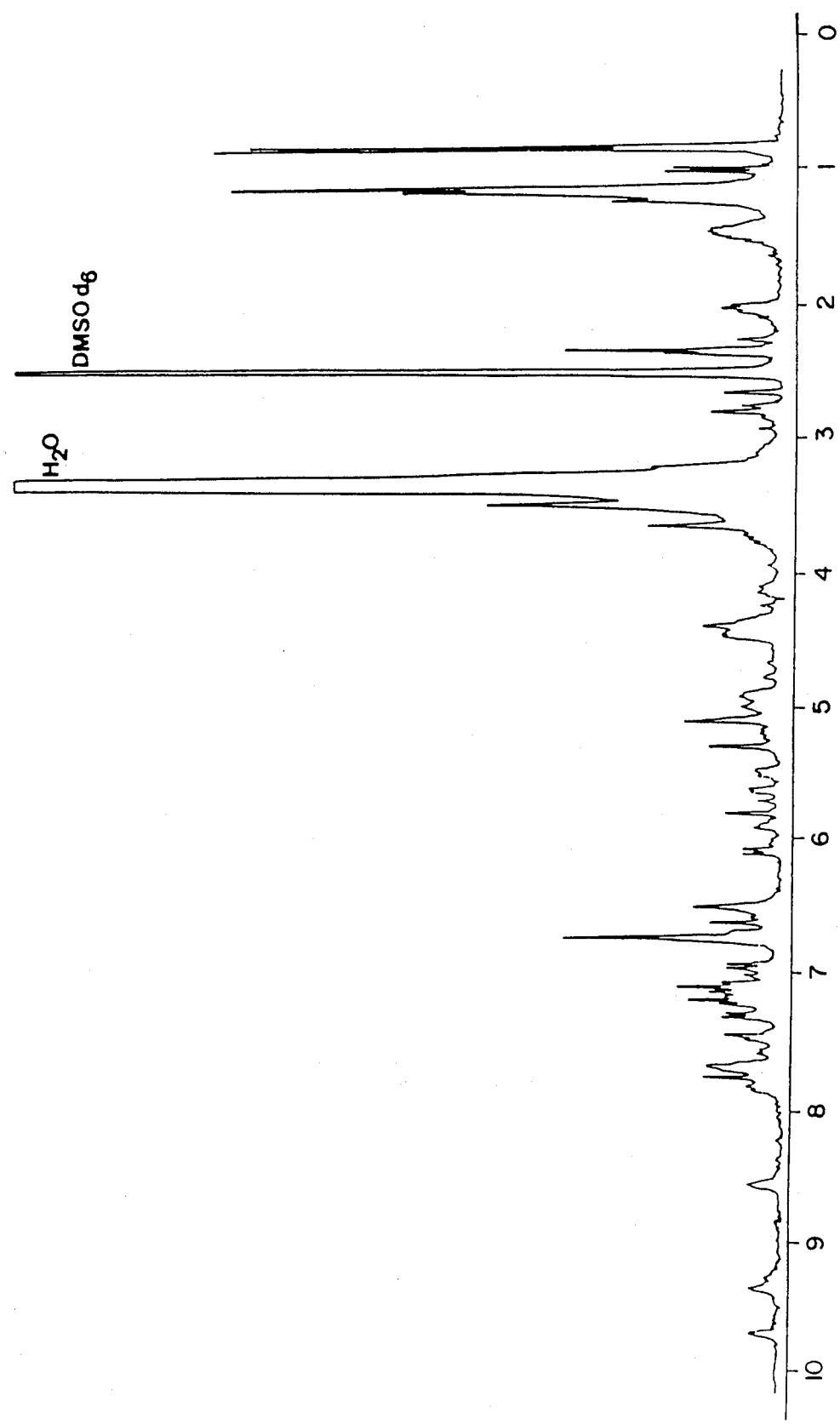

(C) $^1$H-NMR spectrum shown in FIG. 16 exhibits the following groups of signals (in ppm) in the 270 MHz $^1$H-NMR recorded in DMSO $d_6$ (hexadeuterodimethylsulfoxide) using TMS as the internal standard (0.00 ppm), (δ=ppm): δ0.85 (d, isopropyl $CH_3$'s); 1.15 (~13H); 1.44 (~2H); 2.02 (2H); 2.32–2.35 (3H); 4–6.1 (~16H); 6.1–8 (~23H); 8.52, 9.30, 9.68 (broad bands; mobile protons) 2.5–4 interference from $H_2O$ peaks.

(D) Retention times ($R_t$) of 1.22 and 1.27 relative to Teicoplanin $A_2$ component 2 ($R_t$=20.3 min) when analyzed by reverse phase HPLC under the following conditions:
column: Ultrasphere ODS (5 μm) Altex (Beckman) 4.6 mm (i.d.)×250 mm
pre-column: Brownless Labs RP 18 (5 μm)

| eluent A: | $CH_3CN$             | 10% | adjusted at pH 6.0 |
|-----------|----------------------|-----|--------------------|
|           | (2.5 g/l) $NaH_2PO_4.H_2O$ | 90% |              |
| eluent B: | $CH_3CN$             | 70% | adjusted at pH 6.0 |
|           | (2.5 g/l) $NaH_2PO_4.H_2O$ | 30% |              | elution: linear gradient from 5% to 60% of eluent B in eluent A, in 40 min
flow rate: 1.8 ml/min
U.V. detector: 254 nm
internal standard: Teicoplanin $A_2$ component 2 (Gruppo Lepetit S.p.A.)

(E) elemental analysis, after the sample has been previously dried at about 140° C. under inert atmosphere (Δw 9.6%) indicates the following approximate percentage composition (average): carbon 54.09%; hydrogen 5.13%; nitrogen 6.34%; chlorine (total) 4.12%; chlorine (ionic) 0.39%. Inorganic residue at 900° C. in the air: 5%.

(F) acid base titration profile in 2-methoxyethanol (MCS):water, 4:1 upon titration with KOH after addition of an excess of HCl (pH 2.7) which indicates four ionizable functions having the following $pk_{MCS}$:4.5, 5.6, 7.2, 9.2.

(G) $R_f$ value of 0.21 and a $R_f$ value relative to Teicoplanin $A_2$ component 2 of 0.53 in the following chromatographic system:

| 5% (w/v) aqueous $Na_2SO_4$ | 70 |
|---|---|
| acetonitrile | 30 | using silanized silica gel 60 $F_{254}$ Merck plates (layer thickness 0.25 mm) Visualization:
U.V. light
Yellow color with Pauly Reagent, i.e. diazotized sulfanilic acid (J. Chromatog. 20, 171 (1965), Z. Physiol. Chem. 292, 99, (1953))
Bioautography using B. subtilis ATCC 6633 on minimal Davis medium.

(H) MW of about 1730 desumed from a FAB-MS spectrum showing the M+H⊕ peak at 1731.

Physico-chemical characteristics of antibiotic A 40926 factor $B_0$ (A) ultraviolet absorption spectrum which is shown in FIG. 14 of the accompanying drawing and exhibits the following absorption maxima:

| | | λ max (nm) |
|---|---|---|
| (a) | 0.1 N HCl | 282 |
| (b) | phosphate buffer pH 7.38 | 281 |
| | | 300 (shoulder) |
| (c) | 0.1 N sodium or potassium hydroxide | 300 |
| (d) | phosphate buffer pH 9.0 | 283 |
| | | 300 (shoulder) |
| (e) | methanol | 282 |

(B) infrared absorption spectrum which shown in FIG. 15 of the accompanying drawings exhibits the following absorption maxima (cm$^{-1}$): 3700-3080, 3080-2700 (nujol); 1720-1625; 1625-1560; 1505; 1460 (nujol); 1375 (nujol); 1295; 1230; 1210; 1150; 1100-1040; 1030; 1015; 970; 890; 840; 810; 720 (nujol).

(C) $^1$H-NMR spectrum which shown in FIG. 16 exhibits the following groups of signals (in ppm) in the 270 MHz $^1$H-NMR recorded in DMSO $d_6$ (hexadeuterodimethylsulfoxide) using TMS as the internal standard (0.00 ppm), (δ=ppm): δ0.85 (d, isopropyl $CH_3$'s); 1.15 (~13H); 1.44 (~2H); 2.02 (2H); 2.32-2.35 (3H); 4-6.1 (~16H); 6.1-8 (~23H); 8.52, 9.30, 9.68 (broad bands; mobile protons) 2.5-4 interference from $H_2O$ peaks.

(D) Retention time ($R_t$) of 1.22 relative to Teicoplanin $A_2$ component 2 ($R_t$=20.3 min) when analyzed by reverse phase HPLC under the following conditions:
column: Ultrasphere ODS (5 μm) Altex (Beckman) 4.6 mm (i.d.)×250 mm
pre-column: Brownlee Labs RP 18 (5 μm)

| eluent A: | $CH_3CN$ | 10% | ⎫ | adjusted at |
|---|---|---|---|---|
| | (2.5 g/l) $NaH_2PO_4.H_2O$ | 90% | ⎭ | pH 6.0 |
| eluent B: | $CH_3CN$ | 70% | ⎫ | adjusted at |
| | (2.5 g/l) $NaH_2PO_4.H_2O$ | 30% | ⎭ | pH 6.0 | elution: linear gradient from 5% to 60% of eluent B in eluent A, in 40 min
flow rate: 1.8 ml/min
U.V. detector: 254 nm
internal standard: Teicoplanin $A_2$ component 2 (Gruppo Letetit S.p.A.)

(E) elemental analysis, after the sample has been previously dried at about 140° C. under inert atmosphere (Δw 9.6%) indicates the following approximate percentage composition (average): carbon 54.09%; hydrogen 5.13%; nitrogen 6.34%; chlorine (total) 4.12%; chlorine (ionic) 0.39%. Inorganic residue at 900° C. in the air: 5%.

(F) acid base titration profile in 2-methoxyethanol (MCS):water, 4:1 upon titration with KOH after addition of an excess of HCl indicates four ionizable functions having the following $pk_{MCS}$: 4.5, 5.6, 7.2, 9.2.

(G) $R_f$ value of 0.21 and a $R_f$ value relative to Teicoplanin $A_2$ component 2 of 0.53 in the following chromatographic system:

| 5% (w/v) aqueous $Na_2SO_4$ | 70 |
|---|---|
| acetonitrile | 30 | using silanized silica gel 60 $F_{254}$ Merck plates (layer thickness 0.25 mm) Visualization:
U.V. light
Yellow color with Pauly Reagent, i.e. diazotized sulfanilic acid (J. Chromatog. 20, 171 (1965), Z. Physiol. Chem. 292, 99, (1953))
Bioautography using B. subtilis ATCC 6633 on minimal Davis medium.

(H) MW of about 1730 desumed from a FAB-MS spectrum showing the M+H⊖ peak at 1731.

Figure 17:
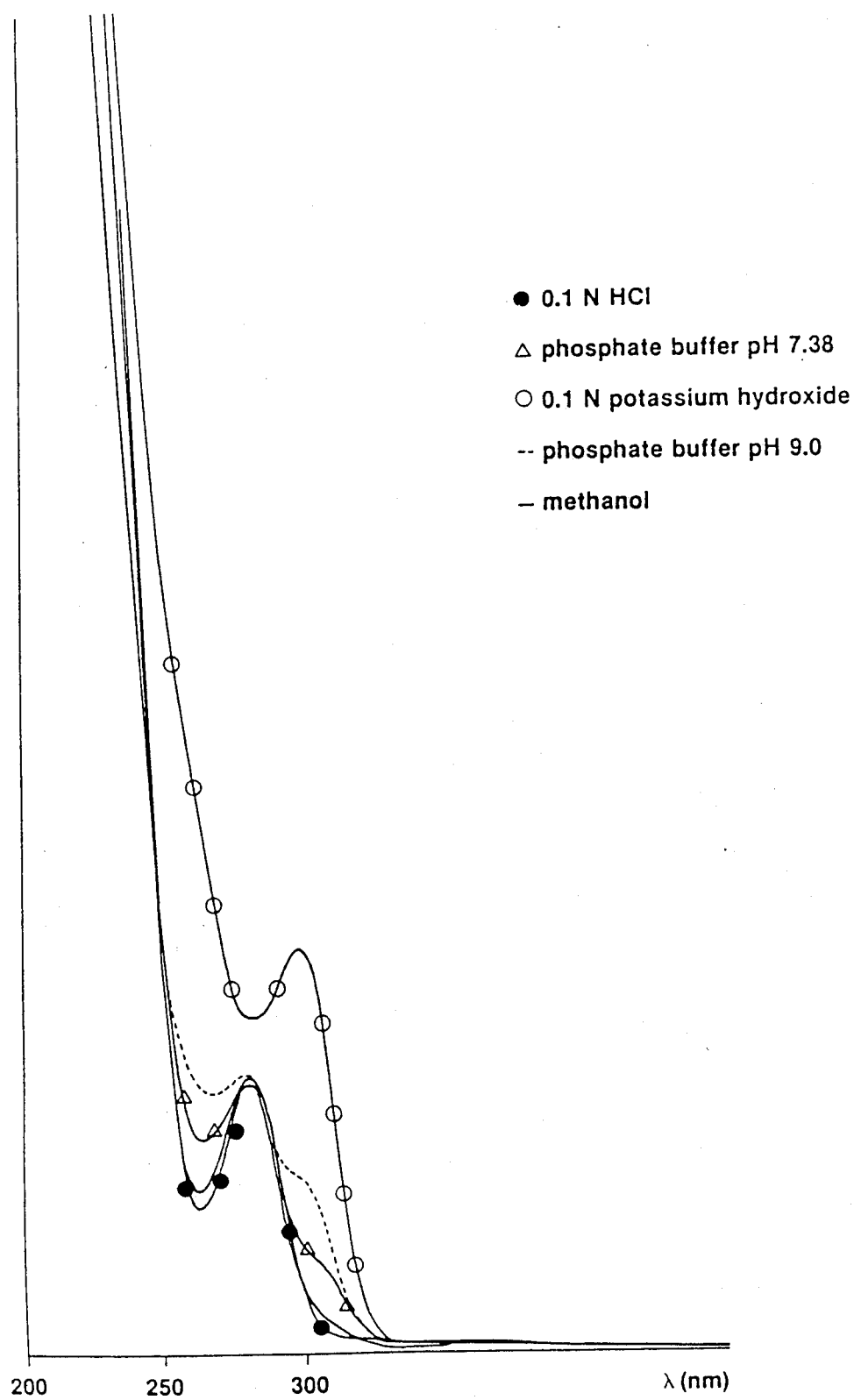

Physico-chemical characteristics of antibiotic A 40926 factor PA (A) ultraviolet absorption spectrum, shown in FIG. 17 of the accompanying drawings, exhibits the following absorption maxima:

| | | λ max (nm) |
|---|---|---|
| (a) | 0.1 N HCl | 282 |
| (b) | 0.1 N potassium hydroxide | 300 |
| (c) | phosphate buffer pH 7.38 | 282 |
| | 300 (shoulder) | |
| (d) | phosphate buffer pH 9.0 | 283 |
| | 300 (shoulder) | |

Figure 18:
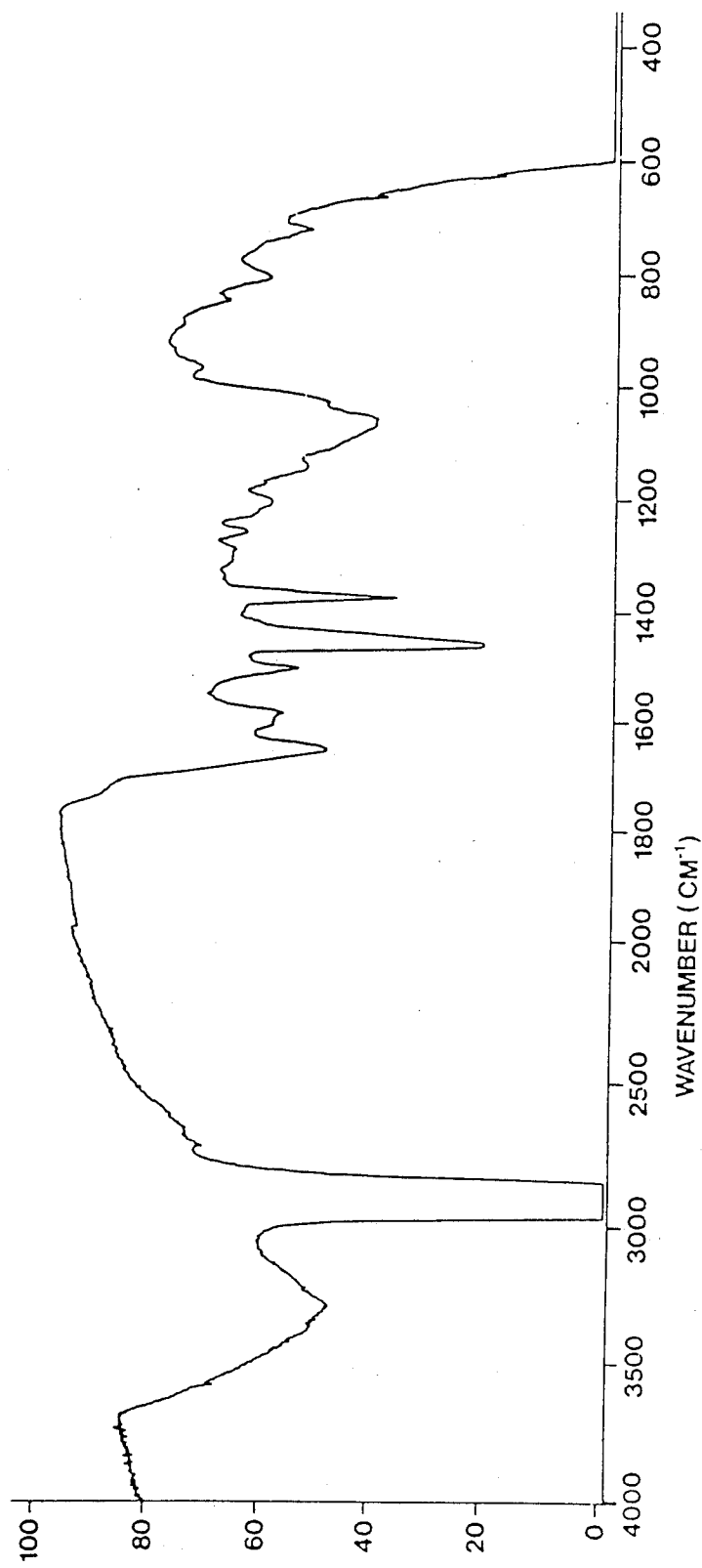

(B) infrared absorption spectrum shown in FIG. 18 of the accompanying drawings exhibits the following absorption maxima (cm$^{-1}$): 3700-3100, 3000-2800 (nujol); 1760-1710; 1655; 1620-1550; 1505; 1460 (nujol); 1375 (nujol); 1260, 1250-950; 845; 805; 720 (nujol)

Figure 19:
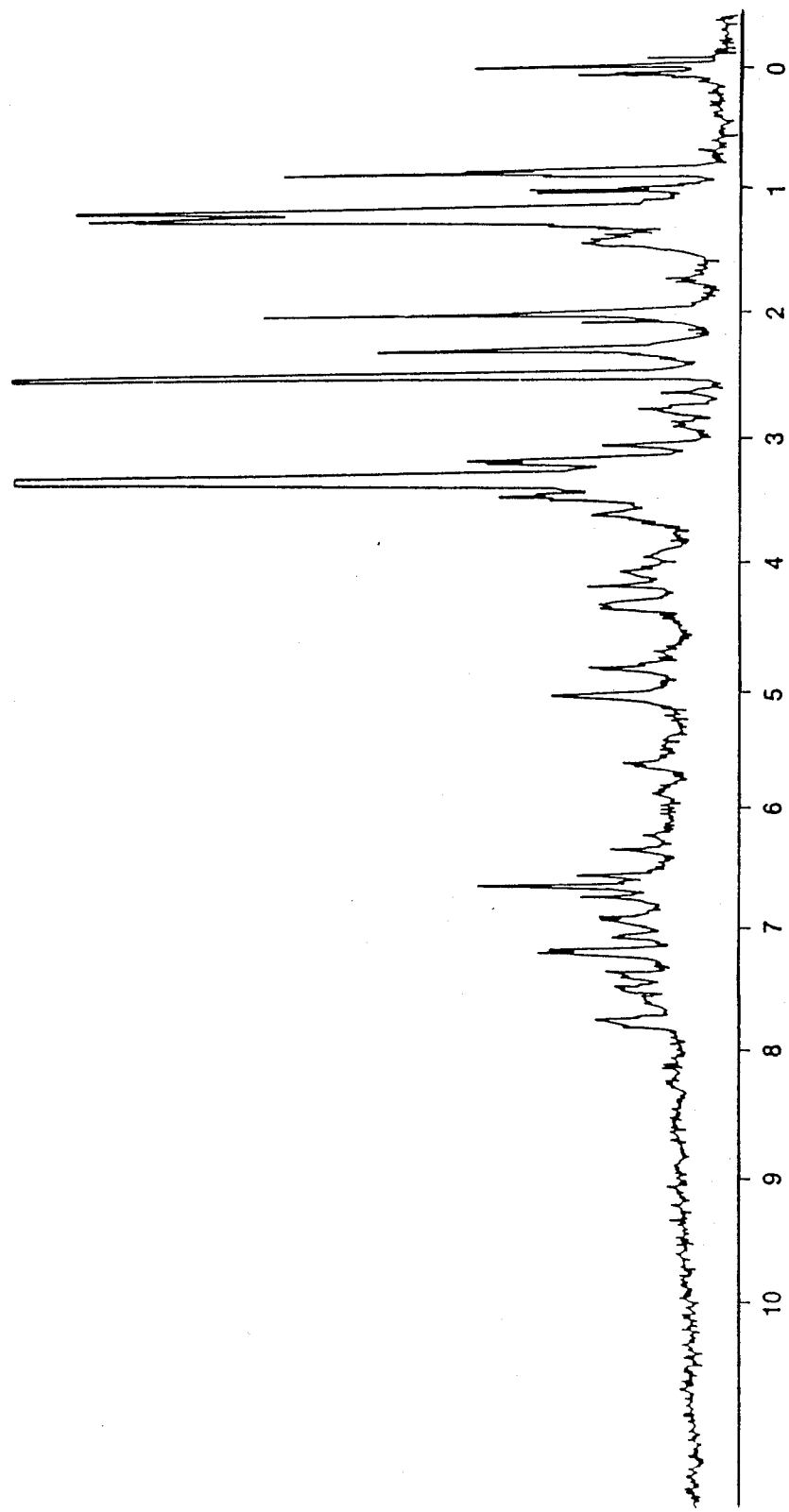

(C) $^1$H-NMR spectrum which is shown in FIG. 19 exhibits the following groups of signals (in ppm) in the 270 MHz $^1$H-NMR recorded in DMSO $d_6$ (hexadeuterodimethylsulfoxide) using TMS as the internal standard (0.00 ppm), (δ=ppm): 0.86, d's ($CH_3$);

1.15–1.22, m (CH$_2$)$_n$; 1.41, m (CH$_2$); 2.01, s (CH$_3$); 2.01, m (CH$_2$); 2.28, s (N-CH$_3$); 4.26–5.96, br (peptidic and aromatic CH's); 6.33–7.73 br (aromatic CH's and peptidic NH's).

br = broad
d = doublet
dd = doublet of doublets
m = multiplet
s = singlet
t = triplet (D) retention-time (R$_t$) of 1.15 relative to Teicoplanin A$_2$ component 2 (R$_t$=20.3 min) when analyzed by reverse phase HPLC under the following conditions:

column: Ultrasphere ODS (5 μm) Altex (Beckman) 4.6 mm (i.d.)×250 mm
pre-column: Brownlee Labs RP 18 (5 μm)

| eluent A: | CH$_3$CN | 10% | adjusted at pH 6.0 |
|---|---|---|---|
| | (2.5 g/l) NaH$_2$PO$_4$.H$_2$O | 90% | |
| eluent B: | CH$_3$CN | 70% | adjusted at pH 6.0 |
| | (2.5 g/l) NaH$_2$PO$_4$.H$_2$O | 30% | | elution: linear gradient from 5% to 60% of eluent B in eluent A, in 40 min
flow rate: 1.8 ml/min
U.V. detector: 254 nm
internal standard: Teicoplanin A$_2$ component 2 (Gruppo Lepetit S.p.A.)

(E) R$_f$ value relative to Teicoplanin A$_2$ component 2 of 0.62 in the following chromatographic system:

| 5% (w/v) aqueous Na$_2$SO$_4$ | 70 |
|---|---|
| acetonitrile | 30 | using silanized silica gel 60 F$_{254}$ Merck plates (layer thickness 0.25 mm) Visualization:
U.V. light
Yellow color with Pauly Reagent, i.e. diazotized sulfanilic acid (J. Chromatog. 20, 171 (1965), Z. Physiol. Chem. 292, 99, (1953))
Bioautography using B. subtilis ATCC 6633 on minimal Davis medium.

(F) MW of about 1758 desumed from a FAB-MS spectrum showing a cluster of peaks having the most intense peak at 1761. The operative conditions of the FAB-MS analysis were the following:

Instrument: VG Mod ZAB SE equipped with FAB gun Ion Tech
Conditions: Positive FAB, Xe Accelerating voltage, 8KV Matrix: Thioglycerol-glycerol 1/1 (v/v).

Figure 20:
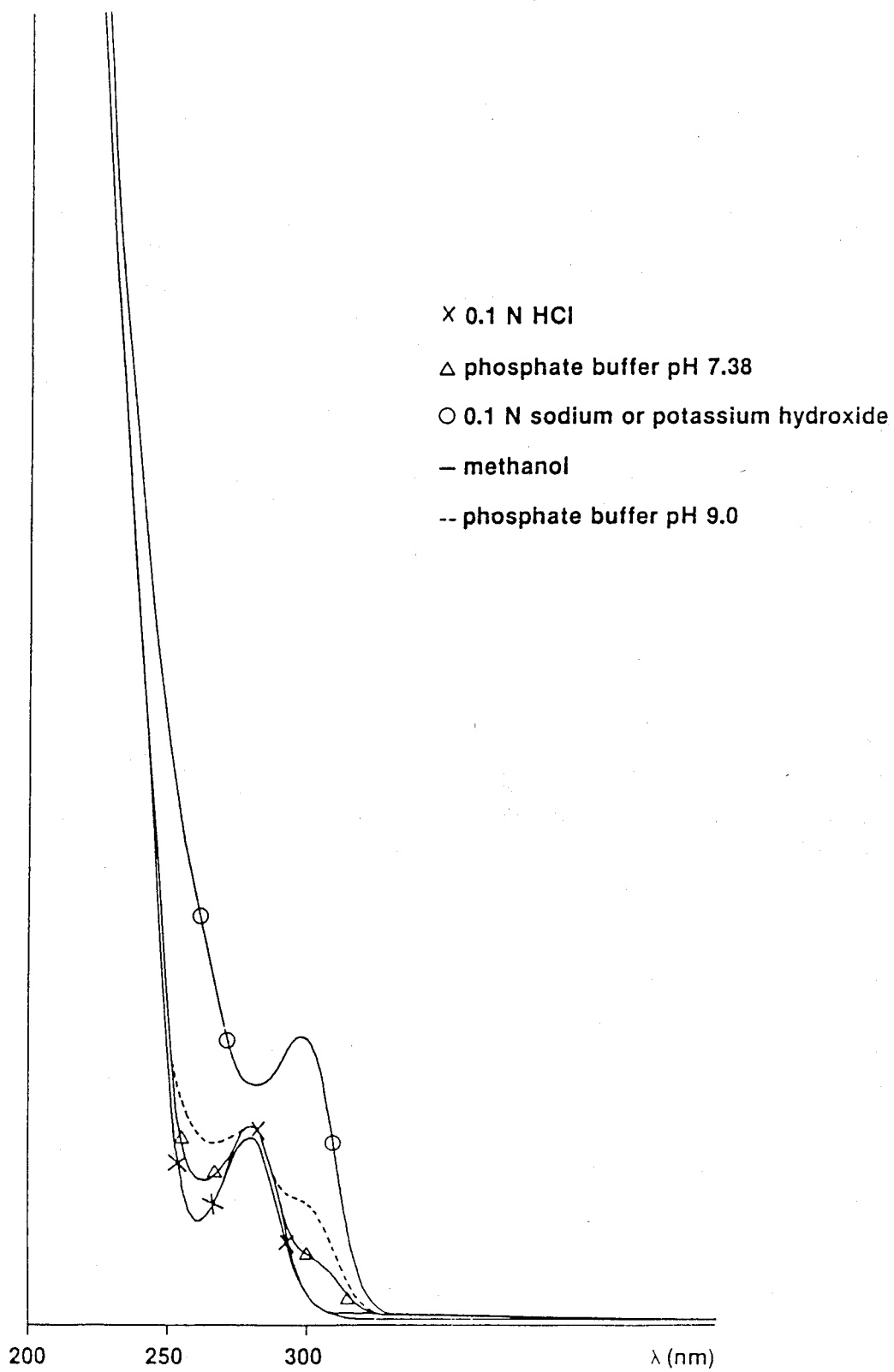

Physico-chemical characteristics of antibiotic A 40926 factor PB (A) ultraviolet absorption spectrum, shown in FIG. 20 of the accompanying drawings, exhibits the following absorption maxima:

| | | λ max (nm) |
|---|---|---|
| (a) | 0.1 N HCl | 282 |
| (b) | 0.1 N potassium hydroxide | 300 |
| (c) | phosphate buffer pH 7.38 | 282 |
| | | 300 (shoulder) |
| (d) | phosphate buffer pH 9.0 | 282 |
| | | 300 (shoulder) |

Figure 21:
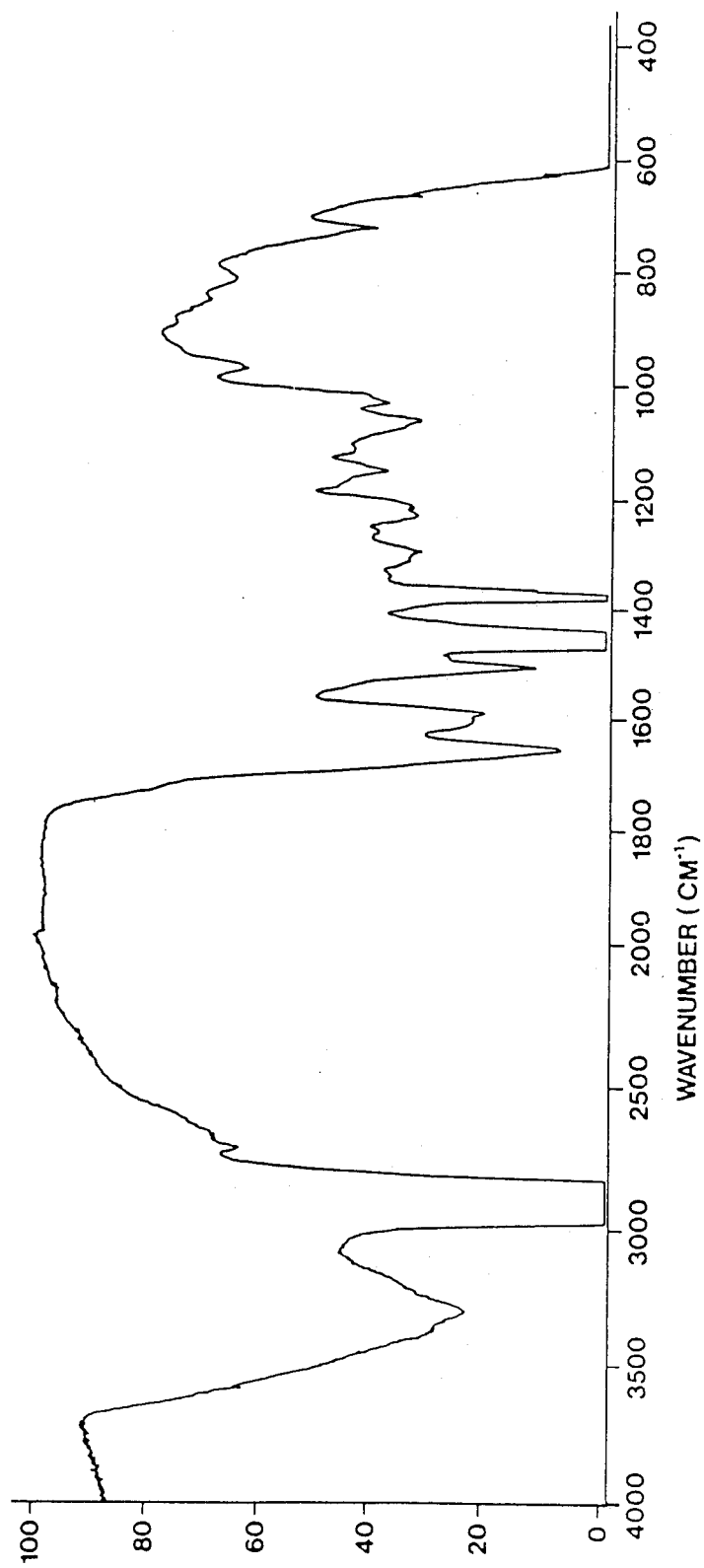

(B) infrared absorption spectrum which shown in FIG. 21 of the accompanying drawings exhibits the following absorption maxima (cm$^{-1}$): 3700–3100, 3000–2800 (nujol); 1760–1710; 1655; 1620–1560; 1605; 1480–1420 (nujol); 1375 (nujol); 1320–1270; 1230–1190; 1150, 1120–920; 845; 810; 720 (nujol)

Figure 22:
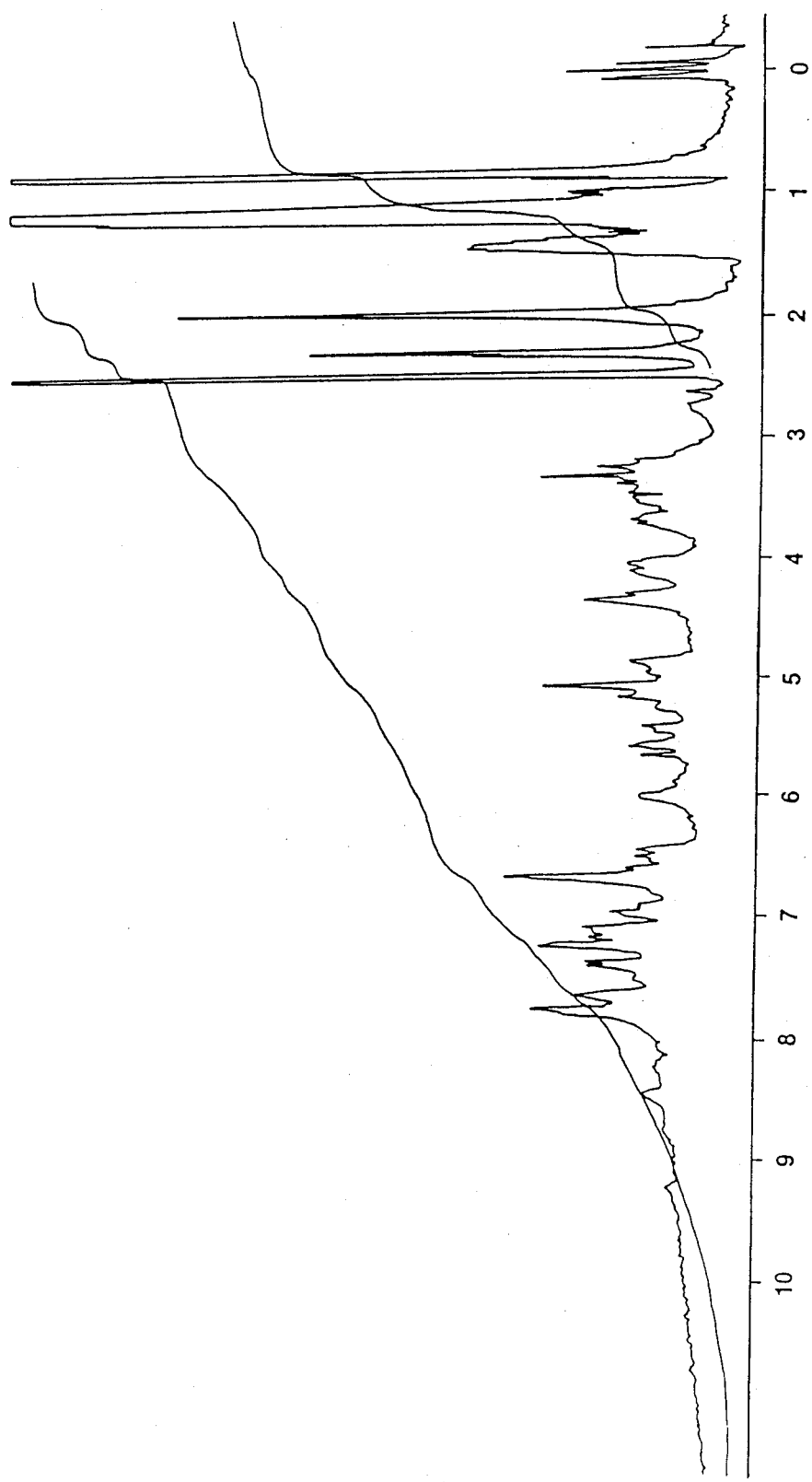

(C.1) $^1$H-NMR spectrum shown in FIG. 22 exhibits the following groups of signals (in ppm) at the 270 MHz in DMSO d$_6$ (hexadeuterodimethylsulfoxide) using TMS as the internal standard (0.00 ppm), (δ=ppm) multiplicity; (attribution): 0.84, d (isopropyl CH$_3$'s); 1.17, m (CH$_2$)$_n$; 1.43, m (CH$_2$), 1.99, s (CH$_3$); 2.01, m (CH$_2$); 2.31, s (N-CH$_3$); 2.79, dd (C-H); 3.70, m (C-H); 4.06–6.02, br (peptidic and aromatic CH's); 6.45–7.74, br (aromatic CH's and peptidic NH's); 9.19–9.99, br (peptidic NH's and phenolic OH's)

Figure 23:
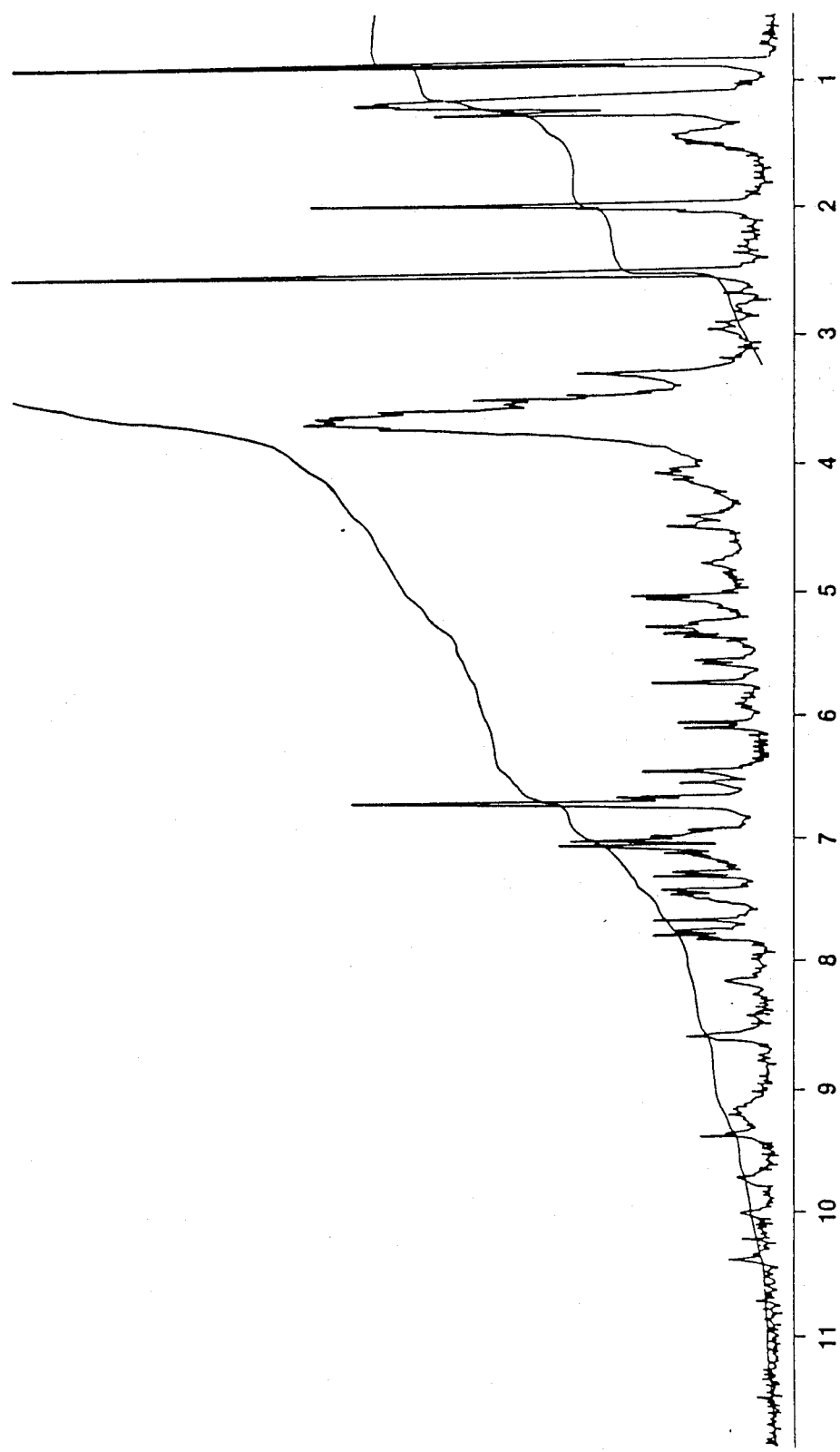

(C.2) $^1$H-NMR spectrum shown in FIG. 23 exhibits the following groups of signals (in ppm) at the 270 MHz in DMSO d$_6$ plus CF$_3$COOD using TMS as the internal standard (0.00 ppm), (δ=ppm) multiplicity; (attribution): 0.84, d (isopropyl CH$_3$'s); 1.13, m (CH$_2$)$_n$; 1.40, m (CH$_2$); 1.98, s (CH$_3$); 2.00, m (CH$_2$); 2.92, dd (C-H); 3.29–3.71, m (sugar C-H's); 4.07–6.09, s and m (peptidic and aromatic CH's); 6.45–7.83, s and m (aromatic CH's and peptidic NH's); 8.17–10.38 (peptidic NH's, phenolic OH's).

(D) retention times (R$_t$) of 1.27 and 1.32 relative to Teicoplanin A$_2$ component 2 (R$_t$=20.3 min) when analyzed by reverse phase HPLC under the following conditions:

column: Ultrasphere ODS (5 μm) Altex (Beckman) 4.6 mm (i.d.)×250 mm
pre-column: Brownlee Labs RP 18 (5 μm)

| eluent A: | CH$_3$CN | 10% | adjusted at pH 6.0 |
|---|---|---|---|
| | (2.5 g/l) NaH$_2$PO$_4$.H$_2$O | 90% | |
| eluent B: | CH$_3$CN | 70% | adjusted at pH 6.0 |
| | (2.5 g/l) NaH$_2$PO$_4$.H$_2$O | 30% | | elution: linear gradient from 5% to 60% of eluent B in eluent A, in 40 min
flow rate: 1.8 ml/min
U.V. detector: 254 nm
internal standard: Teicoplanin A$_2$ component 2 (Gruppo Lepetit S.p.A.)

(E) R$_f$ value relative to Teicoplanin A$_2$ component 2 of 0.53 in the following chromatographic system:

| 5% (w/v) aqueous Na$_2$SO$_4$ | 70 |
|---|---|
| acetonitrile | 30 | using silanized silica gel 60 F$_{254}$ Merck plates (layer thickness 0.25 mm) Visualization:
U.V. light
Yellow color with Pauly Reagent, i.e. diazotized sulfanilic acid (J. Chromatog. 20, 171 (1965), Z. Physiol. Chem. 292, 99, (1953))
Bioautography using B. subtilis ATCC 6633 on minimal Davis medium.

(F) MW of about 1772 desumed from a FAB-MS spectrum showing a cluster of peaks having the most intense peak at 1776. The operative conditions of the FAB-MS analysis were the following:

Instrument: VG Mod ZAB SE equipped with FAB gun Ion Tech
Conditions: Positive FAB, Xe Accelerating voltage, 8 KV Matrix: Thioglycerol-glycerol 1/1 (v/v).

Figure 24:
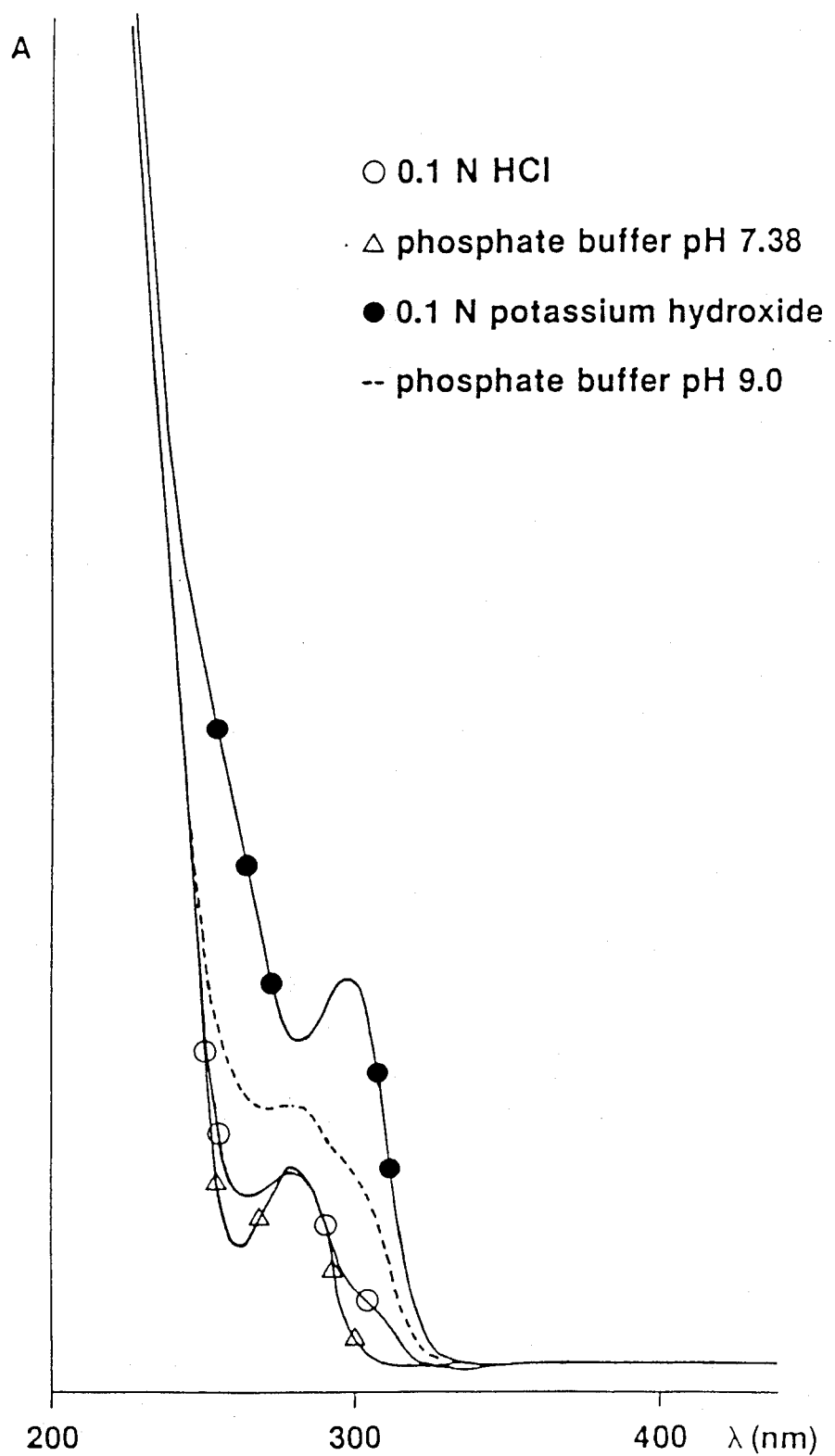

Antibiotic A 40926 mannosyl aglycon has the following characteristics (A) ultraviolet absorption spectrum, which is shown in FIG. 24 of the accompanying drawings, and exhibits the following absorption maxima:

|   |   | λ max (nm) |
|---|---|---|
| (a) | 0.1 N HCl | 280 |
| (b) | phosphate buffer pH 7.38 | 280 300(shoulder) |
| (c) | 0.1 N potassium hydroxide | 298 |
| (d) | phosphate buffer pH 9.0 | 282 300(shoulder) |

Figure 25:
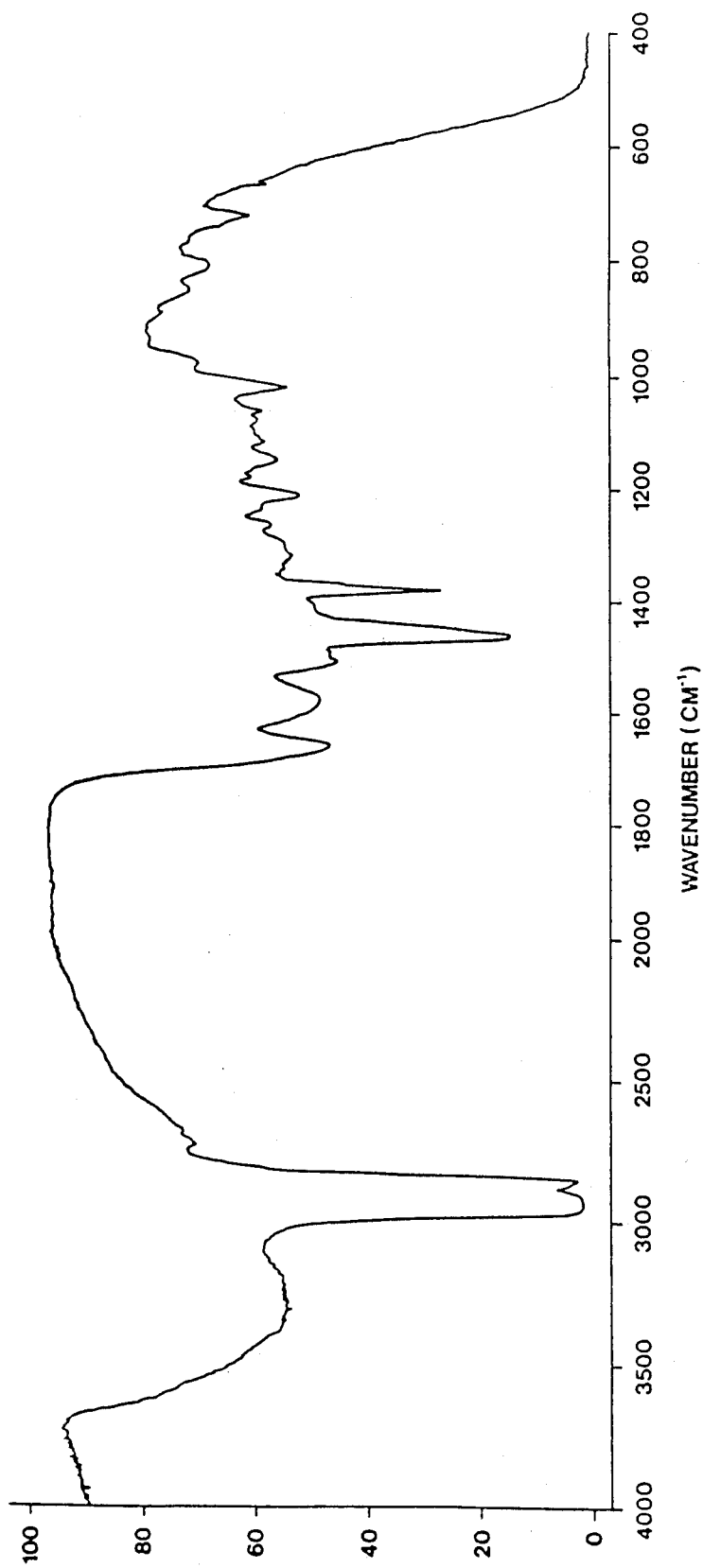

(B) infrared absorption spectrum which is shown in FIG. 25 of the accompanying drawings and exhibits the following absorption maxima (cm$^{-1}$): 3700–3100; 3000–2800 (nujol); 1655; 1620–1540; 1505; 1460 (nujol); 1375 (nujol) 1350–1250; 1210; 1150; 1020; 970; 850, 810

Figure 26:
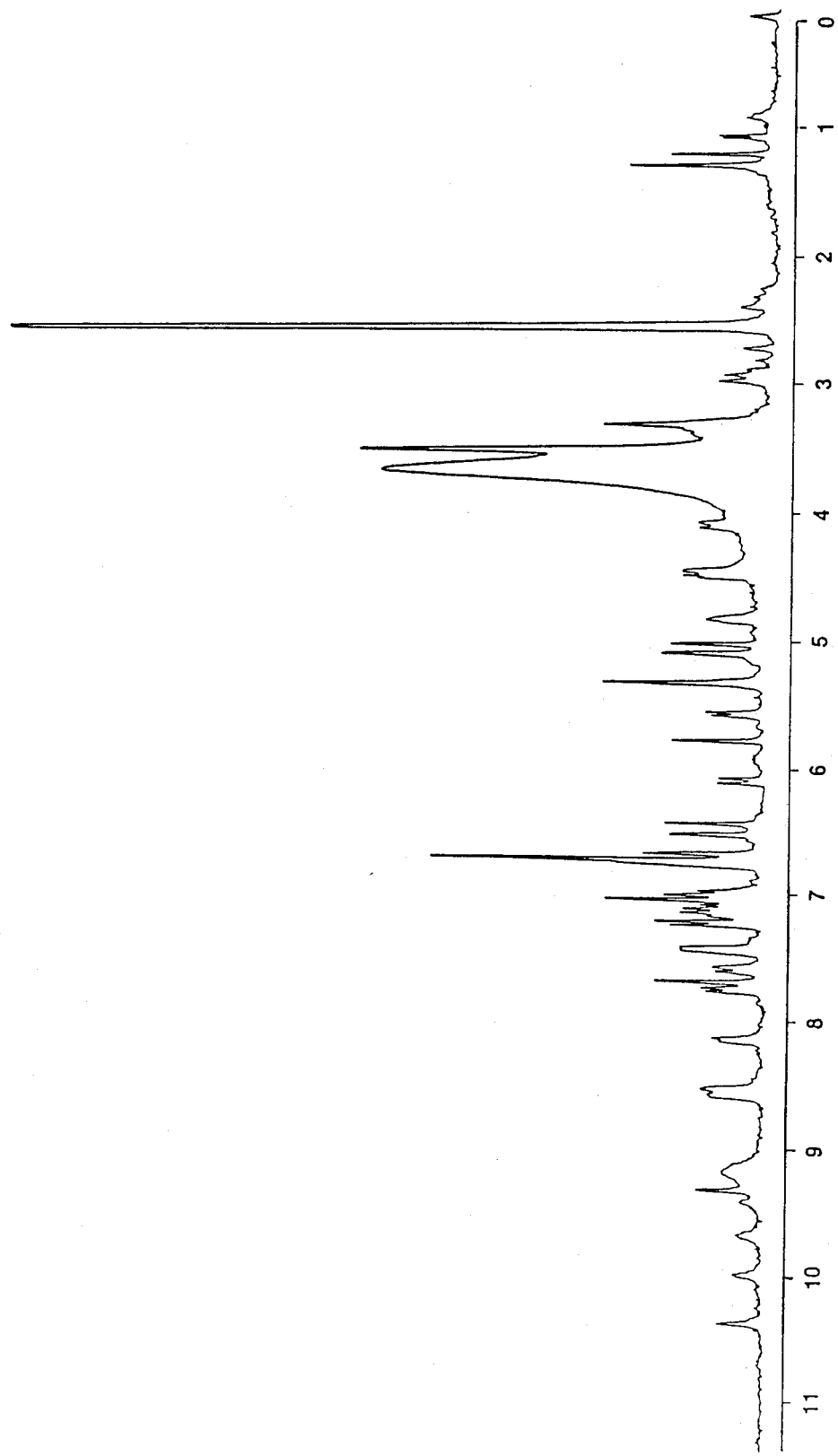

(C) $^1$H-NMR spectrum which is shown in FIG. 26 and exhibits the following groups of signals (in ppm) at 270 MHz recorded in DMSO d$_6$ (hexadeuterodimethylsulfoxide) plus CF$_3$COOH using TMS as the internal standard (0.00 ppm), (δ=ppm): 2.51, s (DMSOd$_5$); 2.50, s (NCH$_3$); 2.88, m (Z2); 3.30, m (Z'2); 4.08, m (X6); 4.44, d (X5); 4.49, d (X7); 4.83, m (X2); 5.02, s (4F); 5.08, s (Z6); 5.31, s (anomeric proton of mannose); 5.53, d (X4); 5.78, s (4B); 6.08, d (X3); 7.70, s (6B); 6.44–8.52 (aromatic and peptidic NH's)

d=doublet; m=multiplet; s=singlet (D) retention-time (R$_t$) of 1.18 relative to antibiotic L 17054 (TA3-1) (R$_t$=8.78 min), when analyzed by reverse phase HPLC under the following conditions:

column: Ultrasphere ODS (5 μm) Altex (Beckman) 4.6 mm (i.d.)×250 mm
pre-column: Brownlee Labs. RP 18 (5 μm)

| eluent A: | CH$_3$CN | 10% | adjusted at pH 6.0 |
|---|---|---|---|
|  | (2.5 g/l) NaH$_2$PO$_4$.H$_2$O | 90% |  |
| eluent B: | CH$_3$CN | 70% | adjusted at pH 6.0 |
|  | (2.5 g/l) NaH$_2$PO$_4$.H$_2$O | 30% |  | elution: linear gradient from 5% to 60% of eluent B in eluent A, in 40 min
flow rate: 1.6 ml/min
U.V. detector: 254 nm
internal standard: antibiotic L 17054 (TA3-1) (Gruppo Lepetit S.p.A.)

(E) R$_f$ value of 0.39 in the following chromatographic system:

| 1 M NaCl containing 5 g/l of NaH$_2$PO$_4$.H$_2$O | 70 |
|---|---|
| acetonitrile | 30 | adjusted to pH 6.0, using silanized silica gel 60 F$_{254}$ Merck plates (layer thickness 0.25 mm) Visualization: U.V. light
Yellow color with Pauly Reagent, i.e. diazotized sulfanilic acid (J. Chromatog. 20, 171 (1965), Z. Physiol. Chem. 292, 99, (1953))

Bioautography using B. subtilis ATCC 6633 on minimal Davis medium.

(F) A fast atom bombardment (FAB) mass spectrum with M+H$^\oplus$ at about 1374.

The following Examples further illustrate the invention and, as such, should not be construed as limiting its scope.

EXAMPLE 1

Preparation of antibiotic A 40926 N-acylaminoglucuronyl aglycon complex AB and antibiotic A 40926 aglycon (a) Antibiotic A 40926 complex AB (as prepared substantially by following the procedure of Preparation 3) (750 mg) is dissolved in 150 ml of a mixture dimethylsulfoxide (DMSO) /37% (w/w) hydrochloric acid (HCl), 9:1 (v/v) and the reaction mixture is heated to about 65° C. The reaction course is monitored by HPLC and when the starting materials are completely reacted (after about 5 h) the reaction is quenched with cold water (600 ml) and the pH of the resulting mixture is adjusted to about 7.5. This mixture contains a mixture of the compounds of the title which is separated into its two major components by affinity chromatography according to the following procedure:

(b) The aqueous mixture obtained above (750 ml) is applied to a Sepharose-D-Alanyl-D-Alanine chromatography column prepared as described in Preparation 8 (100 ml of swollen resin in 10 mM TRIS.HCl pH 7.5 buffer; bed height 10 cm). 0.05 M NH$_4$OH.HCl pH 7.5 containing 2 M NaCl (200 ml) (buffer B) is passed through the column; then A 40926 aglycon is selectively removed from the column by eluting with 0.05 M NH$_4$OH.HCl pH 9.5 containing 2 M NaCl (1599 ml) (buffer C). N-Acylaminoglucuronyl aglycon complex AB is then eluted with 0.1 M aqueous ammonia (buffer D). The eluted fractions are then pooled according to their antibiotic content adjusted to about pH 7.5 and each antibiotic containing solution is chromatographed on a Sepharose-D-Alanyl-D-Alanine column (100 ml of swollen resin in 10 mM TRIS.HCl pH 7.5 buffer; bed height 10 cm). Distilled water is passed through the column until the inorganic salts are washed out. The antibiotics are then eluted with 0.1 N aqueous ammonia. These eluted fractions, pooled according to their antibiotic content, are concentrated to a small volume under reduced pressure by azeotropical distillation with n-butanol and lyophilized yielding respectively 201 mg of N-acylaminoglucuronyl aglycon complex AB and 236 mg of A 40926 aglycon.

By repeating the same experiment described above but using a mixture DMSO/37% HCl 95:5 at about 40° C. for about 5 days the yield in N-acylaminoglucuronyl aglycon complex AB increases of about 15% while the yield in A 40926 aglycon is reduced accordingly.

By repeating these experiments starting from antibiotic A 40926 complex, antibiotic A 40926 factor A, antibiotic A 40926 factor B, antibiotic A 40926 factor B$_0$, antibiotic A 40926 factor PA and antibiotic A 40926 factor PB substantially the same results are obtained (i.e. the yields vary in the range ±5%).

In particular, starting from antibiotic A 40926 factor A, or factor PA, the product which is obtained is antibiotic A 40926 N-acylaminoglucuronyl aglycon factor A, while starting from antibiotic A 40926 factor PB, or factor B$_0$ the obtained product is antibiotic A 40926 N-acylaminoglucuronyl aglycon factor B$_0$. From antibiotic A 40926 factor B a mixture of antibiotic A 40926 N-acylaminoglucuronyl aglycon factors $B_0$ and $B_1$ is obtained which may be separated by HPLC.

EXAMPLE 2

Separation of antibiotic A 40926 N-acylaminoglucuronyl agalycon factors A, $B_0$ and $B_1$ 20 mg of antibiotic A 40926 N-acylaminoglucuronyl aglycon complex AB is dissolved in 1 ml of 18 mM sodium phosphate buffer pH 6.0 containing 10% of acetonitrile.

The solution was injected into a HPLC preparative column (7 mm id×250 mm) Lichrosorb RP18 silanized silica gel (Merck Co.) having 7 micrometer particle size.

The column is eluted at a flow rate of 5 ml/min of phase A and B with a linear gradient from 10% to 55% of phase A in 55 min.

Phase A: 18 mM sodium phosphate/$CH_3CH$ 30/70 brought to pH 6.0 with NaOH.

Phase B: 18 mM sodium phosphate/$CH_3CH$ 90/10 brought to pH 6.0 with NaOH.

The column eluates UV adsorption at 254 nm is recorded and the elution fractions having omogeneous content are collected, separating three groups of eluates containing antibiotic A 40926 N-acylaminoglucuronyl aglycon factors A, $B_0$ and $B_1$ respectively.

The eluates containing the purified antibiotic A 40926 N-acylaminoglucuronyl aglycon factors of 11 subsequent chromatographic runs are pooled and desalted as usual by loading them on a column of 5 ml swollen sepharose-D-Ala-D-Ala (c.f. preparation 8). After removing the salts with 10 ml of 1 mM HCl followed by 5×10 ml of distilled water, the antibiotic is eluted with 5×10 ml of 1% w/v aqueous ammonia. The ammonia eluates are then separately collected and freeze-dried yielding 15 mg of antibiotic A 40926 N-acylaminoglucuronyl aglycon factor A, 51 mg of antibiotic A 40926 N-acylaminoglucuronyl aglycon factor $B_0$ and 3 mg of antibiotic A 40926 N-acylaminoglucuronyl aglycon factor $B_1$ whose physico-chemical data and chemical formula are reported above in the description.

EXAMPLE 3

Selective preparation of antibiotic A 40926 aglycon
(a) From antibiotic A 40926 complex AB Antibiotic A 40926 complex AB (as prepared substantially by following the procedure of Preparation 3) (750 mg) is dissolved in 150 ml of a mixture dimethylsulfoxide/37% hydrochloric acid, 9:1 (v/v) and the reaction mixture is heated to about 80° C. The reaction course is monitored by HPLC and when the starting materials are completely reacted (after about 3 h) the reaction is quenched with cold water (600 ml) and the pH of the resulting mixture is adjusted to about 7.5. This mixture (750 ml) contains antibiotic A 40926 aglycon which is separated by affinity chromatography on a Sepharose-D-Alanyl-D-Alanine chromatography column prepared as described in Preparation 8 (100 ml of swollen resin in 10 mM TRIS.HCl pH 7.5; bed height 10 cm). 0.05 M $NH_4OH.HCl$ pH 7.5 containing 2 M NaCl (200 ml) (buffer B) is passed through the column; then A 40926 aglycon is selectively removed from the column by eluting with 0.05 M $NH_4OH.HCl$ pH 9.5 containing 2 M NaCl (1599 ml) (buffer C). The eluted fractions are then pooled according to their antibiotic content, adjusted to about pH 7.5 and chromatographed on Sepharose-D-Alanyl-D-Alanine column (100 ml of swollen resin in 10 mM TRIS.HCl pH 7.5; bed height 10 cm). Distilled water is passed through the column until the inorganic salts are washed out. A 40926 aglycon is eluted with 0.1 N aqueous ammonia. These eluates are concentrated to a small volume under reduced pressure by azeotropical distillation with n-butanol and lyophilized yielding 530 mg of A 40926 aglycon.

Preparation of the starting materials

Preparation 1

Fermentation of Actinomadura sp.ATCC 39727

A culture of antibiotic A 40926 producing strain (Actinomadura sp. ATCC 39727) is grown on oatmeal agar slant for 2–3 weeks at 28° C. and used to inoculate a 500 ml Erlenmeyer flask containing 100 ml of medium composed of 0.5% meat extract, 0.5% autolyzed yeast, 0.5% peptone, 0.3% casein hydrolyzed, 2% glucose, 0.15% NaCl (pH 7.5 before sterilization).

The flask is incubated at 28° C. on a rotary shaker at 200 rpm for about 72 h and then the culture is transferred to a fermentor containing 4 l of the above medium. This culture is grown at 28° C. for about 72 h with air-flow of about two liters per minute and stirring at about 900 rpm. Then, it is used to inoculate a 200 l fermentor of the same medium. This fermentor is aerated with 100 l per minute of sterile air and is stirred at 250 rpm at about 28° C. The antibiotic production is monitored by the paper-disc agar diffusion method using *B. subtilis* on a minimal medium as the test organism. The maximum activity is obtained after 72–96 h.

Preparation 2

Recovery of antibiotic A 40926

(A) The above fermentation broth is cooled to 4° C., brought to pH 9.5 and stirred. After about 1 h it is filtered and the filtrate is adjusted to pH about 3.5 with an aqueous mineral acid. The mixture is stirred for 30 min at 4° C. and then filtered with (Hyflo-FloMa ®) filter aid. The clear filtrate is discharged and the filter cake is suspended in deionized water, adjusted to pH about 8.5, stirred and then filtered. The recovered cake is subjected to the same procedure. The pooled filtrates contain antibiotic A 40926.

(B) Swollen D-Ala-D-Ala-$\epsilon$-aminocaproyl-Sepharose modified matrix (2 l) is added to the fermentation broth obtained according to Preparation 1 (after filtering it and bringing the pH of the clear filtrate to about 8.5) or to the pooled filtrate obtained according to the above Preparation 2 A). After stirring overnight at room temperature, the resin is recovered by filtration and is washed sequentially with about 2×10 l of 0.45 mM HCl-TRIS buffer pH 7.5 (TRIS=2-amino-2-hydroxymethyl-1,3-propanediol) which contains 5% (w/v) NaCl and then with distilled water (4×20 l). The A 40926 antibiotic is eluted from the resin with 1% (w/v) ammonia hydrate (2×20 l). The eluates are left overnight at room temperature and then concentrated to a small volume (about 2.5 l). Water is eliminated by azeotropical distillation with n-butanol. Petroleum ether is then added, precipitating 3.4 g of crude antibiotic A 40926 complex.

Preparation 3

Purification of antibiotic A 40926 complex AB

Crude antibiotic A 40926 complex obtained essentially following the procedure of the above Preparation 2, (750 mg; HPLC titre 70%) is dissolved in 400 ml of water, adjusted to pH 7.5 and filtered. The filtrate is then subjected to affinity chromatography on a D-Ala-D-Ala-ε-aminocaproyl-Sepharose column (50 ml of swollen resin; bed height=5 cm). The column, equilibrated with 0.16% (w/v) ammonia containing 2 M NaCl adjusted to pH 7.5 with HCl, is developed sequentially with the following three buffer solutions:

buffer A: 0.16% (w/v) ammonia containing 2M NaCl adjusted to pH 7.5 with HCl, (2.6 column bed volumes);
buffer B: 0.16% (w/v) ammonia containing 2M NaCl adjusted to pH 9.5 with HCl (16 column bed volumes);
buffer C: 1% (w/v) aqueous ammonia pH 11.4 (2.6 column bed volumes).

Buffer C elutes antibiotic A 40926 complex AB in a single fraction. This eluted fraction is adjusted to pH 7.0 and reapplied to the same affinity column buffered with with 10 mM TRIS-HCl pH 7.0. The column is washed with distilled water until desalting is complete.

The antibiotic is then eluted with 2 column bed volumes of 0.39% (w/v) aqueous ammonia pH 11.0.

The eluted fractions are concentrated to a small aqueous mixture and then freeze-dried. Pure antibiotic A 40926 complex AB (374 mg) is obtained.

Preparation 4

Isolation of antibiotic A 40926 factor A and B (A) Antibiotic A 40926 complex as obtained according to Preparation 2 (3.3 g) or antibiotic A 40926 complex AB as obtained according to Preparation 3 (2.3 g) is suspended in 0.5 l of water, stirred and then filtered. The clear filtrate is applied to a silanized silica gel column (200 g; bed h 18 cm; silanized Silicagel 60; 70–230 mesh, Merck Inc.) pre-equilibrated with solution A (0.001 M aqueous sodium EDTA containing 0.25% (w/v) $NaH_2PO_4.H_2O$ and 2.5% (w/v) NaCl adjusted to pH 6.0 with NaOH). The column is eluted with a linear gradient from 0% to 40% (v/v) of acetonitrile in solution A with a total volume of about 7 l in about 48 h. Fractions of about 15.5 ml are collected and assayed by bioassay on Bacillus subtilis and analyzed by HPLC. Fractions having a similar antibiotic content are pooled. Fractions No. 310–330 and No. 348–365 contained the antibiotic substances denominated, respectively, A 40926 factor A and A 40926 factor B.

(B) The pooled fractions containing the single A 40926 factors A and B are concentrated under reduced pressure to remove acetonitrile, diluted with water (about twice the volume of the initial solutions) and applied to a silanized silica gel column of the type described above (volume of the swollen matrix: 50 ml; bed height of 15 cm). The column is washed with deionized water until desalting is complete and finally developed with acetonitrile/water 60:40 (v/v).

The eluted fractions are concentrated under reduced pressure and the residues are freeze-dried to obtain 134 mg of antibiotic A 40926 factor A from the first group of eluted fractions (fractions 310–330 above) and 206 mg of A 40926 factor B from the second group of eluted fractions (fractions 348–365, above).

Preparation 5

Isolation of antibiotic A 40926 factor PA and factor PB

By essentially following the procedure of Preparation 2A and the first steps of the procedure of Preparation 2B, the antibiotic linked to the resin is eluted with 1% (w/v) ammonia hydrate (2×20 l). The eluates are adjusted to pH 7.8 with sulfuric acid and concentrated to a small volume under vacuum by axeotropical distillation with n-butanol to obtain an aqueous concentrate which is then filtered on paper. The recovered filtrate contains antibiotic A 40926 factor PA, A 40926 factor PB and minor amounts of A 40926 factor A and factor B (HPLC).

A sample (10 ml) of this aqueous concentrate containing about 50 mg/ml of pure antibiotic A 40926 complex (HPLC analysis) is filtered on 5 micrometer pore-size filter (Acrodisc ®; Gelman Science Inc.) and then applied to a stainless steel column (diameter=2 cm) containing 20 g of an octadecyl silyl reverse-phase silica gel (Lichrisorb RP 18, Merck Inc.; particle size 10 μm). The silica gel is then packed under moderate pressure (nominal pressure about 14 bar) in a stainless steel column of a Chromatospac Modulprep apparatus (Joben Yvon, France) and equilibrated with a mixture consisting of acetonitrile and 18 mM sodium phosphate buffer pH 6.0), 25:75 (v/v). The elution is carried out using the same solvent mixture used for the equilibration at a flow rate of about 10.5 ml/min. The eluate is monitored by bioassay on Bacillus subtilis and by HPLC.

Those fractions having similar antibiotic content are pooled and the homogeneous fractions of 5 chromatographic runs are concentrated to evaporate the organic solvent.

The resulting solution is diluted with aqueous 1M sodium chloride to twice the original volume and is applied to a silanized silica gel column (50 g; bed height 5 cm; Silanized silica gel 60; Merck Inc.) equilibrated with water.

The column is washed with deionized water until desalting is complete (no AgCl precipitation in the eluates after addition of aqueous $AgNO_3$) and then eluted with acetonitrile:water 1:1 (v/v). The eluates having similar antibiotic content (HPLC analysis) are pooled, concentrated to a small volume by azeotropical distillation with n-butanol to obtain an aqueous phase which is then freeze-dried. Yields:

antibiotic A 40926 factor PA: 55 mg
antibiotic A 40926 factor PB: 51 mg
antibiotic A 40926 factor A: 38 mg
antibiotic A 40926 factor $B_0$: 33 mg Preparation 6

Alternative method for isolating antibiotic A 40926 factor B

The pooled concentrate of two preparations made according to Preparation 2 (the last step) is filtered and the filtrate is applied to a silanized silica gel chromatographic column; (400 g; bed h 30 cm; Silicagel 60, 70–230 mesh, Merck Inc.) pre-equilibrated with water.

The column is rinsed with water (6 l) and the adsorbed antibiotic is eluted with acetonitrile/water according to the following sequence:

2.7 l 5% (v/v) acetonitrile in water
1.6 l 10% (v/v) acetonitrile in water
2.97 l 15% (v/v) acetonitrile in water
3.15 l 20% (v/v) acetonitrile in water Fractions of about 18 ml are collected.

The activity of the eluted fractions is tested by paper-disc bioassay on susceptible microorganisms such as B. subtilis and analyzed by HPLC. Fractions with similar antibiotic content are pooled (fractions 472–526) and concentrated under reduced pressure. n-Butanol is added to this concentrate to azeotropically remove water. The butanolic solution which remains is in turn concentrated to a small volume to precipitate antibiotic A 40926 factor B (1.4 g). This product is wshed with petroleum ether under stirring and collected by filtration (three times). Upon drying under vacuum 760 mg of A 40926 factor B are obtained.

By resubmitting antibiotic A 40926 factor B to the above column chromatography a product (540 mg) antibiotic A 40926 factor $B_0$ is obtained which has the same physico-chemical characteristics reported above for antibiotic A 40926 factor B except that it shows only a peak at HPLC analysis, namely the peak with retention time of 1.22 relative to Teicoplanin $A_2$ component 2. The other compound, which is eluted subsequently, has the retention time of 1.27 in the above HPLC system and has been named antibiotic A 40926 factor $B_1$. It is isolated by working up as above (yield = 15 mg).

Preparation 7

Transformation of antibiotic A 40926 factor PA and antibiotic A 40926 factor PB into antibiotic A 40926 factor A and factor B, respectively Antibiotic A 40926 factor PA and antibiotic A 40926 factor PB (50 mg) are separately dissolved in 2.5 ml of aqueous 1% (w/v) $NH_4OH$ and the resulting solutions are kept for about 24 h at room temperature with stirring.

Antibiotic A 40926 factor A is obtained from the solution originally containing antibiotic A 40926 factor PA, and antibiotic A 40926 factor B is obtained from the solution originally containing antibiotic A 40926 factor PB by removing water by azeotropic distillation with n-butanol, precipitating with ethyl ether and collecting the precipitate by filtration (yield about 75%).

Preparation 8

Preparation of D-Ala-D-Ala-Sepharose (a): Activation of Sepharose with epichlorohydrin One liter of Sepharose 4B (Pharmacia Fine Chemicals), filtered on a porous glass filter and washed with demineralized water, is added to 1.2 l of NaOH N/1 under gentle stirring at room temperature. After the addition of 100 ml of epichlorohydrin the mass is maintained agitated at about 20° C. by external cooling with cold water for 24 hours. The suspension is filtered and the solid is washed with demineralized water (about 5 l) to neutral pH.

(b): Preparation of Sepharose $\epsilon$-ACA-D-Ala-D-Ala

To a solution of 17 g (62.2 mmoles) of $\epsilon$-ACA-D-Ala-D-Ala in 200 ml of water brought to pH 11 with 20% NaOH, about 500 ml of Sepharose 4B derivatized with epichlorohydrin (total epoxide content about 15.5 m.equivalents) are added under mechanical stirring.

The suspension is stirred at pH 11 and at room temperature for about 2 days (until the test used to measure the epoxide content is negative) filtered and washed with 300 ml of water. The filtered resin is washed again with water (about 3 l) until neutral pH obtaining 460 ml of Sepharose $\epsilon$-ACA-D-Ala-D-Ala.

We claim:

1. An antibiotic substance selected from antibiotic A 40926 N-acylaminoglucuronyl aglycon complex AB, antibiotic A 40926 N-acylaminoglucuronyl aglycon factor A, antibiotic A 40926 N-acylaminoglucuronyl aglycon factor $B_0$, antibiotic A 40926 N-acylaminoglucuronyl aglycon factor $B_1$, antibiotic A 40926 aglycon and the addition salts thereof, which has the following characteristics:

Antibiotic A 40926 N-acylaminoglucuronyl aglycon complex AB (in the non-addition salt form):

(A) ultraviolet absorption spectrum which exhibits the following absorption maxima:

|  | $\lambda$ max (nm) |
|---|---|
| (a) 0.1 N HCl | 282 |
| (b) phosphate buffer pH 7.4 | 282 |
|  | 310 (shoulder) |
| (c) 0.1 N KOH | 302 |

(B) infrared absorption spectrum which exhibits the following absorption maxima ($cm^{-1}$): 3700–3100; 3000–2800 (nujol); 1650; 1620–1550; 1500; 1460 (nujol); 1375 (nujol); 1300; 1250–1180; 1150; 1060; 1010; 970; 930; 840, 820

(C) $^1$H-NMR spectrum which exhibits the following groups of signals (in ppm) at 270 MHz recorded in DMSO $d_6$ (hexadeuterodimethylsulfoxide) plus $CF_3COOH$ using TMS as the internal standard (0.00 ppm), ($\delta$=ppm): 0.84, d and t [isopropylic $CH_3$'s and terminal $CH_3$]; 1.14, m [$(CH_2)_n$]; 1.44, m [$-CH_2$-C-CO and isopropylic CH]; 2.00, t [$-CH_2$-(CO)]; 2.5 s ($DMSOd_5$); 2.5 s ($N-CH_3$); 2.93, m [CH, (Z2)]; 3.33, m [CH, (Z'2)]; 3.20–3.80, m [sugar CH's]; 5.34, d [anomeric proton of acylaminoglucuronyl acid]; 4.10 m (X6); 4.33 d, (X5); 4.43 d (X7); 4.9 m (X2); 5.1 (4F and Z6); 5.4 s (X1); 5.58 d (X4); 5.7 s (4B); 6.06 d (X3); 7.73 s (6B); 6.26–8.42 s and m [aromatic CH's and peptidic NH's]; 8.70–10.5, br s [phenolic OH's and $NH_2^+$]

br = broad
d = doublet
m = multiplet
s = singlet
t = triplet (D) Retention times ($R_t$) of 1.20 and 1.30 relative to Teicoplanin $A_2$ component 2 ($R_t$=20.3 min) when analyzed by reverse phase HPLC under the following conditions:

column: Ultrasphere ODS (5 μm) Altex (Beckman) 4.6 mm (i.d.)×250 mm
pre-column: Brownless Labs RP 18 (5 μm)

| eluent A: | $CH_3CN$ | 10% | adjusted at |
|---|---|---|---|
|  | (2.5 g/l) $NaH_2PO_4.H_2O$ | 90% | pH 6.0 |
| eluent B: | $CH_3CN$ | 70% | adjusted at |
|  | (2.5 g/l) $NaH_2PO_4.H_2O$ | 30% | pH 6.0 | elution: linear gradient from 5% to 60% of eluent B in eluent A, in 40 min
flow rate: 1.8 ml/min
U.V. detector: 254 nm
internal standard: Teicoplanin $A_2$ component 2 (Gruppo Lepetit S.p.A.)

(E) acid functions capable of forming salts
(F) amino function capable of forming salts
(G) no mannose unit linked to the core moiety.

Antibiotic A 40926 N-acylaminoglucuronyl aglycon factor A (in the non-addition salt form)

(A) ultraviolet absorption spectrum which exhibits the following absorption maxima:

| | λ max (nm) |
|---|---|
| (a) 0.1 N HCl | 282 |
| (b) phosphate buffer pH 7.4 | 282 |
| | 310 (shoulder) |
| (c) 0.1 N KOH | 302 |

(B) infrared absorption spectrum which exhibits the following absorption maxima (cm$^{-1}$): 3700–3000; 3000–2800; 1650; 1585; 1505; 1460 (nujol); 1375 (nujol); 1295; 1230; 1210; 1150; 1070; 1060; 1010; 845; 820; 720 (nujol)

(C) $^1$H-NMR spectrum which exhibits the following groups of signals (in ppm) at 270 MHz recorded in DMSO d$_6$ (hexadeuterodimethylsulfoxide) using TMS as the internal standard (0.00 ppm), (δ=ppm): 0.85 t (terminal CH$_3$); 1.0÷1.3 (aliphatic CH$_2$'s); 1.42 m ((OC-C)CH$_2$); 2.00 t ((CO)CH$_2$); 2.35 s (NCH$_3$); 2.49 s (DMSOd$_5$); 2.82 m (Z2); 2.8÷3.8 (sugar protons and Z'2); 4.12 m (X6); 4.56 s (X1); 4.34 d (X5); 4.41 d (X7); 4.96 m (X2); 5.08–5.12 (4F and Z6); 5.40 d (anomeric proton of acylaminoglucuronic acid); 5.58 d (X4); 5.74 s (4B); 6.05 d (X3); 7.75 s (6B); 6.25–8.40 s, d and m (aromatic CH's and peptidic NH's)

(D) Retention time (R$_t$) of 1.20 relative to Teicoplanin A$_2$ component 2 (R$_t$=20.3 min) when analyzed by reverse phase HPLC under the following conditions:

column: Ultrasphere ODS (5 μm) Altex (Beckman) 4.6 mm (i.d.)×250 mm
pre-column: Brownlee Labs RP 18 (5 μm)

| eluent A: | CH$_3$CN | 10% | adjusted at |
| | (2.5 g/l) NaH$_2$PO$_4$.H$_2$O | 90% | pH 6.0 |
| eluent B: | CH$_3$CN | 70% | adjusted at |
| | (2.5 g/l) NaH$_2$PO$_4$.H$_2$O | 30% | pH 6.0 | elution: linear gradient from 5% to 60% of eluent B in eluent A, in 40 min
flow rate: 1.8 ml/min
U.V. detector: 254 nm
internal standard: Teicoplanin A$_2$ component 2 (Gruppo Lepetit S.p.A.)

(E) Molecular weight of about 1554 as determined by FAB-MS
(F) acid functions capable of forming salts
(G) amino functions capable of forming salts
(H) no mannose unit linked to the core moiety.

Antibiotic A 40926 N-acylaminoglucuronyl aglycon factor B$_0$ (in the non-addition salt form)

(A) ultraviolet absorption spectrum which exhibits the following absorption maxima:

| | λ max (nm) |
|---|---|
| (a) 0.1 N HCl | 282 |
| (b) phosphate buffer pH 7.4 | 282 |
| | 310 (shoulder) |
| (c) 0.1 N KOH | 302 |

(B) infrared absorption spectrum which exhibits the following absorption maxima (cm$^{-1}$): 3700–3100; 3000–2800 (nujol); 1650; 1585; 1505; 1460 (nujol); 1375 (nujol); 1295; 1230; 1210; 1150; 1060; 1010; 980; 840; 820; 720 (nujol)

(C) $^1$H-NMR spectrum which exhibits the following groups of signals (in ppm) at 270 MHz recorded in DMSO d$_6$ (hexadeuterodimethylsulfoxide) using TMS as the internal standard (0.00 ppm), (δ=ppm): 0.84, d (isopropylic CH$_3$'s); 1.0÷1.3 (aliphatic CH$_2$'s); 1.3÷1.6 ((OC-C)-CH$_2$ and isopropylic -CH); 2.00 t ((OC)CH$_2$); 2.32 s (NCH$_3$); 2.49 s (DMSOd$_5$); 2.82 m (Z2); 2.9÷3.8 (sugar protons; 4.12 m (X6); 4.44 s (X1); 4.33 d (X5); 4.37 d (X7); 4.95 m (X2); 5.06÷5.10 (4F and Z6); 5.38 d (anomeric proton of acylaminoglucuronic acid); 5.59 d (X4); 5.72 s (4B); 6.05 d (X3); 7.74 s (6B); 6.27÷8.5 (aromatic and peptidic NH's)

(D) Retention time (R$_t$) of 1.30 relative to Teicoplanin A$_2$ component 2 (R$_t$=20.3 min) when analyzed by reverse phase HPLC under the following conditions:

column: Ultrasphere ODS (5 μm) Altex (Beckman) 4.6 mm (i.d.)×250 mm
pre-column: Brownlee Labs RP 18 (5 μm)

| eluent A: | CH$_3$CN | 10% | adjusted at |
| | (2.5 g/l) NaH$_2$PO$_4$.H$_2$O | 90% | pH 6.0 |
| eluent B: | CH$_3$CN | 70% | adjusted at |
| | (2.5 g/l) NaH$_2$PO$_4$.H$_2$O | 30% | pH 6.0 | elution: linear gradient from 5% to 60% of eluent B in eluent A, in 40 min
flow rate: 1.8 ml/min
U.V. detector: 254 nm
internal standard: Teicoplanin A$_2$ component 2 (Gruppo Lepetit S.p.A.)

(E) Molecular weight of about 1568 as determined by FAB-MS
(F) acid functions capable of forming salts
(G) amino function capable of forming salts
(H) no mannose unit linked to the core moiety.

Antibiotic A 40926 N-acylaminoglucuronyl aglycon factor B$_1$ (in the non-addition salt form) has molecular weight of about 1568 as determined by FAB-MS and substantially the same physicochemical characteristics reported above for antibiotic A 40926 N-acylaminoglucuronyl aglycon factor B$_0$ except that it has a triplet at 0.84 δppm attributable to the methyl group of an n-propyl function in the NMR system reported above and a retention time relative to Teicoplanin A$_2$ component 2 of 1.32 in the system reported above.

Antibiotic A 40926 aglycon (in the non-addition salt form)

(A) ultraviolet absorption spectrum which exhibits the following absorption maxima:

| | λ max (nm) |
|---|---|
| (a) 0.1 N HCl | 280 |
| (b) phosphate buffer pH 7.4 | 280 |
| | 310 (shoulder) |
| (c) 0.1 N KOH | 299 |

(B) infrared absorption spectrum which exhibits the following absorption maxima (cm$^{-1}$): 3700–3100; 3000–2800 (nujol); 1655; 1620–1550; 1500; 1460

(nujol); 1375 (nujol); 1300; 1205; 1145; 1010; 970; 930; 840

(C) $^1$H-NMR spectrum which exhibits the following groups of signals (in ppm) at 270 MHz recorded in DMSO d$_6$ (hexadeuterodimethylsulfoxide) plus CF$_3$COOH using TMS as the internal standard (0.00 ppm), ($\delta$=ppm): 2.51 s (DMSOd$_5$); 2.50 s (NCH$_3$); 2.88 m (Z2); 3.33 m (Z'2); 4.10 m (X6); 4.34 d (X5); 4.43 d (X7); 4.93 m (X2); 5.04 s (4F); 5.09 s (Z6); 5.54 d (X4); 5.75 s (4B); 6.05 d (X3); 7.76 s (6B); 6.3–8.4 (aromatic and peptidic NH's)

(D) Retention time (R$_t$) of 0.59 relative to Teicoplanin A$_2$ component 2 (R$_t$=20.3 min) when analyzed by reverse phase HPLC under the following conditions:

column: Ultrasphere ODS (5 μm) Altex (Beckman) 4.6 mm (i.d.)×250 mm pre-column: Brownlee Labs RP 18 (5 μm)

| eluent A: | CH$_3$CN | 10% | adjusted at |
| | (2.5 g/l) NaH$_2$PO$_4$.H$_2$O | 90% | pH 6.0 |
| eluent B: | CH$_3$CN | 70% | adjusted at |
| | (2.5 g/l) NaH$_2$PO$_4$.H$_2$O | 30% | pH 6.0 | elution: linear gradient from 5% to 60% of eluent B in eluent A, in 40 min flow rate: 1.8 ml/min U.V. detector: 254 nm internal standard: Teicoplanin A$_2$ component 2 (Gruppo Lepetit S.p.A.)

Under the same conditions the retention time relative to antibiotic L 17054 (Gruppo Lepetit, EP-A-119575) is 1.42

(E) Molecular weight of about 1211 as determined by FAB-MS (F) acid functions capable of forming salts (G) amino function capable of forming salts (H) no mannose unit linked to the core moiety.

2. An antibiotic substance selected from antibiotic A 40926 N-acylaminoglucuronyl aglycon complex AB, antibiotic A 40926 N-acylaminoglucuronyl aglycon factor A, antibiotic A 40926 N-acylaminoglucuronyl aglycon factor B, antibiotic A 40926 N-acylaminoglucuronyl aglycon factor B$_0$, antibiotic A 40926 N-acylaminoglucuronyl aglycon factor B$_1$, antibiotic A 40926 aglycon and the addition salts thereof, which has the following formula:

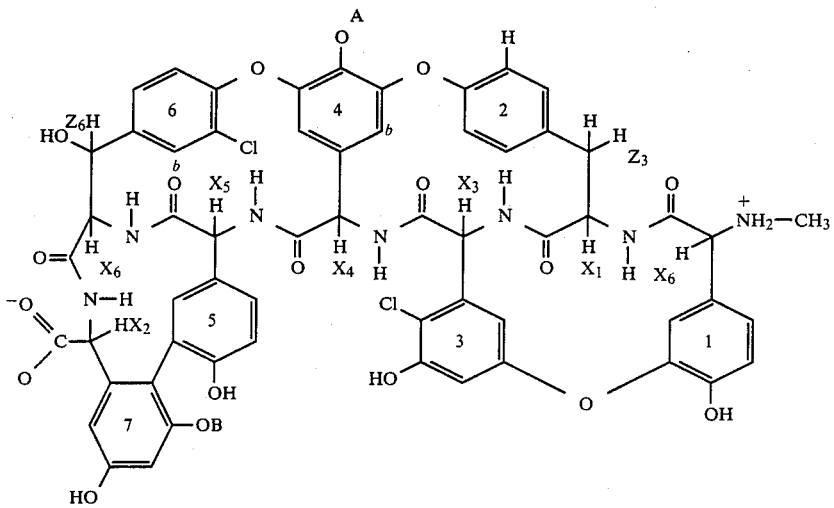

wherein

A represents hydrogen or a N-(C$_{11}$-C$_{12}$)acylaminoglucuronyl selected from the group consisting of undecanoylaminoglucuronyl, dodecanoylaminoglucuronyl and isododecanoylaminoglucuronyl and represents hydrogen.

3. A compound according to claim 2, wherein A and B are represented by hydrogen.

4. A compound according to claim 2, wherein A is represented by undecanoylaminoglucuronyl and B is represented by hydrogen.

5. A compound according to claim 2, wherein A is represented by dodecanoylaminoglucoronyl and B is represented by hydrogen.

6. A compound according to claim 2, wherein A is represented by isododecanoylaminoglucoronyl and B is represented by hydrogen.

7. A process for preparing a compound of claim 1, 2, 9, 3, 4, 5 or 6 or a mixture thereof which comprises:

(a) subjecting antibiotic A 40926 complex, antibiotic A 40926 complex AB, antibiotic A 40926 factor A, antibiotic A 40926 factor B, antibiotic A 40926 factor B$_0$, antibiotic A 40926 factor PA, antibiotic A 40926 factor PB to controlled acid hydrolysis with a strong acid in a suitable organic solvent in the presence of a limited (0.1–10% w/w) amount of water (b) when a mixture of final products is obtained, optionally separating them by chromatographic procedure.

8. A process for preparing antibiotic A 40926 N-acylaminoglucuronyl aglycon complex AB or a factor thereof which comprises subjecting antibiotic A 40926 complex, antibiotic A 40926 complex AB, antibiotic A 40926 factor A, antibiotic A 40926 factor B, antibiotic A 40926 factor B$_0$, antibiotic A 40926 factor PA, antibiotic A 40926 factor PB to controlled acid hydrolysis with a mixture from 9:1 to 9.5:0.5 of dimethylsulfoxide/37% (w/w) hydrochloride acid at a temperature of about 65° C. for about 5 h, optionally separating antibiotic a 40926 N-acylaminoglucuronyl aglycon factor A and antibiotic A 40926 N-acylaminoglucuronyl aglycon factor B by chromatographic procedure.

9. A process for preparing antibiotic A 40926 aglycon which comprises subjecting antibiotic A 40926 complex, or a single factor thereof, antibiotic A 40926 complex AB, antibiotic A 40926 factor A, antibiotic A 40926 factor B, antibiotic A 40926 factor PA, antibiotic A 40926 factor PB, antibiotic A 40926 factor $B_0$, antibiotic A 40926 mannosyl aglycon and antibiotic A 40926 N-acylaminoglucuronyl aglycon (complex AB/or a single factor thereof) to controlled acid hydrolysis in the presence of:

(a) an organic protic solvent selected from aliphatic acids and alpha-halogenated aliphatic acids which at the reaction temperature are liquids, aliphatic and cycloaliphatic alkanols which at the reaction temperature are liquids slightly mixable with water, phenyl substituted lower alkanols wherein the phenyl moiety may optionally carry ($C_1$-$C_4$)alkyl, ($C_1$-$C_4$)alkoxy or halo rests which at the reaction temperature are liquids slightly mixable with water, and beta-polyhalogenated lower alkanols, which at the reaction temperature are liquids, (b) a strong acid compatible with the solvent selected from strong mineral acids, strong organic acids and strong acid cation exchanger resins in the hydrogen form, and (c) at a reaction temperature between about 20° C. and about 100° C.

10. A pharmaceutical composition comprising a compound of claim 1, 2, 9, 3, 4, 5 or 12, present in an effective amount in admixture with a pharmaceutically acceptable carrier.

11. A method for treating infectious diseases which comprises administering an antimicrobially effective amount of a compound of claim 1, 2, 9, 3, 4, 5 or 6 to a patient in need thereof.

* * * * *

UNITED STATES PATENT AND TRADEMARK OFFICE
CERTIFICATE OF

PATENT NO. : 4,868,171

DATED : September 19, 1989

INVENTOR(S) : Enrico Selva, et al.

It is certified that error appears in the above-identified patent and that said Letters Patent is hereby corrected as shown below:

At column 42, line 31, claim 2, the patent reads "and represents" and should read --and B represents--.

Signed and Sealed this

Second Day of July, 1991

Attest:

HARRY F. MANBECK, JR.

*Attesting Officer*    *Commissioner of Patents and Trademarks*